US008066995B2

(12) United States Patent
Davies et al.

(10) Patent No.: US 8,066,995 B2
(45) Date of Patent: Nov. 29, 2011

(54) ANTI-MYOSTATIN ANTIBODIES

(75) Inventors: Julian Davies, San Diego, CA (US);
Bryan Edward Jones, San Diego, CA (US); Andrew Ihor Korytko, Oceanside, CA (US); Pamela Jean Mitchell, Indianapolis, IN (US); Rosamund Carol Smith, Greenfield, IN (US); Linda O'Bryan (Nee Tobias), Indianapolis, IN (US); Rong Wang, Wildwood, MO (US)

(73) Assignee: Eli Lilly and Company, Indianapolis, IN (US)

( * ) Notice: Subject to any disclaimer, the term of this patent is extended or adjusted under 35 U.S.C. 154(b) by 204 days.

(21) Appl. No.: 12/611,470

(22) Filed: Nov. 3, 2009

(65) Prior Publication Data
US 2010/0080811 A1 Apr. 1, 2010

Related U.S. Application Data

(63) Continuation of application No. 12/066,838, filed as application No. PCT/US2006/038817 on Oct. 5, 2006, now Pat. No. 7,632,499.

(60) Provisional application No. 60/725,738, filed on Oct. 12, 2005.

(51) Int. Cl.
*A61K 39/395* (2006.01)
(52) U.S. Cl. ................ 424/133.1; 424/135.1; 530/387.3
(58) Field of Classification Search .................. None
See application file for complete search history.

(56) References Cited

U.S. PATENT DOCUMENTS

| | | | |
|---|---|---|---|
| 5,639,638 A | 6/1997 | Wozney et al. |
| 5,700,911 A | 12/1997 | Wozney et al. |
| 5,827,733 A | 10/1998 | Lee et al. |
| 5,914,234 A | 6/1999 | Lee et al. |
| 6,096,506 A | 8/2000 | Lee et al. |
| 6,340,668 B1 | 1/2002 | Celeste et al. |
| 6,368,597 B1 | 4/2002 | Strassmann et al. |
| 6,437,111 B1 | 8/2002 | Wozney et al. |
| 6,468,535 B1 | 10/2002 | Lee et al. |
| 6,500,664 B1 | 12/2002 | Lee et al. |
| 6,517,835 B2 | 2/2003 | Lee et al. |
| 6,656,475 B1 | 12/2003 | Lee et al. |
| 6,696,260 B1 | 2/2004 | Lee et al. |
| 6,858,208 B2 | 2/2005 | Lee et al. |
| 7,175,997 B2 | 2/2007 | Wozney et al. |
| 7,179,884 B2 | 2/2007 | Lee et al. |
| 7,261,893 B2 | 8/2007 | Veldman et al. |
| 7,320,789 B2 | 1/2008 | Aghajanian et al. |
| 7,371,726 B2 | 5/2008 | Junker et al. |
| 7,511,012 B2 | 3/2009 | Han et al. |
| 7,534,432 B2 | 5/2009 | Lee et al. |
| 7,585,648 B2 | 9/2009 | Junker et al. |
| 2002/0150577 A1 | 10/2002 | Lee et al. |
| 2003/0138422 A1 | 7/2003 | Aghajanian et al. |
| 2004/0142382 A1 | 7/2004 | Veldman et al. |
| 2004/0181033 A1 | 9/2004 | Han et al. |
| 2005/0014733 A1 | 1/2005 | Whittemore et al. |
| 2005/0043232 A1 | 2/2005 | Lee et al. |
| 2005/0143306 A1 | 6/2005 | Junker et al. |
| 2006/0034831 A1 | 2/2006 | Tobin |
| 2006/0240487 A1 | 10/2006 | Nowak et al. |
| 2006/0263354 A1 | 11/2006 | Chin et al. |
| 2007/0087000 A1 | 4/2007 | Walsh et al. |
| 2007/0149458 A1 | 6/2007 | Han et al. |
| 2007/0178095 A1 | 8/2007 | Smith et al. |
| 2007/0190056 A1 | 8/2007 | Kambadur et al. |
| 2008/0051328 A1 | 2/2008 | Sharma et al. |
| 2008/0187543 A1 | 8/2008 | Kambadur et al. |
| 2008/0299126 A1 | 12/2008 | Han et al. |
| 2009/0017045 A1 | 1/2009 | Lee et al. |
| 2009/0017522 A1 | 1/2009 | Lee et al. |
| 2009/0131638 A1 | 5/2009 | Davies et al. |
| 2009/0136481 A1 | 5/2009 | Kambadur et al. |
| 2009/0215671 A1 | 8/2009 | Calof et al. |
| 2009/0220491 A1 | 9/2009 | Han et al. |
| 2009/0311282 A1 | 12/2009 | Junker et al. |

FOREIGN PATENT DOCUMENTS

| | | |
|---|---|---|
| EP | 1333035 | 8/2003 |
| GB | 2333706 A | 4/1999 |
| WO | 94/21681 | 9/1994 |
| WO | 94/26892 | 11/1994 |
| WO | 96/01845 | 1/1996 |
| WO | 9835019 | 8/1998 |
| WO | 99/06559 | 2/1999 |
| WO | 99/24058 | 5/1999 |
| WO | 99/40181 | 8/1999 |
| WO | 00/43781 | 7/2000 |
| WO | 02/09641 | 2/2002 |
| WO | 02/10214 | 2/2002 |
| WO | 03/027248 | 4/2003 |
| WO | 2004/037861 | 5/2004 |
| WO | 2004/058988 | 7/2004 |
| WO | 2004/108157 | 12/2004 |

(Continued)

OTHER PUBLICATIONS

Ashmore, et al., "Comparative Aspects of Muscle Fiber Types in Fetuses of the Normal and 'Double-Muscled' Cattle," Growth 38:501-506 (1974).
Bogdanovich, et al., "Functional Improvement of Dystrophic Muscle by Myostatin Blockade," Nature 420:418-421 (2002).
Bogdanovich, et al., "Therapeutics for Duchenne Muscular Dystrophy: Current Approaches and Future Directions," J. Mol. Med. 82:102-115 (2004).
Gamer, et al., "Gdf11 is a Negative Regulator of Chondrogenesis and Myogenesis in the Developing Chick Limb," Dev. Biol. 229:407-420 (2001).
Gamer, et al., "A Novel BMP Expressed in Developing Mouse Limb, Spinal Cord, and Tail Bud Is a Potent Mesoderm Inducer in Xenopus Embryos," Dev. Biol. 208:222-232 (1999).

(Continued)

*Primary Examiner* — Sheela J Huff
(74) *Attorney, Agent, or Firm* — Gregory A. Cox

(57) ABSTRACT

Anti-myostatin antibodies are identified that are characterized as having high affinity and may be chimeric, humanized or fully human antibodies, immunoconjugates of the antibodies or antigen-binding fragments thereof. The antibodies of the invention are useful for increasing muscle mass, increasing bond density, or for the treatment of various disorders in mammalian and avian species, X17251.

18 Claims, 15 Drawing Sheets

FOREIGN PATENT DOCUMENTS

| | | |
|---|---|---|
| WO | 2005066204 | 7/2005 |
| WO | 2005/094446 | 10/2005 |
| WO | 2006020884 | 2/2006 |
| WO | 2006/116269 | 11/2006 |
| WO | 2007/024535 | 3/2007 |
| WO | 2007/044411 | 4/2007 |
| WO | 2007047112 | 4/2007 |
| WO | 2007067616 | 6/2007 |
| WO | 2008/030706 | 3/2008 |
| WO | 2008109167 | 9/2008 |

OTHER PUBLICATIONS

Gonzalez-Cadavid, et al., "Organization of the Human Myostatin Gene and Expression in Healthy Men and HIV-Infected Men With Muscle Wasting," PNAS 95:14938-14943 (1998).

Gonzales-Cadavid, et al., "Role of Myostatin in Metabolism," Curr. Opin. Clin. Nutr. Metab. Care 7:451-457 (2004).

Grobet, et al., "A Deletion in the Bovine Myostatin Gene Causes the Double-Muscled Phenotype in Cattle," Nature Genet. 17:71-74 (1997).

Hamrick, et al., "Femoral Morphology and Cross-Sectional Geometry of Adult Myostatin-Deficient Mice," Bone 27:343-349 (2000).

Hamrick, et al., "Bone Mineral Content and Density in the Humerus of Adult Myostatin-Deficient Mice," Calcif. Tissue Int. 71(1):63-68 (2002).

Hill, et al., "The Myostatin Propeptide and the Follistatin-Related Gene Are Inhibitory Binding Proteins of Myostatin in Normal Serum," J. Biol. Chem. 277:40735-40741 (2002).

Hill, et al., "Regulation of Myostatin in Vivo by Growth and Differentiation Factor-Associated Serum Protein-1: A Novel Protein with Protease Inhibitor and Follistatin Domains," Mol. Endocrinol. 17:1144-1154 (2003).

Hoodless, et al., "Mechanisms and Function of Signaling by the TGF beta Superfamily," Current Topics in Microbiology and Immunology pp. 236-272 (1998).

Huet, et al., "Skeletal Muscle Cell Hypertrophy Induced by Inhibitors of Metalloproteases; Myostatin as a Potential Mediator," Am. J. Physiol. Cell. Physiol. 281:C1624-C1634 (2001).

Jiang, et al., "Characterization and Identification of the Inhibitory Domain of GDF-8 Propeptide," Biochem. Biophys. Res. Commun. 315:525-531 (2004).

Kambadur, et al., "Mutations in Myostatin (GDF8) in Double-Muscled Belgian Blue and Piedmontese Cattle," Genome Res. 7:910-915 (1997).

Kim, et al., "Inhibition of Preadipocyte Differentiation by Myostatin Treatment in 3T3-L1 Cultures," Biochem. Biophys. Res. Comm., 281:902-906 (2001).

Kingsley, D.M., "The TGF beta Superfamily: New Members, New Receptors, and New Genetic Tests of Function in Different Organisms," Genes & Devel. 8:133-146 (1994).

Kirk, et al., "Myostatin Regulation During Skeletal Muscle Regeneration," J. Cell. Physiol., 184:356-363 (2000).

Lang, et al., "Regulation of Myostatin by Glucocorticoids After Thermal Injury," FASEB J. 15:1807-1809 (2001).

Lee, et al., "Regulation of Myostatin Activity and Muscle Growth," PNAS 98:9306-9311 (2001).

Li, et al., "Elimination of Myostatin Does Not Combat Muscular Dystophy in dy Mice but Increases Postnatal Lethality," AJP. 166 (2) 491-497, 2005.

Lin, et al., "Myostatin Knockout in Mice Increases Myogenesis and Decreases Adipogenesis," Biochem. Biophys. Res. Comm., 291:701-706 (2002).

Massagué, J., "The Transforming Growth Factor—beta Family," Ann. Rev. Cell Biol. 6:597-641 (1990).

McPherron, et al., "Double Muscling in Cattle Due to Mutations in the Myostatin Gene," PNAS 94:12457-12461 (1997).

McPherron, et al., "Regulation of Skeletal Muscle Mass in Mice by a New TGF—beta Superfamily Member," Nature 387:83-90 (1997).

McPherron, et al., "Suppression of Body Fat Accumulation in Myostatin-Deficient Mice," J. Clin. Invest. 109:595-601 (2002).

Muscaritoli, et al., "Therapy of Muscle Wasting in Cancer: What Is the Future?" Curr. Opin. Clin. Nutr. Metab. Care, 7:459-466 (2004).

Nakashima, et al., "Expression of Growth/Differentiation Factor 11, A New Member of the BMP/TGF beta Superfamily During Mouse Embryogenesis," Mech. Dev. 80:185-189 (1999).

Reardon, et al., "Myostatin, Insulin-Like Growth Factor-1, and Leukemia Inhibitory Factor mRNAs Are Upregulated in Chronic Human Disuse Muscle Atrophy," Muscle Nerve, 24:893-899 (2001).

Rios, et al., "Myostatin Is an Inhibitor of Myogenic Differentiation," Am. J. Physiol. Cell Physiol., 282: C993-C999 (2002).

Roth, et al., "Myostatin: A Therapeutic Target for Skeletal Muscle Wasting," Curr. Opin. Clin. Nutr. Metab. Care, 7:259-263 (2004).

Sharma, et al., "Myostatin, a Transforming Growth Factor—beta Superfamily Member, Is Expressed in Heart Muscle and Is Upregulated in Cardiomyocytes After Infarct," J. Cell. Physiol., 180:1-9 (1999).

Swatland, et al., "Fetal Development of the Double Muscled Condition in Cattle," J. Animal Sci. 38:752-757 (1974).

Thies, et al., "GDF-8 Propeptide Binds to GDF-8 and Antagonizes Biological Activity by Inhibiting GDF-8 Receptor Binding," Growth Factors 18:251-259 (2001).

Thomas, et al., "Myostatin, a Negative Regulator of Muscle Growth, Functions by Inhibiting Myoblast Proliferation," J. Biol. Chem., 275 (51) 40235-40243 (2000).

Tseng, et al., "Regenerated mdx Mouse Skeletal Muscle Shows Differential mRNA Expression," J. Appl. Physiol. 93:537-545 (2002).

Tsuchida, et al., "Identification and Characterization of a Novel Follistatin-like Protein as a Binding Protein for the TGF-beta Family," J. Biol. Chem. 275:40788-40796 (2000).

Wagner, et al., "Loss of Myostatin Attenuates Severity of Muscular Dystrophy in mdx Mice," Ann. Neurol. 52:832-836 (2002).

Wakefield, et al., "Latent Transforming Growth Factor—beta From Human Platelets," J. Biol. Chem. 263:7646-7654 (1988).

Whittemore, et al., "Inhibition of Myostatin in Adult Mice Increases Skeletal Muscle Mass and Strength," Biochem. Biophys. Res. Comm. 300:965-971 (2003).

Zhu, et al., "Dominant Negative Myostatin Produces Hypertrophy Without Hyperplasia in Muscle," FEBS Letters 474:71-75 (2000).

Zimmers, et al., "Induction of Cachexia in Mice by Systematically Administered Myostatin," Science 296:1486-1488 (2002).

Tchistiakova, L., "Anti-Myostatin Antibody for Treatment of Muscle Wasting Diseases," Antibody Therapeutics Meeting, San Diego, CA, Dec. 7, 2005.

FIG. 1  Promyostatin

```
1    MQKLQLCVYI YLFMLIVAGP VDLNENSEQK ENVEKEGLCN    40
41   ACTWRQNTKS SRIEAIKIQI LSKLRLETAP NISKDVIRQL    80
81   LPKAPPLREL IDQYDVQRDD SSDGSLEDDD YHATTETIIT    120
121  MPTESDFLMQ VDGKPKCCFF KFSSKIQYNK VVKAQLWIYL    160
161  RPVETPTTVF VQILRLIKPM KDGTRYTGIR SLKLDMNPGT    200
201  GIWQSIDVKT VLQNWLKQPE SNLGIEIKAL DENGHDLAVT    240
241  FPGPGEDGLN PFLEVKVTDT PKRSRRDFGL DCDEHSTESR    280
281  CCRYPLTVDF EAFGWDWIIA PKRYKANYCS GECEFVFLQK    320
321  YPHTHLVHQA NPRGSAGPCC TPTKMSPINM LYFNGKEQII    360
361  YGKIPAMVVD RCGCS 376  (SEQ ID NO:1)
```

FIG. 2  Mature Myostatin (Human, murine, rat, chicken, turkey, dog, horse, pig)

```
1    DFGLDCDEHS TESRCCRYPL TVDFEAFGWD WIIAPKRYKA    40
41   NYCSGECEFV FLQKYPHTHL VHQANPRGSA GPCCTPTKMS    80
81   PINMLYFNGK EQIIYGKIPA MVVDRCGCS 109  (SEQ ID NO:2)
```

FIG. 3  Mature myostatin

```
                                                                        58
chicken  DFGLDCDEHSTESRCCRYPLTVDFEAFGWDWIIAPKRYKANYCSGECEFVFLQKYPHTH
dog      DFGLDCDEHSTESRCCRYPLTVDFEAFGWDWIIAPKRYKANYCSGECEFVFLQKYPHTH
horse    DFGLDCDEHSTESRCCRYPLTVDFEAFGWDWIIAPKRYKANYCSGECEFVFLQKYPHTH
sheep    DFGLDCDEHSTESRCCRYPLTVDFEAFGWDWIIAPKRYKANYCSGECEFLFLQKYPHTH
cow      DFGLDCDEHSTESRCCRYPLTVDFEAFGWDWIIAPKRYKANYCSGECEFVFLQKYPHTH
pig      DFGLDCDEHSTESRCCRYPLTVDFEAFGWDWIIAPKRYKANYCSGECEFVFLQKYPHTH

109    SEQ ID
chicken  LVHQANPRGSAGPCCTPTKMSPINMLYFNGKEQIIYGKIPAMVVDRCGCS    2
dog      LVHQANPRGSAGPCCTPTKMSPINMLYFNGKEQIIYGKIPAMVVDRCGCS    2
horse    LVHQANPRGSAGPCCTPTKMSPINMLYFNGKEQIIYGKIPAMVVDRCGCS    2
sheep    LVHQANPKGSAGPCCTPTKMSPINMLYFNGKEQIIYGKIPGMVVDRCGCS    3
cow      LVHQANPRGSAGPCCTPTKMSPINMLYFNGEGQIIYGKIPAMVVDRCGCS    2
pig      LVHQANPRGSAGPCCTPTKMSPINMLYFNGKEQIIYGKIPAMVVDRCGCS    2
```

FIG. 4  Myostatin:GDF-11 Homology

```
Myostatin  DFGLDCDEHSTESRCCRYPLTVDFEAFGWDWIIAPKRYK
GDF-11     NLGLDCDEHSSESRCCRYPLTVDFEAFGWDWIIAPKRYK Myostatin  ANYCSGECEFVFLQKYPHTHLVHQANPRGSAGPCCTPTK
GDF-11     ANYCSGQCEYMFMQKYPHTHLVQQANPRGSAGPCCTPTK Myostatin  MSPINMLYFNGKEQIIYGKIPAMVVDRCGCS  (SEQ ID NO:2)
GDF-11     MSPINMLYFNDKQQIIYGKIPGMVVDRCGCS  (SEQ ID NO:4)
```

FIG. 5 Parent Antibody

YN41 HCVR DNA

5' - GAGGTGAAGCTGGTGGAGTCTGGGGGAGGCTTAGTGAAGCCTGGAGGGTC
    CCTGAAACTCTCCTGTGCAGCCTCTGGACTCACTTTCAGTAGGTATGGCA
    TGTCTTGGGTTCGCCAGACTCCGGAGAGGAGGCTGGAGTGGGTCGCAGCC
    ATTAATAGTCATGGTGGTAGCACCTACTATTCAGACACTGTGAAGGGCCG
    ATTCACCATTTCCAGAGACAATGCCAAGAACACCCTGTACCTGCAAATGA
    ACAGTCTGAGGTCTGAGGACACAGCCTTGTATTACTGTGCAAGACTTCCG
    GACTACTGGGGCCAAGGCACCACGGTCACCGTTTCCTCA (SEQ ID NO: 5)

YN41 HCVR Amino acids

EVKLVESGGG LVKPGGSLKL SCAASGLTFS RYGMSWVRQT PERRLEWVAA
    INSHGGSTYY SDTVKGRFTI SRDNAKNTLY LQMNSLRSED TALYYCARLP
    DYWGQGTTVT VSS (SEQ ID NO: 7)

YN41 LCVR (Kappa) DNA

5' - GAAAATGTGCTGACCCAGTCTCCAGCAATCATGTCTGCATCTCCAGGGGA
    AAAGGTCACCATGACCTGCAGGGCCAGCTCAAGTGTAAGTTCCAGTTACT
    TGCACTGGTACCAGCAGAAGTCAGGTGCCTCCCCCAAACTCTGGATCTAT
    AGCACATCCAACTTGGCTTCTGGAGTCCCTGCTCGCTTCAGTGGCAGTGG
    GTCTGGGACCTCTTACTCTCTCACAATCAGCAGTGTGGAGGCTGAAGATG
    CTGCCACTTATTACTGCCAGCAGTACAGTGGTTACCACTTCACGTTCGGC
    TCGGGGACCAAGCTGGAAATGAAA (SEQ ID NO: 6)

YN41 LCVR (Kappa) Amino acids

ENVLTQSPAI MSASPGEKVT MTCRASSSVS SSYLHWYQQK SGASPKLWIY
    STSNLASGVP ARFSGSGSGT SYSLTISSVE AEDAATYYCQ QYSGYHFTFG
    SGTKLEMK (SEQ ID NO: 8)

FIG. 6    Light Chain CDR Alignment

|        | CDR1        | SEQ ID NO. | CDR2    | SEQ ID NO. | CDR3      | SEQ ID NO. |
|--------|-------------|-----------|---------|-----------|-----------|-----------|
| YN41   | RASSSVSSSYLH | 9  | STSNLAS | 13 | QQYSGYHFT | 24 |
| 41-1   | RASQSVSSSYLH | 10 | STSNLAA | 14 | QHYSGYHFT | 25 |
| 41-2   | RASSSVSSSYLH | 9  | STSNLAT | 15 | QNYSGYHFT | 26 |
| 41-3   | RASSSVSSSYLH | 9  | STSNLAS | 13 | QQYSGYFFT | 27 |
| 41-4   | RASSSVSSSYLH | 9  | STSNLAS | 13 | QQYSGYQFT | 28 |
| 41-5   | RASSSVSSSYLH | 9  | STSNLAS | 13 | QQYSGYTFT | 29 |
| 41-6   | RASSSVSSSYLH | 9  | STSNLAS | 13 | QQYSGYQFT | 28 |
| 41-8   | RASSSVSSSYLH | 9  | STSNLAS | 13 | QQYSGYSFT | 30 |
| 41-9   | RASSSVSSSYLH | 9  | STSNLAT | 15 | QHYSGYHFT | 25 |
| 41-10  | RASSSVSSSYLH | 9  | STSNLAT | 15 | QHYSGYHFT | 25 |
| 41-11  | RASSSVSSSYLH | 9  | STSNLAA | 14 | QLYSGYHFT | 31 |
| 41-12  | RASSSVSSSYLH | 9  | STSNLAT | 15 | QHYSGYHFT | 25 |
| 41-13  | RASSSVSSSYLH | 9  | STSNLAT | 15 | QHYSGYHFT | 25 |
| 41-14  | RASSSVSSSYLH | 9  | STSNLAT | 15 | QHYSGYHFT | 25 |
| 41-15  | RASSSVSSSYLH | 9  | STSNLAT | 15 | QHYSGYHFT | 25 |
| 41-17  | RASSSVSSSYLH | 9  | STSNLAT | 15 | QPYSGYHFT | 32 |
| 41-18  | RASSSVSSSYLH | 9  | STSNLAN | 16 | QHYSGYHFT | 25 |
| 41-19  | RASSSVSSSYLH | 9  | STSNLAT | 15 | QHYSGYHFT | 25 |
| 41-20  | RASSSVSSSYLH | 9  | STSNLAS | 13 | QQYSGYQFT | 28 |
| 411-1  | RASSSVSSSYLH | 9  | STSNLAT | 15 | QHYSGYHFT | 25 |
| 411-2  | RASSSVSSSYLH | 9  | STSNLAA | 14 | QHYSGYHFT | 25 |
| 411-4  | RASSSVSSSYLH | 9  | STSNLAA | 14 | QHYSGYHFT | 25 |
| 411-5  | RASSSVSSSYLH | 9  | STSNLAT | 15 | QHYSGYHFT | 25 |
| 411-6  | RASSSVSSSYLH | 9  | STSNLAA | 14 | QHYSGYHFT | 25 |
| 411-7  | RASSSVSSSYLH | 9  | STSNLAD | 17 | QHYSGYHFT | 25 |
| 411-10 | RASSSVSSSYLH | 9  | STSNLAT | 15 | QHYSGYHFT | 25 |
| 411-11 | RASSSVSSSYLH | 9  | STSNLAT | 15 | QHYSGYHFT | 25 |
| 411-12 | RASSSVSSSYLH | 9  | STSNLAT | 15 | QHYSGYHFT | 25 |
| 411-13 | RASSSVSSSYLH | 9  | STSNLAT | 15 | QHYSGYHFT | 25 |
| 411-15 | RASSSVSSSYLH | 9  | STSNLAA | 14 | QPYSGYHFT | 32 |
| 411-16 | RASSSVSSSYLH | 9  | STSNLAA | 14 | QPYSGYHFT | 32 |
| 412-1  | RASSSVSSSYLH | 9  | STSNLVA | 18 | QHYSGYHFT | 25 |
| 412-5  | RASSSVSSSYLH | 9  | STSNLVA | 18 | QHYLGYHFT | 33 |
| 412-6  | RASSSVSSSYLH | 9  | STSNLVA | 18 | QHYSGYHFT | 25 |
| 412-8  | RASSSVSSSYLH | 9  | STSNLVA | 18 | QHYLGYHFT | 33 |
| 412-9  | RASSSVSSSYLH | 9  | STSNLVA | 18 | QHYLGYHFT | 33 |
| 412-13 | RALSSVSSSYLH | 11 | STSNLAA | 14 | QHYLGYHFT | 33 |
| 412-14 | RASSSVSSSYLH | 9  | STSNLAA | 14 | QHYLGYHFT | 33 |
| 412-15 | RASSSVSSSYLH | 9  | STSNLAA | 14 | QHYLGYHFT | 33 |
| 412-16 | RASSSVSSSYLH | 9  | STSNLAA | 14 | QHYSGYHFT | 25 |
| 41L2-A1 | RASSSVSSSYLH | 9 | STSNLVF | 19 | QHYSGYHFT | 25 |
| 41L2-A2 | RASSSVSSSYLH | 9 | STSNLTW | 20 | QHYSGYHFT | 25 |
| 41L2-A3 | RASSSVSSSYLH | 9 | STSNLMD | 21 | QHYSGYHFT | 25 |
| 41L2-E3 | RASSSVSSSYLH | 9 | STSNLVY | 22 | QHYSGYHFT | 25 |
| 41L2-E9 | RASSSVSSSYLH | 9 | STSNLVW | 23 | QHYSGYHFT | 25 |
| 41L3-F12 | RASSSVSSSYLH | 9 | STSNLVA | 18 | QHHSGYHFT | 34 |
| 41L3-G2 | RASSSVSSSYLH | 9 | STSNLVA | 18 | QHYSGYHWT | 35 |
| 41L3-G6 | RASSSVSSSYLH | 9 | STSNLVA | 18 | QWYSGYHFT | 36 |
| 41H-A7 | RASSSVSSSYLH | 9 | STSNLVA | 18 | QHYSGYHFT | 25 |
| 41H-B8 | RASSSVSSSYLH | 9 | STSNLVA | 18 | QHYSGYHFT | 25 |

FIG. 6 Continued

```
41H-D6       RASSSVSSSYLH    9    STSNLVA    18    QHYSGYHFT    25
41H-D11      RASSSVSSSYLH    9    STSNLVA    18    QHYSGYHFT    25
41H-E11      RASSSVSSSYLH    9    STSNLVA    18    QHYSGYHFT    25
41H-E4       RASSSVSSSYLH    9    STSNLVA    18    QHYSGYHFT    25
41H-E5       RASSSVSSSYLH    9    STSNLVA    18    QHYSGYHFT    25
41H-E7       RASSSVSSSYLH    9    STSNLVA    18    QHYSGYHFT    25
41H-E9       RASSSVSSSYLH    9    STSNLVA    18    QHYSGYHFT    25
41H-E12      RASSSVSSSYLH    9    STSNLVA    18    QHYSGYHFT    25
41H-F10      RASSSVSSSYLH    9    STSNLVA    18    QHYSGYHFT    25
41H-F12      RASSSVSSSYLH    9    STSNLVA    18    QHYSGYHFT    25
41C1A2       RASSSVSSSYLH    9    STSNLVY    22    QHYSGYHFT    25
41C1A4       RASSSVSSSYLH    9    STSNLVY    22    QHHSGYHFT    34
41C1C1       RASSSVSSSYLH    9    STSNLVA    18    QHYSGYHWT    35
41C1E4       RASSSVSSSYLH    9    STSNLVA    18    QHHSGYHFT    34
41C2A1       RASSSVSSSYLH    9    STSNLVA    18    QHYSGYHWT    35
41C2A4       RASSSVSSSYLH    9    STSNLVA    18    QHHSGYHWT    36
41C2E4       RASSSVSSSYLH    9    STSNLVY    22    QHYSGYHWT    35
41C2G8       RASSSVSSSYLH    9    STSNLVY    22    QHYSGYHFT    25
3-74/C1A2    RASSSVSSSYLH    9    STSNLVY    22    QHYSGYHFT    25
3-74/C1A4    RASSSVSSSYLH    9    STSNLVY    22    QHHSGYHFT    34
3-74/C1E4    RASSSVSSSYLH    9    STSNLVA    18    QHYSGYHFT    25
3-74/C2A4    RASSSVSSSYLH    9    STSNLVA    18    QHHSGYHWT    36

Consensus    RAX₃X₄SVSSSYLH  12    STSNLX₆X₇  154   QX₂X₃X₄GYX₇X₈T  37
             X₃:S or L            X₆:A,V,T or M          X₂:Q,N,H,L,P or W
             X₄:S or Q            X₇:S,A,T,N,W,D or Y    X₃:Y or H
                                                         X₄:S or L
                                                         X₇:H,F,Q or T
                                                         X₈:F or W
```

FIG. 7  Heavy Chain CDR Alignment

| Fab | CDR1 | SEQ ID NO | CDR2 | SEQ ID NO | CDR3 | SEQ ID NO |
|---|---|---|---|---|---|---|
| YN41 | GLTFSRYGMS | 38 | AINSHGGSTYYSDTVKG | 43 | LPDY | 72 |
| 41-1 | GLTFSRYGMS | 38 | AINSSGGSTYYSDTVKG | 44 | LPDY | 72 |
| 41-2 | GLTFSRYGMS | 38 | AINSRGGSTYYSDTVKG | 45 | LPDY | 72 |
| 41-3 | GLTFSRYGMS | 38 | AINSRGGSTYYSDTVKG | 45 | LPDY | 72 |
| 41-4 | GLTFSRYGMS | 38 | AINSSGGSTYYSDTVKG | 44 | LPDY | 72 |
| 41-5 | GLTFSRYGMS | 38 | AINSVGGSTYYSDTVKG | 46 | LPDY | 72 |
| 41-6 | GLTFSRYGMS | 38 | AINSSGGSTYYSDTVKG | 44 | LPDY | 72 |
| 41-8 | GLTFSRYGMS | 38 | AINSEGGSTYYSDTVKG | 47 | LPDY | 72 |
| 41-9 | GLTFSRYGMS | 38 | AINSRGGSTYYSDTVKG | 45 | LPDY | 72 |
| 41-10 | GLTFSRYGMS | 38 | AINSIGGSTYYSDTVKG | 48 | LPDY | 72 |
| 41-11 | GLTFSRYGMS | 38 | AINSRGGSTYYSDTVKG | 45 | LPDY | 72 |
| 41-12 | GLTFSRYGMS | 38 | AINSMGGSTYYSDTVKG | 49 | LPDY | 72 |
| 41-13 | GLTFSRYGMS | 38 | AINSTGGSTYYSDTVKG | 50 | LPDY | 72 |
| 41-14 | GLTFSRYGMS | 38 | AINSSGGSTYYSDTVKG | 44 | LPDY | 72 |
| 41-16 | GLTFSRYGMS | 38 | AINSKGGSTYYSDTVKG | 51 | LPDY | 72 |
| 41-17 | GLTFSRYGMS | 38 | AINSPGGSTYYSDTVKG | 52 | LPDY | 72 |
| 41-18 | GLTFSRYGMS | 38 | AINSGGGSTYYSDTVKG | 53 | LPDY | 72 |
| 41-19 | GLTFSRYGMS | 38 | AINSSGGSTYYSDTVKG | 44 | LPDY | 72 |
| 41-20 | GLTFSRYGMS | 38 | AINSYGGSTYYSDTVKG | 54 | LPDY | 72 |
| 411-1 | GLTFSRYGMS | 38 | AINSSGGSTYYADSVKG | 73 | LPDY | 72 |
| 411-2 | GLTFSRYGMS | 38 | AINSSGGSTYYSDTVKG | 44 | LPDY | 72 |
| 411-4 | GLTFSRYGMS | 38 | AINSMGGSTYYSDTVKG | 49 | LPDY | 72 |
| 411-5 | GLTFSRYGMS | 38 | AINSRGGSTYYSDTVKG | 45 | LPDY | 72 |
| 411-6 | GLTFSRYGMS | 38 | AINSWGGSTYYSDTVKG | 55 | LPDY | 72 |
| 411-7 | GLTFSRYGMS | 38 | AINSAGGSTYYSDTVKG | 56 | LPDY | 72 |
| 411-10 | GLTFSRYGMS | 38 | AINSSGGSTYYSDTVKG | 44 | LPDY | 72 |
| 411-11 | GLTFSRYGMS | 38 | AINSDGGSTYYSDTVKG | 57 | LPDY | 72 |
| 411-12 | GLTFSRYGMS | 38 | AINSGGGSTYYSDTVKG | 53 | LPDY | 72 |
| 411-13 | GLTFSRYGMS | 38 | AINSLGGSTYYSDTVKG | 58 | LPDY | 72 |
| 411-14 | GLTFSRYGMS | 38 | AINSNGGSTYYSDTVKG | 59 | LPDY | 72 |
| 411-16 | GLTFSRYGMS | 38 | AINSSGGSTYYSDTVKG | 44 | LPDY | 72 |
| 412-1 | GLTFSRYGMS | 38 | AINSSGGSTYYSDTVKG | 44 | LPDY | 72 |
| 412-5 | GLTFSRYGMS | 38 | AINSSGGSTYYSDTVKG | 44 | LPDY | 72 |
| 412-6 | GLTFSRYGMS | 38 | AITSSGGSTYYSDTVKG | 60 | LPDY | 72 |
| 412-8 | GLTFSRYTMS | 39 | AINSSGGSTYYSDTVKG | 44 | LPDY | 72 |
| 412-9 | GLTFSRYTMS | 39 | AIKSSGGSTYYSDTVKG | 61 | LPDY | 72 |
| 412-13 | GLTFSRYTMS | 39 | AINSSGGSTYYSDTVKG | 44 | LPDY | 72 |
| 412-14 | GLTFSRYGMS | 38 | AINSSGGSTYYSDTVKG | 44 | LPDY | 72 |
| 412-15 | GLTFSRYTMS | 39 | AINSSGGSTYYSDTVKG | 44 | LPDY | 72 |
| 412-16 | GLTFSRYGMS | 38 | AINSSGGSTYYSDTVKG | 44 | LPDY | 72 |
| 41L2-A1 | GLTFSRYGMS | 38 | AITSSGGSTYYSDTVKG | 60 | LPDY | 72 |
| 41L2-A2 | GLTFSRYGMS | 38 | AITSSGGSTYYSDTVKG | 60 | LPDY | 72 |
| 41L2-A3 | GLTFSRYGMS | 38 | AITSSGGSTYYSDTVKG | 60 | LPDY | 72 |
| 41L2-E3 | GLTFSRYGMS | 38 | AITSSGGSTYYSDTVKG | 60 | LPDY | 72 |
| 41L2-E9 | GLTFSRYGMS | 38 | AITSSGGSTYYSDTVKG | 60 | LPDY | 72 |
| 41L3-F12 | GLTFSRYGMS | 38 | AITSSGGSTYYSDTVKG | 60 | LPDY | 72 |
| 41L3-G2 | GLTFSRYGMS | 38 | AITSSGGSTYYSDTVKG | 60 | LPDY | 72 |
| 41L3-G6 | GLTFSRYGMS | 38 | AITSSGGSTYYSDTVKG | 60 | LPDY | 72 |
| 41H-A7 | GLTFSRYPMS | 40 | AITSSGGSTYYSDTVKG | 60 | LPDY | 72 |
| 41H-B8 | GLNFSRYGMS | 41 | AITSSGGSTYYSDTVKG | 60 | LPDY | 72 |
| 41H-D6 | GLTFSRYGMS | 38 | AIKSSGGSTYYSDTVKG | 61 | LPDY | 72 |
| 41H-D11 | GLTFSRYGMS | 38 | AIKSNGGSTYYSDTVKG | 62 | LPDY | 72 |
| 41H-E11 | GLTFSRYGMS | 38 | RITSSGGSTYYSDTVKG | 63 | LPDY | 72 |
| 41H-E4 | GLTFSRYGMS | 38 | HIKSSGGSTYYSDTVKG | 64 | LPDY | 72 |
| 41-E5 | GLTFSRYGMS | 38 | AITSSGGSTKYSDTVKG | 65 | LPDY | 72 |

FIG 7 Continued

```
41H-E7     GLTFSRYGMS  38    AIKASGGSTYYSDTVKG  66    LPDY  72
41H-E9     GLTFSRYGMS  38    AIKSSGSSTYYSDTVKG  67    LPDY  72
41H-E12    GLTFSRYGMS  38    AIKSLGGSTYYSDTVKG  68    LPDY  72
41H-F10    GLTFSRYGMS  38    AITSMGGSTYYSDTVKG  69    LPDY  72
41H-F12    GLTFSRYGMS  38    AQTSSGGSTYYSDTVKG  70    LPDY  72
41C1A2     GLTFSRYPMS  40    RITSSGGSTYYSDTVKG  63    LPDY  72
41C1A4     GLTFSRYPMS  40    RITSSGGSTYYSDTVKG  63    LPDY  72
41C1C1     GLTFSRYPMS  40    AIKSSGGSTYYSDTVKG  61    LPDY  72
41C1E4     GLTFSRYPMS  40    AITSSGGSTYYSDTVKG  60    LPDY  72
41C2A1     GLTFSRYPMS  40    AITSSGGSTYYSDTVKG  60    LPDY  72
41C2A4     GLTFSRYPMS  40    AITSSGGSTYYSDTVKG  60    LPDY  72
41C2E4     GLTFSRYPMS  40    AIKSSGGSTYYSDTVKG  61    LPDY  72
41C2G8     GLTFSRYPMS  40    RITSSGGSTYYSDTVKG  63    LPDY  72
3-74/C1A2  GLTFSRYPMS  40    RITSSGGSTYYSDTVKG  63    LPDY  72
3-74/C1A4  GLTFSRYPMS  40    RITSSGGSTYYSDTVKG  63    LPDY  72
3-74/C1E4  GLTFSRYPMS  40    AITSSGGSTYYSDTVKG  60    LPDY  72
3-74/C2A4  GLTFSRYPMS  40    AITSSGGSTYYSDTVKG  60    LPDY  72

Consensus  GLX3FSRYX8MS  42   X1X2X3X4X5GX7STX10YSDTVKG  71
           X3:T or N           X1:A, R or H
           X8:G, T or P        X2:I or Q
                               X3:N, T or K
                               X4:S or A
                               X5:H,S,V,L,M,N,G,D,W,R,A,Y,K,P,T,I or E
                               X7:G or S
                               X10:Y or K
```

FIG. 8

Kappa Constant (SEQ ID NO: 155)

VAAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

Kappa Constant DNA (SEQ ID NO: 156)

GTGGCTGCACCATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCACAAAGAGCTTC
AACAGGGGAGAGTGC

IgG4S->P Delta K (SEQ ID NO: 157)

GPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFS
CSVMHEALHNHYTQKSLSLSLG

IgG4S->P Delta K DNA (SEQ ID NO: 158)

GGCCCATCGGTCTTCCCGCTAGCGCCCTGCTCCAGGAGCACCTCCGAGAGCACAGCCGCC
CTGGGCTGCCTGGTCAAGGACTACTTCCCCGAACCGGTGACGGTGTCGTGGAACTCAGGC
GCCCTGACCAGCGGCGTGCACACCTTCCCGGCTGTCCTACAGTCCTCAGGACTCTACTCC
GCTCAGCAGCGTGGTGACCGTGCCCTCCAGCAGCTTGGGCACGAAGACCTACACCTGCAA
CGTAGATCACAAGCCCAGCAACACCAAGGTGGACAAGAGAGTTGAGTCCAAATATGGTCC
CCCATGCCCACCCTGCCCAGCACCTGAGTTCCTGGGGGGACCATCAGTCTTCCTGTTCCC
CCCAAAACCCAAGGACACTCTCATGATCTCCCGGACCCCTGAGGTCACGTGCGTGGTGGT
GGACGTGAGCCAGGAAGACCCCGAGGTCCAGTTCAACTGGTACGTGGATGGCGTGGAGGT
GCATAATGCCAAGACAAAGCCGCGGGAGGAGCAGTTCAACAGCACGTACCGTGTGGTCAG
CGTCCTCACCGTCCTGCACCAGGACTGGCTGAACGGCAAGGAGTACAAGTGCAAGGTCTC
CAACAAAGGCCTCCCGTCCTCCATCGAGAAAACCATCTCCAAAGCCAAAGGGCAGCCCCG
AGAGCCACAGGTGTACACCCTGCCCCCATCCCAGGAGGAGATGACCAAGAACCAGGTCAG
CCTGACCTGCCTGGTCAAAGGCTTCTACCCCAGCGACATCGCCGTGGAGTGGGAAAGCAA
TGGGCAGCCGGAGAACAACTACAAGACCACGCCTCCCGTGCTGGACTCCGACGGCTCCTT
CTTCCTCTACAGCAGGCTAACCGTGGACAAGAGCAGGTGGCAGGAGGGGAATGTCTTCTC
ATGCTCCGTGATGCATGAGGCTCTGCACAACCACTACACACAGAAGAGCCTCTCCCTGTC
TCTGGGTTGA

FIG. 9 Light Chain Sequence Alignments

```
                                   CDR1                         CDR2
          1         10        20        30        40        50
41-1      EIVLTQSPGTLSLSPGERATLSCRASQSVSSSYLHWYQQKPGQAPRLLIYSTSNLAAG
41-2      EIVLTQSPGTLSLSPGERATLSCRASSSVSSSYLHWYQQKPGQAPRLLIYSTSNLATG
41-3      EIVLTQSPGTLSLSPGERATLSCRASSSVSSSYLHWYQQKPGQAPRLLIYSTSNLASG
41-4      EIVLTQSPGTLSLSPGERATLSCRASSSVSSSYLHWYQQKPGQAPRLLIYSTSNLASG
41-5      EIVLTQSPGTLSLSPGERATLSCRASSSVSSSYLHWYQQKPGQAPRLLIYSTSNLASG
41-6      EIVLTQSPGTLSLSPGERATLSCRASSSVSSSYLHWYQQKPGQAPRLLIYSTSNLASG
41-8      EIVLTQSPGTLSLSPGERATLSCRASSSVSSSYLHWYQQKPGQAPRLLIYSTSNLASG
41-9      EIVLTQSPGTLSLSPGERATLSCRASSSVSSSYLHWYQQKPGQAPRLLIYSTSNLATG
41-10     EIVLTQSPGTLSLSPGERATLSCRASSSVSSSYLHWYQQKPGQAPRLLIYSTSNLATG
41-11     EIVLTQSPGTLSLSPGERATLSCRASSSVSSSYLHWYQQKPGQAPRLLIYSTSNLAAG
41-12     EIVLTQSPGTLSLSPGERATLSCRASSSVSSSYLHWYQQKPGQAPRLLIYSTSNLATG
41-13     EIVLTQSPGTLSLSPGERATLSCRASSSVSSSYLHWYQQKPGQAPRLLIYSTSNLATG
41-14     EIVLTQSPGTLSLSPGERATLSCRASSSVSSSYLHWYQQKPGQAPRLLIYSTSNLATG
41-15     EIVLTQSPGTLSLSPGERATLSCRASSSVSSSYLHWYQQKPGQAPRLLIYSTSNLATG
41-17     EIVLTQSPGTLSLSPGERATLSCRASSSVSSSYLHWYQQKPGQAPRLLIYSTSNLATG
41-18     EIVLTQSPGTLSLSPGERATLSCRASSSVSSSYLHWYQQKPGQAPRLLIYSTSNLANG
41-19     EIVLTQSPGTLSLSPGERATLSCRASSSVSSSYLHWYQQKPGQAPRLLIYSTSNLATG
41-20     EIVLTQSPGTLSLSPGERATLSCRASSSVSSSYLHWYQQKPGQAPRLLIYSTSNLASG
411-1     EIVLTQSPGTLSLSPGERATLSCRASSSVSSSYLHWYQQKPGQAPRLLIYSTSNLATG
411-2     EIVLTQSPGTLSLSPGERATLSCRASSSVSSSYLHWYQQKPGQAPRLLIYSTSNLAAG
411-4     EIVLTQSPGTLSLSPGERATLSCRASSSVSSSYLHWYQQKPGQAPRLLIYSTSNLAAG
411-5     EIVLTQSPGTLSLSPGERATLSCRASSSVSSSYLHWYQQKPGQAPRLLIYSTSNLATG
411-6     EIVLTQSPGTLSLSPGERATLSCRASSSVSSSYLHWYQQKPGQAPRLLIYSTSNLAAG
411-7     EIVLTQSPGTLSLSPGERATLSCRASSSVSSSYLHWYQQKPGQAPRLLIYSTSNLADG
411-10    EIVLTQSPGTLSLSPGERATLSCRASSSVSSSYLHWYQQKPGQAPRLLIYSTSNLATG
411-11    EIVLTQSPGTLSLSPGERATLSCRASSSVSSSYLHWYQQKPGQAPRLLIYSTSNLATG
411-12    EIVLTQSPGTLSLSPGERATLSCRASSSVSSSYLHWYQQKPGQAPRLLIYSTSNLATG
411-13    EIVLTQSPGTLSLSPGERATLSCRASSSVSSSYLHWYQQKPGQAPRLLIYSTSNLATG
411-15    EIVLTQSPGTLSLSPGERATLSCRASSSVSSSYLHWYQQKPGQAPRLLIYSTSNLAAG
411-16    EIVLTQSPGTLSLSPGERATLSCRASSSVSSSYLHWYQQKPGQAPRLLIYSTSNLAAG
412-1     EIVLTQSPGTLSLSPGERATLSCRASSSVSSSYLHWYQQKPGQAPRLLIYSTSNLVAG
412-5     EIVLTQSPGTLSLSPGERATLSCRASSSVSSSYLHWYQQKPGQAPRLLIYSTSNLVAG
412-6     EIVLTQSPGTLSLSPGERATLSCRASSSVSSSYLHWYQQKPGQAPRLLIYSTSNLVAG
412-8     EIVLTQSPGTLSLSPGERATLSCRASSSVSSSYLHWYQQKPGQAPRLLIYSTSNLVAG
412-9     EIVLTQSPGTLSLSPGERATLSCRASSSVSSSYLHWYQQKPGQAPRLLIYSTSNLVAG
412-13    EIVLTQSPGTLSLSCRALSSVSSSYLHWYQQKPGQAPRLLIYSTSNLAAG
412-14    EIVLTQSPGTLSLSPGERATLSCRASSSVSSSYLHWYQQKPGQAPRLLIYSTSNLAAG
412-15    EIVLTQSPGTLSLSPGERATLSCRASSSVSSSYLHWYQQKPGQAPRLLIYSTSNLAAG
412-16    EIVLTQSPGTLSLSPGERATLSCRASSSVSSSYLHWYQQKPGQAPRLLIYSTSNLAAG
41L2-A1   EIVLTQSPGTLSLSPGERATLSCRASSSVSSSYLHWYQQKPGQAPRLLIYSTSNLVFG
41L2-A2   EIVLTQSPGTLSLSPGERATLSCRASSSVSSSYLHWYQQKPGQAPRLLIYSTSNLTWG
41L2-A3   EIVLTQSPGTLSLSPGERATLSCRASSSVSSSYLHWYQQKPGQAPRLLIYSTSNLMDG
41L2-E3   EIVLTQSPGTLSLSPGERATLSCRASSSVSSSYLHWYQQKPGQAPRLLIYSTSNLVYG
41L2-E9   EIVLTQSPGTLSLSPGERATLSCRASSSVSSSYLHWYQQKPGQAPRLLIYSTSNLVWG
```

FIG. 9 continued

```
                                                        CDR3                      SEQ.
                                                                                   ID
              60        70        80        90        100                         NO:
41-1     IPDRFSGSGSGTDFTLTISRLEPEDFAVYYCQHYSGYHFTFGGGTKVEIK                         74
41-2     IPDRFSGSGSGTDFTLTISRLEPEDFAVYYCQNYSGYHFTFGGGTKVEIK                         75
41-3     IPDRFSGSGSGTDFTLTISRLEPEDFAVYYCQQYSGYFFTFGGGTKLEIK                         76
41-4     IPDRFSGSGSGTDFTLTISRLEPEDFAVYYCQQYSGYQFTFGGGTKVEIK                         77
41-5     IPDRFSGSGSGTDFTLTISRLEPEDFAVYYCQQYSGYTFTFGGGTKVEIK                         78
41-6     IPDRFSGSGSGTDFTLTISRLEPEDFAVYYCQQYSGYQFTFGGGTKLEIK                         79
41-8     IPDRFSGSGSGTDFTLTISRLEPEDFAVYYCQQYSGYSFTFGGGTKVEIK                         80
41-9     IPDRFSGSGSGTDFTLTISRLEPEDFAVYYCQHYSGYHFTFGGGTKVEIK                         81
41-10    IPDRFSGSGSGTDFTLTISRLEPEDFAVYYCQHYSGYHFTFGGGTKVEIK                         81
41-11    IPDRFSGSGSGTDFTLTISRLEPEDFAVYYCQLYSGYHFTFGGGTKVEIK                         82
41-12    IPDRFSGSGSGTDFTLTISRLEPEDFAVYYCQHYSGYHFTFGGGTKVEIK                         81
41-13    IPDRFSGSGSGTDFTLTISRLEPEDFAVYYCQHYSGYHFTFGGGTKVEIK                         81
41-14    IPDRFSGSGSGTDFTLTISRLEPEDFAVYYCQHYSGYHFTFGGGTKVEIK                         81
41-15    IPDRFSGSGSGTDFTLTISRLEPEDFAVYYCQHYSGYHFTFGGGTKVEIK                         81
41-17    IPDRFSGSGSGTDFTLTISRLEPEDFAVYYCQPYSGYHFTFGGGTKVEIK                         83
41-18    IPDRFSGSGSGTDFTLTISRLEPEDFAVYYCQHYSGYHFTFGGGTKVEIK                         84
41-19    IPDRFSGSGSGTDFTLTISRLEPEDFAVYYCQHYSGYHFTFGGGTKVEIK                         81
41-20    IPDRFSGSGSGTDFTLTISRLEPEDFAVYYCQQYSGYQFTFGGGTKVEIK                         85
411-1    IPDRFSGSGSGTDFTLTISRLEPEDFAVYYCQHYSGYHFTFGGGTKVEIK                         81
411-2    IPDRFSGSGSGTDFTLTISRLEPEDFAVYYCQHYSGYHFTFGGGTKVEIK                         86
411-4    IPDRFSGSGSGTDFTLTISRLEPEDFAVYYCQHYSGYHFTFGGGTKVEIK                         86
411-5    IPDRFSGSGSGTDFTLTISRLEPEDFAVYYCQHYSGYHFTFGGGTKVEIK                         81
411-6    IPDRFSGSGSGTDFTLTISRLEPEDFAVYYCQHYSGYHFTFGGGTKVEIK                         86
411-7    IPDRFSGSGSGTDFTLTISRLEPEDFAVYYCQHYSGYHFTFGGGTKVEIK                         87
411-10   IPDRFSGSGSGTDFTLTISRLEPEDFAVYYCQHYSGYHFTFGGGTKVEIK                         81
411-11   IPDRFSGSGSGTDFTLTISRLEPEDFAVYYCQHYSGYHFTFGGGTKVEIK                         81
411-12   IPDRFSGSGSGTDFTLTISRLEPEDFAVYYCQHYSGYHFTFGGGTKVEIK                         81
411-13   IPDRFSGSGSGTDFTLTISRLEPEDFAVYYCQHYSGYHFTFGGGTKVEIK                         81
411-15   IPDRFSGSGSGTDFTLTISRLEPEDFAVYYCQPYSGYHFTFGGGTKVEIK                         88
411-16   IPDRFSGSGSGTDFTLTISRLEPEDFAVYYCQPYSGYHFTFGGGTKVEIK                         88
412-1    IPDRFSGSGSGTDFTLTISRLEPEDFAVYYCQHYSGYHFTFGGGTKVEIK                         89
412-5    IPDRFSGSGSGTDFTLTISRLEPEDFAVYYCQHYLGYHFTFGGGTKVEIK                         90
412-6    IPDRFSGSGSGTDFTLTISRLEPEDFAVYYCQHYSGYHFTFGGGTKVEIK                         89
412-8    IPDRFSGSGSGTDFTLTISRLEPEDFAVYYCQHYLGYHFTFGGGTKVEIK                         90
412-9    IPDRFSGSGSGTDFTLTISRLEPEDFAVYYCQHYLGYHFTFGGGTKVEIK                         90
412-13   IPDRFSGSGSGTDFTLTISRLEPEDFAVYYCQHYLGYHFTFGGGTKVEIK                         91
412-14   IPDRFSGSGSGTDFTLTISRLEPEDFAVYYCQHYLGYHFTFGGGTKVEIK                         92
412-15   IPDRFSGSGSGTDFTLTISRLEPEDFAVYYCQHYLGYHFTFGGGTKVEIK                         92
412-16   IPDRFSGSGSGTDFTLTISRLEPEDFAVYYCQHYSGYHFTFGGGTKVEIK                         86
41L2-A1  IPDRFSGSGSGTDFTLTISRLEPEDFAVYYCQHYSGYHFTFGGGTKVEIK                         93
41L2-A2  IPDRFSGSGSGTDFTLTISRLEPEDFAVYYCQHYSGYHFTFGGGTKVEIK                         94
41L2-A3  IPDRFSGSGSGTDFTLTISRLEPEDFAVYYCQHYSGYHFTFGGGTKVEIK                         95
41L2-E3  IPDRFSGSGSGTDFTLTISRLEPEDFAVYYCQHYSGYHFTFGGGTKVEIK                         96
41L2-E9  IPDRFSGSGSGTDFTLTISRLEPEDFAVYYCQHYSGYHFTFGGGTKVEIK                         97
```

FIG. 9 continued

```
                                          CDR1
                  CDR2
                  1         10        20        30        40        50
    41L3-F12      EIVLTQSPGTLSLSPGERATLSCRASSSVSSSYLHWYQQKPGQAPRLLIYSTSNLVAG
    41L3-G2       EIVLTQSPGTLSLSPGERATLSCRASSSVSSSYLHWYQQKPGQAPRLLIYSTSNLVAG
    41L3-G6       EIVLTQSPGTLSLSPGERATLSCRASSSVSSSYLHWYQQKPGQAPRLLIYSTSNLVAG
    41H-A7        EIVLTQSPGTLSLSPGERATLSCRASSSVSSSYLHWYQQKPGQAPRLLIYSTSNLVAG
    41H-B8        EIVLTQSPGTLSLSPGERATLSCRASSSVSSSYLHWYQQKPGQAPRLLIYSTSNLVAG
    41H-D6        EIVLTQSPGTLSLSPGERATLSCRASSSVSSSYLHWYQQKPGQAPRLLIYSTSNLVAG
    41H-D11       EIVLTQSPGTLSLSPGERATLSCRASSSVSSSYLHWYQQKPGQAPRLLIYSTSNLVAG
    41H-E11       EIVLTQSPGTLSLSPGERATLSCRASSSVSSSYLHWYQQKPGQAPRLLIYSTSNLVAG
    41H-E4        EIVLTQSPGTLSLSPGERATLSCRASSSVSSSYLHWYQQKPGQAPRLLIYSTSNLVAG
    41H-E5        EIVLTQSPGTLSLSPGERATLSCRASSSVSSSYLHWYQQKPGQAPRLLIYSTSNLVAG
    41H-E7        EIVLTQSPGTLSLSPGERATLSCRASSSVSSSYLHWYQQKPGQAPRLLIYSTSNLVAG
    41H-E9        EIVLTQSPGTLSLSPGERATLSCRASSSVSSSYLHWYQQKPGQAPRLLIYSTSNLVAG
    41H-E12       EIVLTQSPGTLSLSPGERATLSCRASSSVSSSYLHWYQQKPGQAPRLLIYSTSNLVAG
    41H-F10       EIVLTQSPGTLSLSPGERATLSCRASSSVSSSYLHWYQQKPGQAPRLLIYSTSNLVAG
    41H-F12       EIVLTQSPGTLSLSPGERATLSCRASSSVSSSYLHWYQQKPGQAPRLLIYSTSNLVAG
    41C1A2        EIVLTQSPGTLSLSPGERATLSCRASSSVSSSYLHWYQQKPGQAPRLLIYSTSNLVYG
    41C1A4        EIVLTQSPGTLSLSPGERATLSCRASSSVSSSYLHWYQQKPGQAPRLLIYSTSNLVYG
    41C1C1        EIVLTQSPGTLSLSPGERATLSCRASSSVSSSYLHWYQQKPGQAPRLLIYSTSNLVAG
    41C1E4        EIVLTQSPGTLSLSPGERATLSCRASSSVSSSYLHWYQQKPGQAPRLLIYSTSNLVAG
    41C2A1        EIVLTQSPGTLSLSPGERATLSCRASSSVSSSYLHWYQQKPGQAPRLLIYSTSNLVAG
    41C2A4        EIVLTQSPGTLSLSPGERATLSCRASSSVSSSYLHWYQQKPGQAPRLLIYSTSNLVAG
    41C2E4        EIVLTQSPGTLSLSPGERATLSCRASSSVSSSYLHWYQQKPGQAPRLLIYSTSNLVYG
    41C2G8        EIVLTQSPGTLSLSPGERATLSCRASSSVSSSYLHWYQQKPGQAPRLLIYSTSNLVYG
    3-74/C1A2     EIVLTQSPGTLSLSPGERATLSCRASSSVSSSYLHWYQQKPGQAPRLLIYSTSNLVYG
    3-74/C1A4     EIVLTQSPGTLSLSPGERATLSCRASSSVSSSYLHWYQQKPGQAPRLLIYSTSNLVYG
    3-74/C1E4     EIVLTQSPGTLSLSPGERATLSCRASSSVSSSYLHWYQQKPGQAPRLLIYSTSNLVAG
    3-74/C2A4     EIVLTQSPGTLSLSPGERATLSCRASSSVSSSYLHWYQQKPGQAPRLLIYSTSNLVAG
```

FIG. 9 continued

```
                                                           CDR3                         SEQ
               60        70        80        90        100                              ID
                                                                                        NO:
41L3-F12   IPDRFSGSGSGTDFTLTISRLEPEDFAVYYCQHHSGYHFTFGGGTKVEIK                             98
41L3-G2    IPDRFSGSGSGTDFTLTISRLEPEDFAVYYCQHYSGYHWTFGGGTKVEIK                             99
41L3-G6    IPDRFSGSGSGTDFTLTISRLEPEDFAVYYCQWYSGYHFTFGGGTKVEIK                            100
41H-A7     IPDRFSGSGSGTDFTLTISRLEPEDFAVYYCQHYSGYHFTFGGGTKVEIK                             89
41H-B8     IPDRFSGSGSGTDFTLTISRLEPEDFAVYYCQHYSGYHFTFGGGTKVEIK                             89
41H-D6     IPDRFSGSGSGTDFTLTISRLEPEDFAVYYCQHYSGYHFTFGGGTKVEIK                             89
41H-D11    IPDRFSGSGSGTDFTLTISRLEPEDFAVYYCQHYSGYHFTFGGGTKVEIK                             89
41H-E11    IPDRFSGSGSGTDFTLTISRLEPEDFAVYYCQHYSGYHFTFGGGTKVEIK                             89
41H-E4     IPDRFSGSGSGTDFTLTISRLEPEDFAVYYCQHYSGYHFTFGGGTKVEIK                             89
41H-E5     IPDRFSGSGSGTDFTLTISRLEPEDFAVYYCQHYSGYHFTFGGGTKVEIK                             89
41H-E7     IPDRFSGSGSGTDFTLTISRLEPEDFAVYYCQHYSGYHFTFGGGTKVEIK                             89
41H-E9     IPDRFSGSGSGTDFTLTISRLEPEDFAVYYCQHYSGYHFTFGGGTKVEIK                             89
41H-E12    IPDRFSGSGSGTDFTLTISRLEPEDFAVYYCQHYSGYHFTFGGGTKVEIK                             89
41H-F10    IPDRFSGSGSGTDFTLTISRLEPEDFAVYYCQHYSGYHFTFGGGTKVEIK                             89
41H-F12    IPDRFSGSGSGTDFTLTISRLEPEDFAVYYCQHYSGYHFTFGGGTKVEIK                             89
41C1A2     IPDRFSGSGSGTDFTLTISRLEPEDFAVYYCQHYSGYHFTFGGGTKVEIK                             96
41C1A4     IPDRFSGSGSGTDFTLTISRLEPEDFAVYYCQHHSGYHFTFGGGTKVEIK                            101
41C1C1     IPDRFSGSGSGTDFTLTISRLEPEDFAVYYCQHYSGYHWTFGGGTKVEIK                             99
41C1E4     IPDRFSGSGSGTDFTLTISRLEPEDFAVYYCQHHSGYHFTFGGGTKVEIK                             98
41C2A1     IPDRFSGSGSGTDFTLTISRLEPEDFAVYYCQHYSGYHWTFGGGTKVEIK                             99
41C2A4     IPDRFSGSGSGTDFTLTISRLEPEDFAVYYCQHHSGYHWTFGGGTKVEIK                            141
41C2E4     IPDRFSGSGSGTDFTLTISRLEPEDFAVYYCQHYSGYHWTFGGGTKVEIK                            102
41C2G8     IPDRFSGSGSGTDFTLTISRLEPEDFAVYYCQHYSGYHFTFGGGTKVEIK                             96
3-74/C1A2  IPDRFSGSGSGTDFTLTISRLEPEDFAVYYCQHYSGYHFTFGGGTKVEIK                             95
3-74/C1A4  IPDRFSGSGSGTDFTLTISRLEPEDFAVYYCQHHSGYHFTFGGGTKVEIK                            140
3-74/C1E4  IPDRFSGSGSGTDFTLTISRLEPEDFAVYYCQHHSGYHFTFGGGTKVEIK                             98
3-74/C2A4  IPDRFSGSGSGTDFTLTISRLEPEDFAVYYCQHHSGYHWTFGGGTKVEIK                            142

L-FR1      EIVLTQSPGTLSLSPGERATLSC              SEQ ID NO: 143
L-FR2      WYAAKPGQAPRLLIY                      SEQ ID NO: 144
L-FR3      GIPDRFSGSGSGTDFTLTISRLEPEDFAVYYC     SEQ ID NO: 145
L-FR4      FGGGTKVEIK                           SEQ ID NO: 146
L-FR4B     FGGGTKLEIK                           SEQ ID NO: 147
```

FIG. 10 - Heavy Chain Sequence Alignments

```
                                              CDR1                         CDR2
              1         10        20        30        40        50
41-1          EVQLLESGGGLVQPGGSLRLSCAASGLTFSRYGMSWVRQAPGKGLEWVSAINSSGGS
41-2          EVQLLESGGGLVQPGGSLRLSCAASGLTFSRYGMSWVRQAPGKGLEWVSAINSRGGS
41-3          EVQLLESGGGLVQPGGSLRLSCAASGLTFSRYGMSWVRQAPGKGLEWVSAINSRGGS
41-4          EVQLLESGGGLVQPGGSLRLSCAASGLTFSRYGMSWVRQAPGKGLEWVSAINSSGGS
41-5          EVQLLESGGGLVQPGGSLRLSCAASGLTFSRYGMSWVRQAPGKGLEWVSAINSVGGS
41-6          EVQLLESGGGLVQPGGSLRLSCAASGLTFSRYGMSWVRQAPGKGLEWVSAINSSGGS
41-8          EVQLLESGGGLVQPGGSLRLSCAASGLTFSRYGMSWVRQAPGKGLEWVSAINSEGGS
41-9          EVQLLESGGGLVQPGGSLRLSCAASGLTFSRYGMSWVRQAPGKGLEWVSAINSRGGS
41-10         EVQLLESGGGLVQPGGSLRLSCAASGLTFSRYGMSWVRQAPGKGLEWVSAINSIGGS
41-11         EVQLLESGGGLVQPGGSLRLSCAASGLTFSRYGMSWVRQAPGKGLEWVSAINSRGGS
41-12         EVQLLESGGGLVQPGGSLRLSCAASGLTFSRYGMSWVRQAPGKGLEWVSAINSMGGS
41-13         EVQLLESGGGLVQPGGSLRLSCAASGLTFSRYGMSWVRQAPGKGLEWVSAINSTGGS
41-14         EVQLLESGGGLVQPGGSLRLSCAASGLTFSRYGMSWVRQAPGKGLEWVSAINSSGGS
41-16         EVQLLESGGGLVQPGGSLRLSCAASGLTFSRYGMSWVRQAPGKGLEWVSAINSKGGS
41-17         EVQLLESGGGLVQPGGSLRLSCAASGLTFSRYGMSWVRQAPGKGLEWVSAINSPGGS
41-18         EVQLLESGGGLVQPGGSLRLSCAASGLTFSRYGMSWVRQAPGKGLEWVSAINSGGGS
41-19         EVQLLESGGGLVQPGGSLRLSCAASGLTFSRYGMSWVRQAPGKGLEWVSAINSSGGS
41-20         EVQLLESGGGLVQPGGSLRLSCAASGLTFSRYGMSWVRQAPGKGLEWVSAINSYGGS
411-1         EVQLLESGGGLVQPGGSLRLSCAASGLTFSRYGMSWVRQAPGKGLEWVSAINSSGGS
411-2         EVQLLESGGGLVQPGGSLRLSCAASGLTFSRYGMSWVRQAPGKGLEWVSAINSSGGS
411-4         EVQLLESGGGLVQPGGSLRLSCAASGLTFSRYGMSWVRQAPGKGLEWVSAINSMGGS
411-5         EVQLLESGGGLVQPGGSLRLSCAASGLTFSRYGMSWVRQAPGKGLEWVSAINSRGGS
411-6         EVQLLESGGGLVQPGGSLRLSCAASGLTFSRYGMSWVRQAPGKGLEWVSAINSWGGS
411-7         EVQLLESGGGLVQPGGSLRLSCAASGLTFSRYGMSWVRQAPGKGLEWVSAINSAGGS
411-10        EVQLLESGGGLVQPGGSLRLSCAASGLTFSRYGMSWVRQAPGKGLEWVSAINSSGGS
411-11        EVQLLESGGGLVQPGGSLRLSCAASGLTFSRYGMSWVRQAPGKGLEWVSAINSDGGS
411-12        EVQLLESGGGLVQPGGSLRLSCAASGLTFSRYGMSWVRQAPGKGLEWVSAINSGGGS
411-13        EVQLLESGGGLVQPGGSLRLSCAASGLTFSRYGMSWVRQAPGKGLEWVSAINSLGGS
411-14        EVQLLESGGGLVQPGGSLRLSCAASGLTFSRYGMSWVRQAPGKGLEWVSAINSNGGS
411-16        EVQLLESGGGLVQPGGSLRLSCAASGLTFSRYGMSWVRQAPGKGLEWVSAINSSGGS
412-1         EVQLLESGGGLVQPGGSLRLSCAASGLTFSRYGMSWVRQAPGKGLEWVSAINSSGGS
412-5         EVQLLESGGGLVQPGGSLRLSCAASGLTFSRYGMSWVRQAPGKGLEWVSAINSSGGS
412-6         EVQLLESGGGLVQPGGSLRLSCAASGLTFSRYGMSWVRQAPGKGLEWVSAITSSGGS
412-8         EVQLLESGGGLVQPGGSLRLSCAASGLTFSRYTMSWVRQAPGKGLEWVSAINSSGGS
412-9         EVQLLESGGGLVQPGGSLRLSCAASGLTFSRYTMSWVRQAPGKGLEWVSAIKSSGGS
412-13        EVQLLESGGGLVQPGGSLRLSCAASGLTFSRYTMSWVRQAPGKGLEWVSAINSSGGS
412-14        EVQLLESGGGLVQPGGSLRLSCAASGLTFSRYGMSWVRQAPGKGLEWVSAINSSGGS
412-15        EVQLLESGGGLVQPGGSLRLSCAASGLTFSRYTMSWVRQAPGKGLEWVSAINSSGGS
412-16        EVQLLESGGGLVQPGGSLRLSCAASGLTFSRYGMSWVRQAPGKGLEWVSAINSSGGS
41L2-A1       EVQLLESGGGLVQPGGSLRLSCAASGLTFSRYGMSWVRQAPGKGLEWVSAITSSGGS
41L2-A2       EVQLLESGGGLVQPGGSLRLSCAASGLTFSRYGMSWVRQAPGKGLEWVSAITSSGGS
41L2-A3       EVQLLESGGGLVQPGGSLRLSCAASGLTFSRYGMSWVRQAPGKGLEWVSAITSSGGS
41L2-E3       EVQLLESGGGLVQPGGSLRLSCAASGLTFSRYGMSWVRQAPGKGLEWVSAITSSGGS
```

FIG. 10 continued

```
                                                                    SEQ
                                                 CDR3               ID
              60         70        80        90       100           NO:
41-1    TYYSDTVKGRFTISRDNSKNTLYLQMNSLRAEDTAVYYCARLPDYWGQGTLVTVSS    103
41-2    TYYSDTVKGRFTISRDNSKNTLYLQMNSLRAEDTAVYYCARLPDYWGQGTLVTVSS    104
41-3    TYYSDTVKGRFTISRDNSKNTLYLQMNSLRAEDTAVYYCARLPDYWGQGTLVTVSS    104
41-4    TYYSDTVKGRFTISRDNSKNTLYLQMNSLRAEDTAVYYCARLPDYWGQGTLVTVSS    103
41-5    TYYSDTVKGRFTISRDNSKNTLYLQMNSLRAEDTAVYYCARLPDYWGQGTLVTVSS    105
41-6    TYYSDTVKGRFTISRDNSKNTLYLQMNSLRAEDTAVYYCARLPDYWGQGTLVTVSS    103
41-8    TYYSDTVKGRFTISRDNSKNTLYLQMNSLRAEDTAVYYCARLPDYWGQGTLVTVSS    106
41-9    TYYSDTVKGRFTISRDNSKNTLYLQMNSLRAEDTAVYYCARLPDYWGQGTLVTVSS    104
41-10   TYYSDTVKGRFTISRDNSKNTLYLQMNSLRAEDTAVYYCARLPDYWGQGTLVTVSS    107
41-11   TYYSDTVKGRFTISRDNSKNTLYLQMNSLRAEDTAVYYCARLPDYWGQGTLVTVSS    104
41-12   TYYSDTVKGRFTISRDNSKNTLYLQMNSLRAEDTAVYYCARLPDYWGQGTLVTVSS    108
41-13   TYYSDTVKGRFTISRDNSKNTLYLQMNSLRAEDTAVYYCARLPDYWGQGTLVTVSS    109
41-14   TYYSDTVKGRFTISRDNSKNTLYLQMNSLRAEDTAVYYCARLPDYWGQGTLVTVSS    103
41-16   TYYSDTVKGRFTISRDNSKNTLYLQMNSLRAEDTAVYYCARLPDYWGQGTLVTVSS    110
41-17   TYYSDTVKGRFTISRDNSKNTLYLQMNSLRAEDTAVYYCARLPDYWGQGTLVTVSS    111
41-18   TYYSDTVKGRFTISRDNSKNTLYLQMNSLRAEDTAVYYCARLPDYWGQGTLVTVSS    112
41-19   TYYSDTVKGRFTISRDNSKNTLYLQMNSLRAEDTAVYYCARLPDYWGQGTLVTVSS    103
41-20   TYYSDTVKGRFTISRDNSKNTLYLQMNSLRAEDTAVYYCARLPDYWGQGTLVTVSS    113
411-1   TYYADSVKGRFTISRDNSKNTLYLQMNSLRAEDTAVYYCARLPDYWGQGTLVTVSS    114
411-2   TYYSDTVKGRFTISRDNSKNTLYLQMNSLRAEDTAVYYCARLPDYWGQGTLVTVSS    103
411-4   TYYSDTVKGRFTISRDNSKNTLYLQMNSLRAEDTAVYYCARLPDYWGQGTLVTVSS    108
411-5   TYYSDTVKGRFTISRDNSKNTLYLQMNSLRAEDTAVYYCARLPDYWGQGTLVTVSS    104
411-6   TYYSDTVKGRFTISRDNSKNTLYLQMNSLRAEDTAVYYCARLPDYWGQGTLVTVSS    115
411-7   TYYSDTVKGRFTISRDNSKNTLYLQMNSLRAEDTAVYYCARLPDYWGQGTLVTVSS    116
411-10  TYYSDTVKGRFTISRDNSKNTLYLQMNSLRAEDTAVYYCARLPDYWGQGTLVTVSS    103
411-11  TYYSDTVKGRFTISRDNSKNTLYLQMNSLRAEDTAVYYCARLPDYWGQGTLVTVSS    117
411-12  TYYSDTVKGRFTISRDNSKNTLYLQMNSLRAEDTAVYYCARLPDYWGQGTLVTVSS    112
411-13  TYYSDTVKGRFTISRDNSKNTLYLQMNSLRAEDTAVYYCARLPDYWGQGTLVTVSS    118
411-14  TYYSDTVKGRFTISRDNSKNTLYLQMNSLRAEDTAVYYCARLPDYWGQGTLVTVSS    119
411-16  TYYSDTVKGRFTISRDNSKNTLYLQMNSLRAEDTAVYYCARLPDYWGQGTLVTVSS    103
412-1   TYYSDTVKGRFTISRDNSKNTLYLQMNSLRAEDTAVYYCARLPDYWGQGTLVTVSS    103
412-5   TYYSDTVKGRFTISRDNSKNTLYLQMNSLRAEDTAVYYCARLPDYWGQGTLVTVSS    103
412-6   TYYSDTVKGRFTISRDNSKNTLYLQMNSLRAEDTAVYYCARLPDYWGQGTLVTVSS    120
412-8   TYYSDTVKGRFTISRDNSKNTLYLQMNSLRAEDTAVYYCARLPDYWGQGTLVTVSS    121
412-9   TYYSDTVKGRFTISRDNSKNTLYLQMNSLRAEDTAVYYCARLPDYWGQGTLVTVSS    122
412-13  TYYSDTVKGRFTISRDNSKNTLYLQMNSLRAEDTAVYYCARLPDYWGQGTLVTVSS    121
412-14  TYYSDTVKGRFTISRDNSKNTLYLQMNSLRAEDTAVYYCARLPDYWGQGTLVTVSS    103
412-15  TYYSDTVKGRFTISRDNSKNTLYLQMNSLRAEDTAVYYCARLPDYWGQGTLVTVSS    121
412-16  TYYSDTVKGRFTISRDNSKNTLYLQMNSLRAEDTAVYYCARLPDYWGQGTLVTVSS    103
41L2-A1 TYYSDTVKGRFTISRDNSKNTLYLQMNSLRAEDTAVYYCARLPDYWGQGTLVTVSS    120
41L2-A2 TYYSDTVKGRFTISRDNSKNTLYLQMNSLRAEDTAVYYCARLPDYWGQGTLVTVSS    120
41L2-A3 TYYSDTVKGRFTISRDNSKNTLYLQMNSLRAEDTAVYYCARLPDYWGQGTLVTVSS    120
41L2-E3 TYYSDTVKGRFTISRDNSKNTLYLQMNSLRAEDTAVYYCARLPDYWGQGTLVTVSS    120
```

FIG. 10 continued

```
                                                     CDR1                    CDR2
               1         10        20        30        40        50
    41L2-E9    EVQLLESGGGLVQPGGSLRLSCAASGLTFSRYGMSWVRQAPGKGLEWVSAITSSGGS
    41L3-F12   EVQLLESGGGLVQPGGSLRLSCAASGLTFSRYGMSWVRQAPGKGLEWVSAITSSGGS
    41L3-G2    EVQLLESGGGLVQPGGSLRLSCAASGLTFSRYGMSWVRQAPGKGLEWVSAITSSGGS
    41L2-G6    EVQLLESGGGLVQPGGSLRLSCAASGLTFSRYGMSWVRQAPGKGLEWVSAITSSGGS
    41H-A7     EVQLLESGGGLVQPGGSLRLSCAASGLTFSRYPMSWVRQAPGKGLEWVSAITSSGGS
    41H-B8     EVQLLESGGGLVQPGGSLRLSCAASGLNFSRYGMSWVRQAPGKGLEWVSAITSSGGS
    41H-D6     EVQLLESGGGLVQPGGSLRLSCAASGLTFSRYGMSWVRQAPGKGLEWVSAIKSSGGS
    41H-D11    EVQLLESGGGLVQPGGSLRLSCAASGLTFSRYGMSWVRQAPGKGLEWVSAIKSNGGS
    41H-E11    EVQLLESGGGLVQPGGSLRLSCAASGLTFSRYGMSWVRQAPGKGLEWVSRITSSGGS
    41H-E4     EVQLLESGGGLVQPGGSLRLSCAASGLTFSRYGMSWVRQAPGKGLEWVSHIKSSGGS
    41-E5      EVQLLESGGGLVQPGGSLRLSCAASGLTFSRYGMSWVRQAPGKGLEWVSAITSSGGS
    41H-E7     EVQLLESGGGLVQPGGSLRLSCAASGLTFSRYGMSWVRQAPGKGLEWVSAIKASGGS
    41H-E9     EVQLLESGGGLVQPGGSLRLSCAASGLTFSRYGMSWVRQAPGKGLEWVSAIKSSGSS
    41H-E12    EVQLLESGGGLVQPGGSLRLSCAASGLTFSRYGMSWVRQAPGKGLEWVSAIKSLGGS
    41H-F10    EVQLLESGGGLVQPGGSLRLSCAASGLTFSRYGMSWVRQAPGKGLEWVSAITSMGGS
    41H-F12    EVQLLESGGGLVQPGGSLRLSCAASGLTFSRYGMSWVRQAPGKGLEWVSAQTSSGGS
    41C1A2     EVQLLESGGGLVQPGGSLRLSCAASGLTFSRYPMSWVRQAPGKGLEWVSRITSSGGS
    41C1A4     EVQLLESGGGLVQPGGSLRLSCAASGLTFSRYPMSWVRQAPGKGLEWVSRITSSGGS
    41C1C1     EVQLLESGGGLVQPGGSLRLSCAASGLTFSRYPMSWVRQAPGKGLEWVSAIKSSGGS
    41C1E4     EVQLLESGGGLVQPGGSLRLSCAASGLTFSRYPMSWVRQAPGKGLEWVSAITSSGGS
    41C2A1     EVQLLESGGGLVQPGGSLRLSCAASGLTFSRYPMSWVRQAPGKGLEWVSAITSSGGS
    41C2A4     EVQLLESGGGLVQPGGSLRLSCAASGLTFSRYPMSWVRQAPGKGLEWVSAITSSGGS
    41C2E4     EVQLLESGGGLVQPGGSLRLSCAASGLTFSRYPMSWVRQAPGKGLEWVSAIKSSGGS
    41C2G8     EVQLLESGGGLVQPGGSLRLSCAASGLTFSRYPMSWVRQAPGKGLEWVSRITSSGGS
    3-74/C1A2  EVQLVESGGGLVQPGGSLRLSCAASGLTFSRYPMSWVRQAPGKGLVWVSRITSSGGS
    3-74/C1A4  EVQLVESGGGLVQPGGSLRLSCAASGLTFSRYPMSWVRQAPGKGLVWVSRITSSGGS
    3-74/C1E4  EVQLVESGGGLVQPGGSLRLSCAASGLTFSRYPMSWVRQAPGKGLVWVSAITSSGGS
    3-74/C2A4  EVQLVESGGGLVQPGGSLRLSCAASGLTFSRYPMSWVRQAPGKGLVWVSAITSSGGS
```

FIG. 10 continued

```
                                                                    SEQ
                                                          CDR3      ID
              60        70        80        90        100           NO:
41L2-E9    TYYSDTVKGRFTISRDNSKNTLYLQMNSLRAEDTAVYYCARLPDYWGQGTLVTVSS  120
41L3-F12   TYYSDTVKGRFTISRDNSKNTLYLQMNSLRAEDTAVYYCARLPDYWGQGTLVTVSS  120
41L3-G2    TYYSDTVKGRFTISRDNSKNTLYLQMNSLRAEDTAVYYCARLPDYWGQGTLVTVSS  120
41L2-G6    TYYSDTVKGRFTISRDNSKNTLYLQMNSLRAEDTAVYYCARLPDYWGQGTLVTVSS  120
41H-A7     TYYSDTVKGRFTISRDNSKNTLYLQMNSLRAEDTAVYYCARLPDYWGQGTLVTVSS  123
41H-B8     TYYSDTVKGRFTISRDNSKNTLYLQMNSLRAEDTAVYYCARLPDYWGQGTLVTVSS  124
41H-D6     TYYSDTVKGRFTISRDNSKNTLYLQMNSLRAEDTAVYYCARLPDYWGQGTLVTVSS  125
41H-D11    TYYSDTVKGRFTISRDNSKNTLYLQMNSLRAEDTAVYYCARLPDYWGQGTLVTVSS  126
41H-E11    TYYSDTVKGRFTISRDNSKNTLYLQMNSLRAEDTAVYYCARLPDYWGQGTLVTVSS  127
41H-E4     TYYSDTVKGRFTISRDNSKNTLYLQMNSLRAEDTAVYYCARLPDYWGQGTLVTVSS  128
41-E5      TKYSDTVKGRFTISRDNSKNTLYLQMNSLRAEDTAVYYCARLPDYWGQGTLVTVSS  129
41H-E7     TYYSDTVKGRFTISRDNSKNTLYLQMNSLRAEDTAVYYCARLPDYWGQGTLVTVSS  130
41H-E9     TYYSDTVKGRFTISRDNSKNTLYLQMNSLRAEDTAVYYCARLPDYWGQGTLVTVSS  131
41H-E12    TYYSDTVKGRFTISRDNSKNTLYLQMNSLRAEDTAVYYCARLPDYWGQGTLVTVSS  132
41H-F10    TYYSDTVKGRFTISRDNSKNTLYLQMNSLRAEDTAVYYCARLPDYWGQGTLVTVSS  133
41H-F12    TYYSDTVKGRFTISRDNSKNTLYLQMNSLRAEDTAVYYCARLPDYWGQGTLVTVSS  134
41C1A2     TYYSDTVKGRFTISRDNSKNTLYLQMNSLRAEDTAVYYCARLPDYWGQGTLVTVSS  135
41C1A4     TYYSDTVKGRFTISRDNSKNTLYLQMNSLRAEDTAVYYCARLPDYWGQGTLVTVSS  135
41C1C1     TYYSDTVKGRFTISRDNSKNTLYLQMNSLRAEDTAVYYCARLPDYWGQGTLVTVSS  136
41C1E4     TYYSDTVKGRFTISRDNSKNTLYLQMNSLRAEDTAVYYCARLPDYWGQGTLVTVSS  123
41C2A1     TYYSDTVKGRFTISRDNSKNTLYLQMNSLRAEDTAVYYCARLPDYWGQGTLVTVSS  123
41C2A4     TYYSDTVKGRFTISRDNSKNTLYLQMNSLRAEDTAVYYCARLPDYWGQGTLVTVSS  123
41C2E4     TYYSDTVKGRFTISRDNSKNTLYLQMNSLRAEDTAVYYCARLPDYWGQGTLVTVSS  136
41C2G8     TYYSDTVKGRFTISRDNSKNTLYLQMNSLRAEDTAVYYCARLPDYWGQGTLVTVSS  135
3-74/      TYYSDTVKGRFTISRDNAKNTLYLQMNSLRAEDTAVYYCARLPDYWGQGTLVTVSS  137
C1A2
3-74/      TYYSDTVKGRFTISRDNAKNTLYLQMNSLRAEDTAVYYCARLPDYWGQGTLVTVSS  137
C1A4
3-74/      TYYSDTVKGRFTISRDNAKNTLYLQMNSLRAEDTAVYYCARLPDYWGQGTLVTVSS  138
C1E4
3-74/      TYYSDTVKGRFTISRDNAKNTLYLQMNSLRAEDTAVYYCARLPDYWGQGTLVTVSS  138
C2A4

H-FR1      EVQLLESGGGLVQPGGSLRLSCAAS              SEQ ID NO: 148
H-FR1B     EVQLVESGGGLVQPGGSLRLSCAAS              SEQ ID NO: 149
H-FR2      WVRQAPGKGLEWVS                         SEQ ID NO: 150
H-FR2B     WVRQAPGKGLVWVS                         SEQ ID NO: 151
H-FR3      RFTISRDNSKNTLYLQMNSLRAEDTAVYYCAR       SEQ ID NO: 152
H-FR3B     RFTISRDNAKNTLYLQMNSLRAEDTAVYYCAR       SEQ ID NO: 153
H-FR4      WGQGTLVTVSS                            SEQ ID NO: 139
```

ANTI-MYOSTATIN ANTIBODIES

This application is a continuation of U.S. patent application Ser. No. 12/066,838, now U.S. Pat. No. 7,632,499, filed Mar. 14, 2008, which was a §371 national phase filing of International Application No. PCT/US2006/038817, filed Oct. 5, 2006, which claims the benefit of U.S. Provisional Application Ser. No. 60/725,738 filed Oct. 12, 2005, each of which is herein incorporated by reference in its entirety.

FIELD OF THE INVENTION

The invention is in the field of medicine, particularly in the field of monoclonal antibodies against myostatin. More specifically the invention relates to high affinity chimeric, humanized or human anti-myostatin antibodies and use of the antibodies for therapy, prophylaxis or diagnosis of various disorders or conditions in mammalian and avian species.

BACKGROUND OF THE INVENTION

Members of the transforming growth factor beta (TGF-β) superfamily of proteins are involved in embryonic development and adult tissue homeostasis. The TGF-β superfamily members share a common structure including a peptide signal sequence required for secretion of the protein and an amino-terminal fragment that is proteolytically cleaved about 105-140 amino acids from the carboxy-terminus of the large precursor protein to produce the mature protein. The mature protein is characterized by highly conserved cysteine residues, while the active form of the mature protein is a disulfide-linked homodimer of the proteolytically-cleaved proprotein (Gray, A., and Maston, A., *Science,* 247:1328, 1990).

Myostatin, also referred to as growth differentiation factor-8 (GDF-8) is a member of the TGF-β superfamily of proteins. Myostatin shares structural similarities with other TGF-β family members. It contains a hydrophobic amino-terminus that acts as a secretory signal and a conserved RSRR domain that is important for proteolytic processing. Cleavage of the protein gives rise to an amino-terminal latency associated peptide and a carboxy-terminal mature signaling peptide which forms the biologically active homodimer. Myostatin is expressed largely in developing and adult skeletal muscle and functions as a negative regulator of skeletal muscle. Systemic over-expression of myostatin in adult mice leads to muscle wasting (Zimmers, et al., *Science,* 296:1486-1488, 2002) while conversely, a myostatin knock-out mouse is characterized by hypertrophy and hyperplasia of the skeletal muscle resulting in two- to threefold greater muscle mass than their wild type littermates and a decrease in fat accumulation (McPherron, et al. *Nature,* 387:83-90, 1997). A human with a myostatin knock-out mutation was reported to be associated with gross muscle hypertrophy (Scheulke, et al., *New Eng. J. Med.* 350:2682, 2004).

There are presently limited treatments available for muscle wasting or for disorders or conditions which would benefit from an increase in muscle mass and/or muscle strength including, for example, muscular dystrophy, frailty, disuse atrophy and, cachexia, as well as disorders which are associated with muscle wasting, for example, renal disease, cardiac failure or disease, and liver disease. Due to its role as a negative regulator of skeletal muscle growth, myostatin is a desirable target for therapeutic or prophylactic intervention for such disorders or conditions or for monitoring progression of such disorders or conditions. Apart from its direct role in skeletal muscle regulation, myostatin may also be involved in other physiological processes including preadipocyte differentiation to adipocytes (Kim et al. *BBRC,* 281:902-906, 2001), and, indirectly with glucose homeostasis (McPherron, A and Lee S-J. *JCI* 109:595, 2002) and inhibition of bone formation (Hamrick, M. *Mol. Cell Evol. Biol.* 272 388-91, 2003; Hamrick et al. Calcif Tissue Int. 71:63, 2002). Therefore, myostatin-specific antagonists, e.g., myostatin-specific antibodies, may also prove useful for treating, preventing or monitoring disorders or conditions such as those which benefit from increasing bone density (e.g., osteoporosis), Type II diabetes, metabolic syndrome, obesity and osteoarthritis.

Myostatin is highly conserved across species; the amino acid sequence of the mature form of myostatin in human, mouse, rat, chicken, turkey and cow are 100% identical (See FIGS. 2 and 3). There are naturally occurring myostatin mutations in cattle, which have been linked to a double-muscled phenotype (McPherron, et al. *PNAS,* 94:12457-61, 1997). Since myostatin is highly conserved in sequence and in function across species, not only does an anti-myostatin antibody provide a promising means of increasing muscle mass, or treatment or prevention of such disorders or conditions listed above in humans, but also in other mammals including, e.g., domestic animals (e.g., canine and feline), sports animals (e.g., equine), food-source animals (e.g., bovine, porcine and ovine) and in avian species (e.g., chicken, turkey, duck and other game birds and poultry).

Growth differentiation factor-11, also referred to as GDF-11 or BMP-11, is the member of the TGF-β superfamily of proteins that is most homologous to myostatin. The amino acid sequence of the mature forms of human myostatin and GDF-11 are about 90% identical; however, GDF-11 is expressed in a wider range of tissues than is GDF-8 including dental pulp, brain, heart, kidney and lung as well as muscle and adipose tissue (Nakashima, et al. *Mech. of Development* 80:185, 1999). GDF-11 knock-out mice die within 24 hours of birth with multiple abnormalities. In particular the mice exhibit extra pairs of ribs, lack kidneys and show defects in the stomach, spleen and pancreas (McPherron et al., *Nature Genetics* 22:260, 1999; Esquela and Lee, *Dev. Biol.* 257:356, 2003; Harmon et al., *Devpt.* 131:6163, 2004). Human GDF-11 has recently been found to govern the temporal windows during which multipotent progenitors retain competence to produce distinct neural progeny (Kim, J. et al. *Science* 308: 1927-1930, 2005).

There is a therapeutic need for an anti-myostatin antibody that preferentially binds myostatin over other TGF-β superfamily proteins, particularly GDF-11. Furthermore, there is a need for myostatin-specific antibodies which bind myostatin with a high affinity, particularly a higher affinity (i.e. a stronger affinity as shown for example by a lower $K_D$ value), than with which they bind GDF-11, and thereby allow the dosage level that patients receive to be minimized which may thereby result in less frequent dosing with such an antibody than with an antibody that binds myostatin with a lesser affinity (i.e., a higher $K_D$). A high affinity antibody is also desirable in that it may allow for more flexibility in the route of administration of the antibody to a patient since it is less desirable for a drug to be administered intravenously than subcutaneously for example. There is also a need for myostatin-specific antibodies with a low or otherwise favorable $IC_{50}$ value in a myostatin bioactivity assay in order to generate a therapeutic anti-myostatin antibody with a minimum effective therapeutic dose. It is also desirable to provide antibodies specific to myostatin where any immune response to the antibody evoked by a patient receiving the antibody is reduced to a minimum. The present invention satisfies these needs and provides related advantages.

SUMMARY OF THE INVENTION

Antibodies of the invention are chimeric, humanized, or fully human anti-myostatin monoclonal antibodies, and antigen-binding portions thereof, that antagonize or neutralize at least one in vitro or in vivo biological activity or property associated with myostatin or a portion thereof. Preferably, the antibodies of the invention do not bind a peptide consisting of amino acids 40-64 (inclusive), 43-57 or 45-59 of mature myostatin, preferably human myostatin, at levels significantly greater than background.

In one embodiment, antibodies of the invention have an $IC_{50}$ of less than or equal to about 40 nM, 30 nM, 25 nM, 20 nM or 10 nM, more preferably less than or equal to about 5 nM, 4 nM, 3 nM, 2 nM or 1 nM in an in vitro myostatin/SBE reporter assay (see Example 5). Preferably the antibodies of the invention have an $IC_{50}$ in an in vitro myostatin/SBE reporter assay at least 20% or 50% lower, more preferably at least about two times, three times or four times lower than the $IC_{50}$ of the antibody in an in vitro GDF-11/SBE reporter assay (as described in Example 5 herein).

In one embodiment, antibodies of the invention are characterized by a strong binding affinity ($K_D$) for myostatin, i.e., less than about $4.2 \times 10^{-9}$ M or $4.0 \times 10^{-9}$ M, preferably less than about $4.6 \times 10^{-10}$ M, $4.0 \times 10^{-10}$ or $2 \times 10^{-10}$ M and more preferably less than about $8 \times 10^{-11}$ M, $7 \times 10^{-11}$ M, $5 \times 10^{-12}$ M or $1.4 \times 10^{-12}$ M. Alternatively, the antibodies of the invention are characterized by a $K_D$ for myostatin of no greater than about $4.2 \times 10^{-9}$ M or $4.0 \times 10^{-9}$ M, preferably no greater than about $4.6 \times 10^{-10}$ M, $4.0 \times 10^{-10}$ M or $2 \times 10^{-10}$ M and more preferably no greater than about $8 \times 10^{-11}$ M, $7 \times 10^{-11}$ M, $5 \times 10^{-12}$ M or $1.4 \times 10^{-12}$ M.

In another embodiment, the anti-myostatin antibodies of the invention are characterized by preferentially binding myostatin over GDF-11 protein by at least 20%, 30%, or 40%. Preferably, antibodies of the invention that preferentially bind myostatin over GDF-11 are further characterized by having a $K_D$ for myostatin of less than about $4.2 \times 10^{-9}$ M or $4.0 \times 10^{-9}$ M, preferably less than about $4.6 \times 10^{-10}$ M, $4.0 \times 10^{-10}$ M or $2 \times 10^{-10}$ M and more preferably less than about $5 \times 10^{-12}$ M or $1.4 \times 10^{-12}$ M. In another embodiment, antibodies of the invention that preferentially bind myostatin over GDF-11 are further characterized by having an $IC_{50}$ of less than or equal to about 40 nM, 20 nM or 10 nM, more preferably less than or equal to about 5 nM, 4 nM, 3 nM, 2 nM or 1 nM in an in vitro myostatin/SBE reporter assay.

In another embodiment, an anti-myostatin monoclonal antibody of the invention comprises a light chain variable region ("LCVR") polypeptide with an amino acid sequence selected from the group consisting of SEQ ID NOs: 74-102, 140, 141 and 142 (FIG. 9). In another embodiment, an anti-myostatin monoclonal antibody of the invention comprises a heavy chain variable region ("HCVR") polypeptide with an amino acid sequence selected from the group consisting of SEQ ID NOs: 103-138 (FIG. 10).

In another embodiment, an anti-myostatin monoclonal antibody of the invention comprises (i) a LCVR polypeptide comprising an amino acid sequence selected from the group consisting of SEQ ID NOs: 74-102, 140, 141 and 142, and (ii) a HCVR polypeptide comprising an amino acid sequence selected from the group consisting of SEQ ID NOs: 103-138. In a preferred embodiment, an antibody of the invention comprising an LCVR polypeptide comprising an amino acid sequence with a SEQ ID NO as shown in Table 1 below further comprises a HCVR polypeptide comprising an amino acid sequence with the SEQ ID NO of the HCVR polypeptide corresponding to the particular LCVR in Table 1 below. For example, an antibody of the invention comprising an LCVR polypeptide comprising an amino acid sequence of SEQ ID NO: 88, preferably further comprises a HCVR polypeptide comprising an amino acid sequence of SEQ ID NO: 103 or 119.

TABLE 1

(Seq of preferred Abs of the invention)

| LCVR | HCVR (SEQ ID NOs) |
|---|---|
| 74 | 103 |
| 75 | 104 |
| 76 | 104 |
| 77 | 103 or 113 |
| 78 | 105 |
| 79 | 103 |
| 80 | 106 |
| 81 | 103, 104, 107, 108, 109, 110, 112, 114, 117, 118 |
| 82 | 104 |
| 83 | 111 |
| 84 | 112 |
| 85 | 113 |
| 86 | 103, 108, 115 |
| 87 | 116 |
| 88 | 103, 119 |
| 89 | 103, 120, 123, 124, 125, 126, 127, 128, 129, 130, 131, 132, 133, 134 |
| 90 | 103, 121, 122 |
| 91 | 121 |
| 92 | 103, 121 |
| 93 | 120 |
| 94 | 120 |
| 95 | 120, 137 |
| 96 | 120, 135 |
| 97 | 120 |
| 98 | 120, 138 |
| 99 | 120, 136, 138 |
| 100 | 120 |
| 101 | 135 |
| 102 | 136 |
| 140 | 137 |
| 141 | 123 |
| 142 | 138 |

In another embodiment, a monoclonal antibody of the invention is one which can compete for binding to human myostatin with a competing antibody as demonstrated by an assay available in the art (e.g., a competition ELISA), wherein the competing antibody comprises two polypeptides with the sequences selected from the group consisting of: (i) SEQ ID NOs: 98 and 138 and (ii) SEQ ID NOs: 74 and 103.

In one embodiment, an anti-myostatin antibody of the invention has a heavy chain variable region and a light chain variable region, wherein the heavy chain variable region comprises CDR regions with the following amino acid sequences: CDRH1 (SEQ ID NO: 42), CDRH2 (SEQ ID NO: 71) and CDRH3 (SEQ ID NO: 72) (see FIG. 7); and/or wherein the light chain variable region comprises CDR regions with the following amino acid sequences: CDRL1 (SEQ ID NO: 12), CDRL2 (SEQ ID NO: 154) and CDRL3 (SEQ ID NO: 37) (see FIG. 6). Preferably, the heavy chain CDRs of an antibody of the invention are together in one antibody as in an antibody shown in FIG. 7 and the light chain CDRs of an antibody of the invention are together in one antibody as in an antibody shown in FIG. 6.

An anti-myostatin monoclonal antibody of the invention may further comprise a heavy chain constant region selected from the group consisting of human (or substantially of human origin) $IgG_1$, $IgG_2$, $IgG_3$, $IgG_4$, IgA, IgE, IgM and IgD, preferably $IgG_1$ or $IgG_4$. An anti-myostatin monoclonal antibody of the invention may further comprise a human kappa or lambda light chain constant region. When the antibody is to be used as a therapeutic or preventative in a human, the constant region is preferably substantially or entirely of human origin. When the antibody is to be used as a therapeutic or preventative in a non-human animal, or egg of a non-human animal, the constant region preferably substantially originates from the animal in which the antibody is to be used as a therapeutic. (see, e.g., Clarkson, C. et al., *Mol. Imm.* 30:1195-1204, 1993; U.S. application number 2002/01651350; and Genbank accession numbers X69797, U03778, X16701, X07174, AB016711).

Various forms of the antibody are contemplated herein. For example, an anti-myostatin monoclonal antibody of the invention may comprise or consist of an intact antibody (i.e., full-length, having an intact Fc region), a substantially intact antibody, an antigen-binding portion thereof (e.g., a Fab, Fab', $F(ab')_2$) or a single chain Fv fragment. It is understood that all such forms of the antibodies are encompassed herein and throughout within the term "antibody." Furthermore, an antibody of the invention may be labeled with a detectable label, immobilized on a solid phase and/or conjugated with a heterologous compound, e.g., an enzyme or polyethylene glycol molecule. Furthermore, antibodies of the invention are contemplated to be of monoclonal origin even though they may differ in glycosylation pattern.

In another embodiment, the invention provides a pharmaceutical composition comprising an anti-myostatin monoclonal antibody of the invention. The pharmaceutical composition of the invention may further comprise a pharmaceutically acceptable carrier. In said pharmaceutical composition, the anti-myostatin monoclonal antibody of the invention is the active ingredient. Preferably the pharmaceutical composition comprises a homogeneous or substantially homogeneous population of an anti-myostatin monoclonal antibody of the invention. The composition for therapeutic use is sterile and may be lyophilized, optionally supplied with an appropriate diluent.

The invention provides a method of inhibiting at least one myostatin biological activity in an animal, preferably a mammalian or avian species, preferably a human, in need thereof, comprising administering a therapeutically effective amount, or prophylactically effective amount, or myostatin-neutralizing or myostatin-inhibiting amount of an anti-myostatin monoclonal antibody of the invention to said mammalian or avian species. The invention further provides a method of enhancing muscle mass or treating or preventing a disease or disorder or condition ameliorated by neutralizing or antagonizing a myostatin bioactivity that comprises administering to a patient (e.g., a human) in need of such treatment or prevention a therapeutically or prophylactically effective amount of a monoclonal antibody of the invention.

The invention embodies an anti-myostatin monoclonal antibody of the invention for use in the manufacture of a medicament for administration to a mammal, preferably a human, for the treatment of e.g., frailty, cachexia, age-related sarcopenia, muscle wasting or weakness, myopathy, muscular dystrophy, osteoporosis, obesity, COPD, renal failure or disease, liver failure or disease, cardiac failure or disease, metabolic syndrome and Type II diabetes in a mammal, preferably a human, in need thereof by administering to said mammal a therapeutically effective or prophylactically effective amount of an anti-myostatin monoclonal antibody of the invention.

The invention embodies an article of manufacture comprising a packaging material and an antibody of the invention contained within said packaging material and wherein the packaging material comprises a package insert which indicates that the antibody neutralizes a myostatin activity or decreases the level of myostatin present in the system.

The invention further provides isolated nucleic acid encoding an antibody of the invention; a vector (or vectors) comprising that nucleic acid, optionally operably linked to control sequences recognized by a host cell transformed with the vector; a host cell comprising that vector; a process for producing an antibody of the invention comprising culturing the host cell so that the nucleic acid is expressed and, optionally, recovering the antibody from the host cell culture medium.

BRIEF DESCRIPTION OF THE DRAWINGS

FIG. 1 shows the amino acid sequence of human promyostatin with the signal sequence underlined and the portion of the protein at the carboxy-terminus that makes up a monomer of the mature form of myostatin in bold letters.

FIG. 2 shows the amino acid sequence of the monomeric human mature myostatin. Active human myostatin is a homodimer of this polypeptide associated by disulfide bonds. This sequence is identical to that of the mature myostatin in mouse, rat, chicken, turkey, dog, horse, and pig.

FIG. 3 shows an alignment of the amino acid sequence of mature myostatin of various mammalian and avian species.

FIG. 4 shows the alignment of the amino acid sequence of the mature form of human myostatin and human GDF-11.

FIG. 5 shows the amino acid sequence of the HCVR and LCVR of YN41 antibody, an exemplary parent antibody of antibodies of the invention. The figure further shows an exemplary nucleotide sequence encoding the HCVR and LCVR of YN41 antibody.

FIG. 6 shows the amino acid sequence of CDRs of the LCVR of various antibodies of the invention.

FIG. 7 shows the amino acid sequence of CDRs of the HCVR of various antibodies of the invention.

FIG. 8 shows the amino acid sequence of the light chain kappa constant region which may be operably linked to the LCVR of an antibody of the invention in the generation of a full-length light chain of an antibody of the invention and the amino acid sequence of an IgG4 constant region domain which may be operably linked to the HCVR of an antibody of the invention in the generation of a full-length heavy chain of an antibody of the invention. The figure further shows an exemplary nucleotide sequence encoding the light chain kappa constant region and an exemplary nucleotide sequence encoding a heavy chain IgG4 domain.

FIG. 9 shows the alignment of the amino acid sequence of LCVRs of various antibodies of the invention. The CDR domains are underlined in the first antibody sequence.

FIG. 10 shows the alignment of the amino acid sequence of HCVRs of various antibodies of the invention. The CDR domains are underlined in the first antibody sequence.

DETAILED DESCRIPTION OF THE INVENTION

The invention presents chimeric, humanized or fully human anti-myostatin monoclonal antibodies antibodies or antigen-binding portions thereof able to neutralize or antagonize at least one myostatin activity in vitro and/or in vivo further characterized as demonstrating an $IC_{50}$ less than about 40 nM, 20 nM or 10 nM, more preferably less than or equal to about 5 nM, 4 nM, 3 nM, 2 nM or 1 nM in an in vitro myostatin/SBE reporter assay and/or preferably demonstrating a strong binding affinity with myostatin. The antibodies of the invention are further characterized in that they preferentially bind myostatin over myostatin's nearest homologue, GDF-11 by at least 20%.

Definitions

When used herein, the term "mature myostatin" (see SEQ ID NO: 2 for human, murine, rat, chicken, turkey, canine, equine and porcine species) refers to the monomeric or the homodimeric form of the protein resulting after proteolytic cleavage at Arg 266 of the 375 amino acid proprotein form of myostatin. When used herein, the term "myostatin" refers to mature myostatin. When used herein, the term "promyostatin" or "proprotein form of myostatin" when used with reference to the human protein refers to a protein comprising the sequence shown in SEQ ID NO: 1 either as a monomer or homodimer.

A full-length antibody as it exists naturally is an immunoglobulin molecule comprised of four peptide chains, two heavy (H) chains (about 50-70 kDa when full length) and two light (L) chains (about 25 kDa when full length) interconnected by disulfide bonds. The amino terminal portion of each chain includes a variable region of about 100-110 or more amino acids primarily responsible for antigen recognition. The carboxy-terminal portion of each chain defines a constant region primarily responsible for effector function.

Light chains are classified as kappa or lambda and characterized by a particular constant region as known in the art. Heavy chains are classified as gamma, mu, alpha, delta, or epsilon, and define the antibody's isotype as IgG, IgM, IgA, IgD, and IgE, respectively and several of these may be further divided into subclasses (isotypes) e.g., $IgG_1$, $IgG_2$, $IgG_3$, $IgG_4$, $IgA_1$, and $IgA_2$. Each heavy chain type is characterized by a particular constant region known in the art. The subunit structures and three-dimensional configurations of different classes of antibodies are well known in the art. Each heavy chain is comprised of an N-terminal heavy chain variable region (herein "HCVR") and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (herein "LCVR") and a light chain constant region, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. Herein the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues which form specific interactions with the antigen. CDR3 is typically the greatest source of molecular diversity within the antibody-binding site. Assignment of amino acids to each domain is in accordance with well-known conventions [e.g., Kabat, "Sequences of Proteins of Immunological Interest," National Institutes of Health, Bethesda, Md. (1991) or Chothia numbering scheme as described in Al-Lazikani et al., *J. Mol. Biol.* 273:927-948, 1997, see also the internet site http:www.rubic.rdg.ac.uk/~andrew/bioinf.org/abs. The functional ability of an antibody to bind a particular antigen is largely influenced by the six CDRs.

The term "antibody," in reference to an anti-myostatin monoclonal antibody of the invention (or simply, "monoclonal antibody of the invention"), as used herein, refers to a monoclonal antibody. A "monoclonal antibody" as used herein refers to a chimeric antibody, a humanized antibody or a fully human antibody, unless otherwise indicated herein. Preferably a monoclonal antibody of the invention exists in a homogeneous or substantially homogeneous population. Monoclonal antibodies of the invention can be produced using e.g., hybridoma techniques well known in the art, as well as recombinant technologies, phage display technologies, synthetic-technologies or combinations of such technologies or other technologies readily known in the art. "Monoclonal antibody" refers to an antibody that is derived from a single copy or clone, including e.g., any eukaryotic, prokaryotic, or phage clone, and not the method by which it is produced. A "monoclonal antibody" can be an intact antibody (comprising a complete or full length Fc region), a substantially intact antibody, or a portion or fragment of an antibody comprising an antigen-binding portion, e.g., a Fab fragment, Fab' fragment or $F(ab')_2$ fragment of a chimeric, humanized or human antibody.

The variable regions of each light/heavy chain pair form the antigen-binding sites of the antibody. Thus, an intact IgG antibody has two binding sites. Except in bifunctional or bispecific antibodies, the two binding sites are the same. As used herein, the "antigen-binding portion" or "antigen-binding region" or "antigen-binding fragment" refers interchangeably herein to that portion of an antibody molecule, within the variable region, which contains the amino acid residues that interact with an antigen and confer on the antibody its specificity and affinity for the antigen. This antibody portion includes the framework amino acid residues necessary to maintain the proper conformation of the antigen-binding residues. Preferably, the CDRs of the antigen-binding region of the antibodies of the invention will be of murine origin or substantially of murine origin with certain amino acids residues altered to improve a particular activity (see e.g., FIGS. 6 and 7). Preferably, the framework regions of antibodies of the invention are of human origin or substantially of human origin (at least 95%, 97% or 99% of human origin; see e.g., FIGS. 9 and 10). In other embodiments, the antigen-binding region, or the CDRs of the antigen-binding region, can be derived from other non-human species including, but not limited to, rabbit, rat or hamster. In other embodiments, the antigen-binding region can be entirely of human origin or substantially of human origin with certain amino acids residues altered to improve a particular activity, e.g., affinity or specificity (see e.g., the amino acid positions of FIGS. 6 and 7 which are in bold print and underlined).

Furthermore, a "monoclonal antibody" as used herein can be a single chain Fv fragment that may be produced by joining the DNA encoding the LCVR and HCVR with a linker sequence. (See, Pluckthun, *The Pharmacology of Monoclonal Antibodies*, vol. 113, Rosenburg and Moore eds., Springer-Verlag, New York, pp 269-315, 1994). It is understood that regardless of whether fragments or portions are specified, the term "antibody" as used herein includes such fragments or portions as well as single chain forms. As long as the protein retains the ability to specifically or preferentially bind its intended target (i.e., epitope or antigen), it is included within the term "antibody."

A "population of monoclonal antibodies," refers to a homogeneous or substantially homogeneous antibody population (i.e., at least about 90%, 91%, 92%, 93%, 94%, 95%, 96%, more preferably at least about 97% or 98% or most preferably at least 99% of the antibodies in the population would compete in an ELISA assay for the same antigen or epitope). Antibodies may or may not be glycosylated and still fall within the bounds of the invention. Monoclonal antibodies may be homogeneous if they have identical amino acid seqeuence although they may differ in a post-translational modification, e.g., glycosylation pattern.

A "variant" anti-myostatin antibody, refers herein to a molecule which differs in amino acid sequence from a "parent" anti-myostatin antibody amino acid sequence by virtue of addition, deletion and/or substitution of one or more amino acid residue(s) in the parent antibody sequence. In the preferred embodiment, the variant comprises one or more amino acid substitution(s) in one or more CDR region(s) of the parent antibody. For example, the variant may comprise at least one (e.g., from about one to about ten, and preferably from about two to about five) substitution in one or more CDR regions of the parent antibody. Identity or homology with respect to the variant sequence is defined herein as the percentage of amino acid residues in the variant sequence that are identical with the parent antibody residues, after aligning the sequences and introducing gaps, if necessary, to achieve the maximum percent sequence identity. None of N-terminal, C-terminal, or internal extensions, deletions or insertions in the antibody sequence shall be construed as affecting sequence identity or homology. The variant retains the ability to bind myostatin and preferably has properties which are superior to those of the parent antibody. For example, the variant may have stronger binding affinity, lower IC50 in a SBE/reporter assay or enhanced ability to inhibit a myostatin bioactivity. The variant antibody of particular interest herein is one which displays at least about 5 fold, preferably at least about 10 fold, and more preferably at least about 20, 30, or 50 fold enhancement in a biological activity when compared to the parent antibody.

The "parent" antibody herein is one which is encoded by an amino acid sequence used for the preparation of the variant. The parent antibody may have a murine framework, but preferably has a human framework region. The parent antibody may be a murine (see e.g., Figs x herein), chimeric, humanized or human antibody.

The term "specifically binds" as used herein refers to the situation in which one member of a specific binding pair does not significantly bind to molecules other than its specific binding partner(s) as measured by a technique available in the art, e.g., competition ELISA, BIACORE assay or KINEXA assay. The term is also applicable where e.g., an antigen-binding domain of an antibody of the invention is specific for a particular epitope that is carried by a number of antigens, in which case the specific antibody carrying the antigen-binding domain will be able to specifically bind to the various antigens carrying the epitope. Accordingly a monoclonal antibody of the present invention specifically binds GDF-8 and GDF-11.

The term "preferentially binds" as used herein refers to the situation in which an antibody binds a specific antigen at least about 20% greater than it binds a different antigen as measured by a technique available in the art, e.g., competition ELISA or $K_D$ measurement with BIACORE or KINEXA assay. Accordingly, a monoclonal antibody of the present invention preferentially binds GDF-8 over GDF-11. Similarly, an antibody may preferentially may bind one epitope within an antigen over a different epitope within the same antigen.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. By "inhibiting epitope" and/or "neutralizing epitope" is intended an epitope, which when in the context of the intact molecule (in this case, myostatin) and when bound by antibody specific to the epitope, results in loss or diminution of a biological activity of the molecule or organism containing the molecule, in vivo or in vitro.

The term "epitope," as used herein, further refers to a portion of a polypeptide having antigenic and/or immunogenic activity in an animal, preferably a mammal, e.g., a mouse or a human. The term "antigenic epitope," as used herein, is defined as a portion of a polypeptide to which an antibody can specifically bind as determined by any method well known in the art, for example, by conventional immunoassays. Antigenic epitopes need not necessarily be immunogenic, but may be immunogenic. An "immunogenic epitope," as used herein, is defined as a portion of a polypeptide that elicits an antibody response in an animal, as determined by any method known in the art. (See, e.g., Geysen et al., *Proc. Natl. Acad. Sci. USA* 81:3998-4002 (1983)).

The phrases "biological property" or "bioactivity," "activity" or "biological activity," in reference to an antibody of the present invention, are used interchangeably herein and include, but are not limited to, epitope/antigen affinity and specificity, ability to neutralize or antagonize an activity of myostatin in vivo or in vitro, $IC_{50}$ in a myostatin/SBE reporter assay or other in vitro activity assay, the in vivo stability of the antibody and the immunogenic properties of the antibody. Other identifiable biological properties of an antibody include, for example, cross-reactivity, (i.e., with non-human homologs of the targeted peptide, or with other proteins or tissues, generally), and ability to preserve high expression levels of protein in mammalian cells. The aforementioned properties or characteristics can be observed or measured or assessed using art-recognized techniques including, but not limited to, ELISA, competitive ELISA, surface plasmon resonance analysis, in vitro and in vivo neutralization assays without limit, receptor binding, cytokine or growth factor production and/or secretion, Xenopus animal cap development, signal transduction and immunohistochemistry with tissue sections from different sources including human, primate, or any other source as the need may be.

The term "myostatin activity" as used herein refers to one or more of physiologically growth-regulatory or morphogenetic activities associated with active myostatin protein. For example, active myostatin is a negative regulator of skeletal muscle mass. Active myostatin can also modulate the production of muscle-specific enzymes (e.g., creatine kinase), stimulate myoblast proliferation, and modulate preadipocyte differentiation to adipocytes.

The term "inhibit" or "neutralize" as used herein with respect to an activity of an antibody of the invention means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher.

The term "isolated" when used in relation to a nucleic acid or protein (e.g., an antibody) refers to a nucleic acid-sequence or protein that is identified and separated from at least one contaminant with which it is ordinarily associated in its natural source. Preferably, an "isolated antibody" is an antibody that is substantially free of other antibodies having different antigenic specificities (e.g., pharmaceutical compositions of the invention comprise an isolated antibody that specifically binds myostatin and is substantially free of antibodies that specifically bind antigens other than myostatin).

The terms "Kabat numbering" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)).

A polynucleotide is "operably linked" when it is placed into a functional relationship with another polynucleotide. For example, a promoter or enhancer is operably linked to a coding sequence if it affects the transcription of the sequence. A peptide is "operably linked" to another peptide when the polynucleotides encoding them are operably linked, preferably they are in the same open reading frame.

The terms "individual," "subject," and "patient," used interchangeably herein, refer to an animal, preferably a mammalian (including a nonprimate and a primate) or avian species, including, but not limited to, murines, simians, humans, mammalian farm animals (e.g., bovine, porcine, ovine), mammalian sport animals (e.g., equine), and mammalian pets (e.g., canine and feline); preferably the term refers to humans. The term also refers to avian species, including, but not limited to, chickens and turkeys. In a certain embodiment, the subject, preferably a mammal, preferably a human, is further characterized with a disease or disorder or condition that would benefit from a decreased level or decreased bioactivity of myostatin. In another embodiment the subject, preferably a mammal, preferably a human, is further characterized as being at risk of developing a disorder, disease or condition that would benefit from a decreased level of myostatin or a decreased bioactivity of myostatin.

The term "vector" includes a nucleic acid molecule capable of transporting another nucleic acid to which it has been linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably linked. Such vectors are referred to herein as "recombinant expression vectors" (or simply "expression vectors") and exemplary vectors are well known in the art.

As used herein, the expressions "cell," "host cell," "cell line," and "cell culture" are used interchangeably and include an individual cell or cell culture that is a recipient of any isolated polynucleotide of the invention or any recombinant vector(s) comprising a sequence encoding a HCVR, LCVR or monoclonal antibody of the invention. Host cells include progeny of a single host cell, and the progeny may not necessarily be completely identical (in morphology or in total DNA complement) to the original parent cell due to natural, accidental, or deliberate mutation and/or change. A host cell includes cells transformed, transduced or infected in vivo or in vitro with one or more a recombinant vectors or a polynucleotide expressing a monoclonal antibody of the invention or a light chain or heavy chain thereof. A host cell which comprises a recombinant vector of the invention (either stably incorporated into the host chromosome or not) may also be referred to as a "recombinant host cell". Preferred host cells for use in the invention are CHO cells (e.g., ATCC CRL-9096), NS0 cells, SP2/0 cells and COS cells (ATCC e.g., CRL-1650, CRL-1651), HeLa (ATCC CCL-2). Additional host cells for use in the invention include plant cells, yeast cells, other mammalian cells and prokaryotic cells.

Antibody Characterization

The present invention relates to isolated, monoclonal antibodies that specifically bind myostatin with high affinity. The antibodies of the invention are preferably chimeric, humanized or human antibodies or antigen-binding portions thereof. Furthermore, antibodies of the invention neutralize or antagonize a myostatin biological activity in vivo or in vitro. Specific binding of anti-myostatin monoclonal antibodies of the invention to myostatin allows the antibodies of the invention to be used as therapeutics or prophylactics for myostatin-associated conditions, diseases or disorders, i.e., conditions, diseases or disorders which benefit from lowering myostatin levels or antagonizing or inhibiting a myostatin biological activity.

In a preferred embodiment, the invention provides an anti-myostatin monoclonal antibody that binds myostatin or a portion thereof with a binding affinity ($K_D$) for myostatin of less than about $4.2 \times 10^{-9}$ M or $4.0 \times 10^{-9}$ M, preferably less than about $4.6 \times 10^{-10}$ M, $4.0 \times 10^{-10}$ M or $2 \times 10^{-10}$ M and more preferably less than about $8 \times 10^{-11}$ M, $7 \times 10^{-11}$ M, $5 \times 10^{-12}$ M or $1.4 \times 10^{-12}$ M. Alternatively, the antibodies of the invention are characterized by a $K_D$ for myostatin of no greater than about $4.2 \times 10^{-9}$ M or $4.0 \times 10^{-9}$ M, preferably no greater than about $4.6 \times 10^{-10}$ M, $4.0 \times 10^{-10}$ M or $2 \times 10^{-10}$ M and more preferably no greater than about $8 \times 10^{-11}$ M, $7 \times 10^{-11}$ M, $5 \times 10^{-12}$ M or $1.4 \times 10^{-12}$ M. Antibody affinities may be determined as described in the examples hereinbelow.

Preferably, such antibodies of the invention characterized by a strong binding affinity as described herein also have an $IC_{50}$ of less than 40 nM, 30 nM, 25 nM, 20 nM or 10 nM, more preferably less than or equal to about 5 nM, 4 nM, 3 nM, 2 nM or 1 nM in an in vitro myostatin/SBE reporter assay. Even more preferably, the antibodies characterized by a strong binding affinity as described herein have an $IC_{50}$ in an in vitro myostatin/SBE reporter assay at least 20% lower, more preferably at least about two times, three times or four times lower than the $IC_{50}$ of the antibody in an in vitro GDF-11/SBE reporter assay (as described in Example 5 herein). Preferably, such antibodies of the invention characterized by a strong binding affinity as described herein are further characterized in that they preferentially react with GDF-8 over GDF-11 by at least 20% as measured by a technique in the art e.g., by competition ELISA, or by BIACORE or KINEXA assay to demonstrate at least 20% higher affinity (i.e., lower $K_D$) of the antibody to GDF-8 than GDF-11. Preferably, such antibodies of the invention characterized by a strong binding affinity as described herein are further characterized in that they do not bind a peptide consisting of amino acids 40-64 (inclusive), 43-57 or 45-59 of mature myostatin, preferably human myostatin.

In another preferred embodiment, the invention provides an anti-myostatin monoclonal antibody that has an $IC_{50}$ of less than or equal to about 40 nM, 30 nM, 25 nM, 20 nM or 10 nM, more preferably less than or equal to about 5 nM, 4 nM, 3 nM, 2 nM or 1 nM in an in vitro myostatin/SBE reporter assay. Even more preferably, the anti-myostatin monoclonal antibody's $IC_{50}$ in an in vitro myostatin/SBE reporter assay is at least about two times, three times or four times lower than the $IC_{50}$ of the antibody in an in vitro GDF-11/SBE reporter assay (as described in Example 5 herein). Antibodies of the invention with an $IC_{50}$ as described above may be further characterized by a $K_D$ for myostatin of less than about $4.2 \times 10^{-9}$ M or $4.0 \times 10^{-9}$ M, preferably less than about $4.6 \times 10^{-10}$ M, $4.0 \times 10^{-10}$ M or $2 \times 10^{-10}$ M and more preferably less than about $8 \times 10^{-11}$ M, $7 \times 10^{-11}$ M, $5 \times 10^{-12}$ M or $1.4 \times 10^{-12}$ M; alternatively, a $K_D$ for myostatin of no greater than about $4.2 \times 10^{-9}$ M or $4.0 \times 10^{-9}$ M, preferably no greater than about $4.6 \times 10^{-10}$ M, $4.0 \times 10^{-10}$ M or $2 \times 10^{-10}$ M and more preferably no greater than about $8 \times 10^{-11}$ M, $7 \times 10^{-11}$ M, $5 \times 10^{-12}$ M or $1.4 \times 10^{-12}$ M, which $K_D$ for myostatin is at least about 20% lower than the antibody has for GDF-11. Antibodies of the invention with an $IC_{50}$ as described above may be further characterized by preferentially binding myostatin by at least about 20%, preferably at least about two-fold, three-fold or four-fold, when compared to their ability to bind GDF-11 using an art-available method, e.g., ELISA assay or competitive ELISA assay or a $K_D$ value measured e.g., with a BIACORE or KINEXA assay. Antibodies of the invention with an $IC_{50}$ as described above may be further characterized by not binding a peptide consisting of amino acids 40-64 (inclusive), 43-57 or 45-59 of mature myostatin, preferably human myostatin at levels significantly greater than background (e.g., in an ELISA assay).

Preferably the myostatin and GDF-11 polypeptides tested for preferential binding of an antibody of the invention are both homodimeric forms of the mature protein, preferably of mammalian or avian origin, even more preferably of human origin. However, the myostatin and GDF-11 polypeptides tested for preferential binding of an antibody of the invention may be the monomeric form of the mature protein or proprotein form.

Monoclonal antibodies may be made using the hybridoma method widely known in the art (see e.g., Kohler et al., Nature, 256:495, 1975) or may be made by recombinant DNA methods (e.g., as in U.S. Pat. No. 4,816,567). Generally, a hybridoma can be produced by fusing a suitable immortal cell line (e.g., a myeloma cell line such as SP2/0) with antibody producing cells of the immunized animal. The antibody producing cell, preferably those of the spleen or lymph nodes, are obtained from animals immunized with the antigen of interest. The fused cells (hybridomas) can be isolated using selective culture conditions, and cloned by limiting dilution. Culture medium in which hybridoma cells are growing is assayed for production of monoclonal antibodies directed against the antigen. Preferably, the binding specificity of mabs produced by hybridoma cells is determined by immunoprecipitation or by an in vitro binding assay, such as radioimmunoassay (RIA) or ELISA. Cells which produce antibodies with the desired binding properties can be selected by a suitable screening assay. Methods for such isolation and screening are well known in the art.

Other suitable methods of producing or isolating antibodies of the invention can be used, including, for example, methods which select a recombinant antibody (e.g., single chain Fv or Fab) from a library, or which rely upon immunization of transgenic animals (e.g., mice) capable of producing a repertoire of human antibodies (see e.g., Jakobovits et al., Proc. Natl. Acad. Sci. USA, 90:2551-2555, 1993; Jakobovits et al., Nature, 362:255-258, 1993; Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. For example, nucleic acids encoding a chimeric or humanized chain can be expressed to produce a contiguous protein. See e.g., U.S. Pat. No. 4,816,567; European Patent No. 0,125,023 B1; U.S. Pat. No. 4,816,397; European Patent No. 0,120,694 B1; WO 86/01533; European Patent No. 0,194,276 B1; U.S. Pat. No. 5,225,539; European Patent No. 0,239,400 B1 and U.S. Pat. Nos. 5,585,089 and 5,698,762. See also, Newman, R. et al. BioTechnology, 10:1455-1460, 1993, regarding primatized antibody, and Ladner et al., U.S. Pat. No. 4,946,778 and Bird, R. E. et al., Science, 242:423-426, 1988, regarding single chain antibodies.

In addition, functional portions of antibodies, including antigen-binding portions of chimeric, humanized, human or single chain antibodies, can also be produced. Functional portions of the foregoing antibodies retain at least one antigen-binding function and/or biological function or bioactivity of the full-length antibody from which they are derived. Preferred functional portions retain an antigen-binding function of a corresponding full-length antibody (e.g., the ability to bind a mammalian mature form of myostatin). Particularly preferred functional portions or fragments retain the ability to inhibit one or more functions or bioactivities characteristic of a mammalian mature myostatin, such as a binding activity, a signaling activity, and/or stimulation of a cellular response. For example, in one embodiment, a functional portion or fragment can inhibit the interaction of mature myostatin with one or more of its ligands and/or can inhibit one or more receptor-mediated functions.

Antibody portions or fragments capable of binding to mature myostatin include, but are not limited to, Fv, Fab, Fab' and F(ab')$_2$ fragments and are encompassed by the invention. Such fragments can be produced by enzymatic cleavage or by recombinant techniques. For instance, papain or pepsin cleavage can generate Fab or F(ab')$_2$ fragments, respectively. The smallest antigen-binding fragment is the Fv, which consist of the HCVR and the LCVR domains. The Fab fragment consists of the HCVR-CH1 and LCVR-CL domains covalently linked by a disulfide bond between the constant regions. To overcome the tendency of non-covalently linked HCVR and LCVR domains in the Fv to dissociate when co-expressed in a host cell, a so-called single chain (sc) Fv fragment (scFv) can be constructed, in which a flexible and adequately long polypeptide links either the C-terminus of the HCVR to the N-terminus of LCVR or the C-terminus of the LCVR to the N-terminus of the HCVR. The most commonly used linker has been a 15-residue (Gly$_4$Ser)$_3$ peptide, but other linkers are also known in the art. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Selection of antibody fragments from libraries using enrichment technologies such as phage-display (Matthews D J and Wells J A. Science. 260:1113-7, 1993), ribosome display (Hanes, et al., Proc. Natl. Acad. Sci. (USA) 95:14130-5, 1998), bacterial display (Samuelson P., et al., Journal of Biotechnology. 96:129-54, 2002) or yeast display (Kieke M C, et al., Protein Engineering, 10:1303-10, 1997) has proven to be successful alternatives to classical hybridoma technology (recent reviews: Little M. et al., Immunology Today, 21:364-70, 2000;).

Variant Antibodies

A murine monoclonal antibody or a human antibody (produced e.g., in a transgenic mouse) raised against myostatin or against a protein comprising an immunogenic epitope of the invention is a parent antibody. A murine parent antibody may be further altered to create a chimeric or humanized form of the antibody using methods well known in the art. Such chimeric or humanized antibodies, may serve as parent antibodies for further variation or mutagenesis. Parent antibodies of the invention may be further mutagenized e.g., within the CDR domain(s) (see, e.g., FIGS. 6 and 7) to create a variant antibody with an optimized property of interest, e.g., binding affinity, IC$_{50}$, specificity, etc. An amino acid substitution variant antibody is preferred and has at least one amino acid residue of the parent antibody molecule removed and a different residue inserted in its place. The sites of greatest interest for substitutional mutagenesis include the CDR regions, but FR alterations are also contemplated. Conservative amino acid substitutions are preferred. If such substitutions result in a change in a biological activity of the antibody, then more substantial changes, i.e., non-conservative amino acid changes, may be introduced and the products screened.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity, specificity, IC$_{50}$) as herein disclosed. In order to identify candidate CDR region sites for modification, alanine scanning mutagens can be performed to identify CDR region residues contributing significantly to antigen binding. Alternatively, or in addition, it may be beneficial to analyze a crystal structure of the antigen-antibody complex to identify contact points between the antibody and myostatin. Such contact residues and neighboring residues are candidates for substitution according to the techniques elaborated herein or known in the art. Alternatively, or in addition, random mutagenesis may be performed on one or more CDR sequences at one or more residue positions, either while the CDR is operably linked to the variable region or while the CDR is independent of other variable region sequence and then the altered CDR returned to the variable region using recombinant DNA technology. Once such variant antibodies are generated the panel of variants is subjected to screening as described herein and antibodies with superior properties in one or more relevant assays may be selected for further development.

Any cysteine residue not involved in maintaining the proper conformation of an anti-myostatin antibody of the invention may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the parent antibody.

Glycosylation of antibodies is typically either N-linked or O-linked. N-linked refers to the attachment of the carbohydrate moiety to the side chain of an asparagines residue. The tripeptide sequence asparagines-X-serine and asparagines-X-threonine, where X is any amino acid except praline, are the recognition sequences for enzymatic attachment of the carbohydrate moiety to the asparagines side chain. Thus the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Sequence

A preferred monoclonal antibody of the invention comprises a LCVR comprising a peptide with a sequence selected from the group consisting of SEQ ID NOs: SEQ ID NOs: 74-102, 140, 141 and 142 (FIG. 9) and/or a HCVR comprising a peptide with a sequence selected from the group consisting of SEQ ID NOs: 103-138 (FIG. 10). In a preferred embodiment, an antibody of the invention comprising an LCVR polypeptide comprising an amino acid sequence with a SEQ ID NO as shown in Table 1 herein further comprises a HCVR polypeptide comprising an amino acid sequence with the SEQ ID NO of the HCVR polypeptide corresponding to the particular LCVR in Table 1. The skilled artisan will appreciate that the antibodies of the invention are not limited to the specific sequences of HCVR and LCVR as stated in FIGS. 9 and 10 herein, but also include variants of these sequences that retain antigen binding ability and other functional properties of the antibodies of the invention. Such variants may be derived from the provided sequences using techniques known in the art as described herein.

Furthermore, a monoclonal antibody of the invention is one that is competitively inhibited from binding mature human myostatin (or a portion thereof) by a competing monoclonal antibody comprising two polypeptides with the sequences selected from the group consisting of (i) SEQ ID NOs: 98 and 138 and (ii) SEQ ID NOs: 74 and 103. Such competitive inhibition between antibodies may be measured by assays readily known to one of skill in the art, e.g., a competition ELISA assay.

Preferably, an antibody of the invention which competes with the competing antibody defined above is further characterized by preferentially binding GDF-8 over GDF-11 by at least 20%, 30%, or 40% as measured by a technique in the art e.g., by competition ELISA, or by BIACORE or KINEXA assay to demonstrate at least 20%, 30% or 40% higher affinity (i.e., lower K$_D$) of the antibody to GDF-8 than GDF-11. Preferably an antibody of the invention which competes with the competing antibody defined above is further characterized by having a K$_D$ for myostatin of less than about $4.2 \times 10^{-9}$ M or $4.0 \times 10^{-9}$ M, preferably less than about $4.6 \times 10^{-10}$ M, $4.0 \times 10^{-10}$ M or $2 \times 10^{-10}$ M and more preferably less than about $8 \times 10^{-11}$ M, $7 \times 10^{-11}$ M, $5 \times 10^{-12}$ M or $1.4 \times 10^{-12}$ M; or alternatively is characterized by a K$_D$ for myostatin of no greater than about $4.2 \times 10^{-9}$ M or $4.0 \times 10^{-9}$ M, preferably no greater than about $4.6 \times 10^{-10}$ M, $4.0 \times 10^{-10}$ M or $2 \times 10^{-10}$ M and more preferably no greater than about $8 \times 10^{-11}$ M, $7 \times 10^{-11}$ M, $5 \times 10^{-12}$ M or $1.4 \times 10^{-12}$ M and/or is further characterized by having an IC$_{50}$ of less than or equal to about 40 nM, 20 nM or 10 nM, more preferably less than or equal to about 5 nM, 4 nM 3 nM, 2 nM or 1 nM in an in vitro myostatin/SBE reporter assay.

Even more preferably, an antibody of the invention which competes with the competing antibody defined above is further characterized by an IC$_{50}$ in an in vitro myostatin/SBE reporter assay that is less than or equal to about 40 nM, 30 nM, 25 nM, 20 nM or 10 nM, more preferably less than or equal to about 5 nM, 4 nM, 3 nM, 2 nM or 1 nM in an in vitro myostatin/SBE reporter assay. Even more preferably, the anti-myostatin monoclonal antibody's IC$_{50}$ in an in vitro myostatin/SBE reporter assay is at least about two times, three times or four times lower than the $IC_{50}$ of the antibody in an in vitro GDF-11/SBE reporter assay (as described in Example 5 herein). Even more preferably, an antibody of the invention which competes with the competing antibody defined above is further characterized by not binding a peptide consisting of amino acids 40-64 (inclusive), 43-57 or 45-59 of mature myostatin, preferably human myostatin.

In one embodiment, an anti-myostatin antibody of the invention has a heavy chain variable region and a light chain variable region, wherein the heavy chain variable region comprises CDR regions with the following amino acid sequences: CDRH1 (SEQ ID NO: 42), CDRH2 (SEQ ID NO: 71) and CDRH3 (SEQ ID NO: 72) (see FIG. 7); and/or wherein the light chain variable region comprises CDR regions with the following amino acid sequences: CDRL1 (SEQ ID NO: 12), CDRL2 (SEQ ID NO: 154) and CDRL3 (SEQ ID NO: 37). Preferably, the heavy chain CDRs of an antibody of the invention are as shown in FIG. 7 and the light chain CDRs of an antibody of the invention are as shown in FIG. 6.

It is further contemplated that an anti-myostatin antibody of the invention comprises a HCVR comprising a CDRH1 comprising a sequence selected from the group consisting of SEQ ID NOs: 38-41, and/or a CDRH2 comprising a sequence selected from the group consisting of SEQ ID NOs: 43-70 and 73, and/or a CDRH3 comprising the sequence of SEQ ID NO: 72. In another embodiment, an anti-myostatin antibody of the invention comprises a LCVR comprising a CDRL1 comprising a sequence selected from the group consisting of SEQ ID NOs: 9-11, and/or a CDRL2 comprising a sequence selected from the group consisting of SEQ ID NOs: 13-23, and/or a CDRL3 comprising a sequence selected from the group consisting of SEQ ID NOs: 24-36. In a preferred embodiment, an anti-myostatin antibody of the invention comprises a CDRH1 comprising a sequence selected from the group consisting of SEQ ID NOs: 38-42, and/or a CDRH2 comprising a sequence selected from the group consisting of SEQ ID NOs: 43-70 and 73, and/or a CDRH3 comprising the sequence of SEQ ID NO: 72 and further comprises a LCVR comprising a CDRL1 comprising a sequence selected from the group consisting of SEQ ID NOs: 9-11, and/or a CDRL2 comprising a sequence selected from the group consisting of SEQ ID NOs: 13-23, and/or a CDRL3 comprising a sequence selected from the group consisting of SEQ ID NOs: 24-36.

The structure comprising a CDR of the invention will generally be an antibody heavy or light chain sequence or a substantial portion thereof, in which the CDR is located at a location corresponding to the CDR of naturally occurring HCVR and LCVR (Kabat et al, Sequences of Proteins of Immunological Interest, US Dept of HHS, 1991). The three CDR regions for each chain, light and heavy, are provided in a framework region as a contiguous sequence represented by the following formula: FR1-CDR1-FR2-CDR2-FR3-CDR3-FR4. The heavy chain or light chain FR1, FR2, FR3 and FR4 combine to form the complete framework when arranged as a contiguous sequence with the CDRs in the order stated. Preferably the framework regions of an antibody of the invention are human, humanized or substantially of human origin.

In a humanized antibody for therapeutic use in humans, the framework sequence is preferably entirely or substantially of human origin (i.e., at least 90%, 92%, 95%, 96%, 97%, 98% or 99% of human origin). Preferably the light chain framework region of a humanized, human or chimeric antibody of the invention is as shown in FIG. 9, comprised of FR1 with SEQ ID NO: 143, FR2 with SEQ ID NO: 144, FR3 with SEQ ID NO: 145 and FR4 with SEQ ID NO: 146 or 147. Preferably the heavy chain framework region of a humanized, human or chimeric antibody of the invention is as shown in FIG. 10, comprised of FR1 with SEQ ID NO: 148 or 149, FR2 with SEQ ID NO: 150 or 151, FR3 with SEQ ID NO: 152 or 153, and FR4 with SEQ ID NO: 139. For example, antibody 3-74/C1E4 comprises a light chain variable region comprising FR1 with SEQ ID NO: 143, CDR1 with SEQ ID NO: 9, FR2 with SEQ ID NO: 144, CDR2 with SEQ ID NO: 18, FR3 with SEQ ID NO: 145, CDR3 with SEQ ID NO: 25 and FR4 with SEQ ID NO: 146. Antibody 3-74/C1E4 further comprises a heavy chain variable region comprising FR1 with SEQ ID NO: 149, CDR1 with SEQ ID NO: 40, FR2 with SEQ ID NO: 151, CDR2 with SEQ ID NO: 60, FR3 with SEQ ID NO: 153, CDR3 with SEQ ID NO: 72 and FR4 with SEQ ID NO: 139. In an antibody for use in a non-human animal, the framework region sequence may substantially originate from the human genome (preferably used in a non-human animal when it is an embryo or newly born) or from the genome of the animal in which it is to be used therapeutically.

In one embodiment, an anti-myostatin antibody of the invention wherein all or a portion of the variable region is limited by a particular sequence as shown by a SEQ ID NO herein is further characterized by being a chimeric, humanized, or fully human antibody or antigen-binding portion thereof that antagonizes or neutralizes at least one myostatin activity in vivo or in vitro. An anti-myostatin antibody of the invention wherein all or a portion of the variable region is limited by a particular sequence as shown by a SEQ ID NO herein is further characterized by further characterized by preferentially binding GDF-8 over GDF-11 by at least 20%, 30%, or 40% as measured by a technique in the art e.g., by competition ELISA, or by BIACORE or KINEXA assay to demonstrate at least 20%, 30% or 40% higher affinity (i.e., lower $K_D$) of the antibody to GDF-8 than GDF-11. Preferably an antibody of the invention wherein all or a portion of the variable region is limited by a particular sequence as shown by a SEQ ID NO herein is further characterized by having a $K_D$ for myostatin of less than about $4.2 \times 10^{-9}$ M or $4.0 \times 10^{-9}$ M, preferably less than about $4.6 \times 10^{-10}$ M, $4.0 \times 10^{-10}$ M or $2 \times 10^{-10}$ M and more preferably less than about $8 \times 10^{-11}$ M, $7 \times 10^{-11}$ M, $5 \times 10^{-12}$ M or $1.4 \times 10^{-12}$ M; or alternatively is characterized by a $K_D$ for myostatin of no greater than about $4.2 \times 10^{-9}$ M or $4.0 \times 10^{-9}$ M, preferably no greater than about $4.6 \times 10^{-10}$ M, $4.0 \times 10^{-10}$ M or $2 \times 10^{-10}$ M and more preferably no greater than about $8 \times 10^{-11}$ M, $7 \times 10^{-11}$ M, $5 \times 10^{-12}$ M or $1.4 \times 10^{-12}$ M and/or is further characterized by having an $IC_{50}$ of less than or equal to about 40 nM, 20 nM or 10 nM, more preferably less than or equal to about 5 nM, 4 nM 3 nM, 2 nM or 1 nM in an in vitro myostatin/SBE reporter assay.

Even more preferably, an antibody of the invention wherein all or a portion of the variable region is limited by a particular sequence as shown by a SEQ ID NO herein is further characterized by an $IC_{50}$ in an in vitro myostatin/SBE reporter assay that is less than or equal to about 40 nM, 30 nM, 25 nM, 20 nM or 10 nM, more preferably less than or equal to about 5 nM, 4 nM, 3 nM, 2 nM or 1 nM in an in vitro myostatin/SBE reporter assay. Even more preferably, the anti-myostatin monoclonal antibody's $IC_{50}$ in an in vitro myostatin/SBE reporter assay is at least about two times, three times or four times lower than the $IC_{50}$ of the antibody in an in vitro GDF-11/SBE reporter assay (as described in Example 5 herein). Even more preferably, an antibody of the invention wherein all or a portion of the variable region is limited by a particular sequence as shown by a SEQ ID NO herein is further characterized by not binding a peptide consisting of amino acids 40-64 (inclusive), 43-57 or 45-59 of mature myostatin, preferably human myostatin.

Antibody Expression

The present invention is also directed to cell lines that express an anti-myostatin monoclonal antibody of the invention or portion thereof. Creation and isolation of cell lines producing a monoclonal antibody of the invention can be accomplished using standard techniques known in the art. Preferred cell lines include COS, CHO, SP2/0, NS0 and yeast (available from public repositories such as ATCC, American Type Culture Collection, Manassas, Va.).

A wide variety of host expression systems can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems. An example of a suitable bacterial expression vector is pUC119 and a suitable eukaryotic expression vector is a modified pcDNA3.1 vector with a weakened DHFR selection system. Other antibody expression systems are also known in the art and are contemplated herein.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally the heavy chain and light chain may be expressed in different host cells. Preferably, the recombinant antibodies are secreted into the medium in which the host cells are cultured, from which the antibodies can be recovered or purified. Standard recombinant DNA methodologies are used to obtain antibody heavy and light chain genes, incorporate these genes into recombinant expression vectors, and introduce the vectors into host cells. Such standard recombinant DNA technologies are described, for example, in Sambrook, Fritsch, and Maniatis (Eds.), *Molecular Cloning; A Laboratory Manual*, Second Edition, Cold Spring Harbor, N.Y., 1989; Ausubel, et al (Eds.) *Current Protocols in Molecular Biology*, Greene Publishing Associates, 1989.

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art. See, e.g., Kabat, et al., *Sequences of Proteins of Immunological Interest*, Fifth Edition, U.S. Department of Health and Human Services, NIH Publication No. 91-3242 (1991). DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra). Alternatively, the antigen binding portion can be a Fab fragment, Fab' fragment, $F(ab')_2$ fragment, Fd, or a single chain Fv fragment (scFv). For a Fab fragment heavy chain gene, the HCVR-encoding DNA may be operably linked to another DNA molecule encoding only a heavy chain CH1 constant region.

An isolated DNA encoding a LCVR region may be converted to a full-length light chain gene (as well as to a Fab light chain gene) by operably linking the LCVR-encoding DNA to another DNA molecule encoding a light chain constant region, CL. The sequences of human light chain constant region genes are known in the art. See, e.g., Kabat, supra. DNA fragments encompassing these regions can be obtained by standard PCR amplification. The light chain constant region can be a kappa or lambda constant region.

To create an scFv gene, the HCVR- and LCVR-encoding DNA fragments are operably linked to another fragment encoding a flexible linker, e.g., encoding the amino acid sequence $(Gly_4-Ser)_3$, such that the HCVR and LCVR sequences can be expressed as a contiguous single-chain protein, with the LCVR and HCVR regions joined by the flexible linker. See, e.g., Bird, et al., *Science* 242:423-6, 1988; Huston, et al., *Proc. Natl. Acad. Sci. USA* 85:5879-83, 1988; McCafferty, et al., *Nature* 348:552-4, 1990.

To express an antibody of the invention, a DNA encoding a partial or full-length light and/or heavy chain, obtained as described above, are inserted into an expression vector such that the gene is operably linked to transcriptional and translational control sequences. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the anti-myostatin monoclonal antibody light and/or heavy chain from a host cell. The anti-myostatin monoclonal antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host-cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO cells) (including DHFR-CHO cells, described in Urlaub and Chasin, *Proc. Natl. Acad. Sci. USA* 77:4216-20, 1980, used with a DHFR selectable marker, e.g., as described in Kaufman and Sharp, *J. Mol. Biol.* 159:601-21, 1982, NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e.g., Fab fragments or scFv molecules by techniques that are conventional. It will be understood by a skilled artisan that variations on the above procedure are within the scope of the present invention. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to myostatin. The molecules expressed from such truncated DNA molecules are also encompassed by the antibodies of the invention.

In a preferred system for recombinant expression of an antibody of the invention, a recombinant expression vector encoding both the antibody heavy chain and the antibody light chain is introduced into DHFR-CHO cells by e.g., calcium phosphate-mediated transfection. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies, or antigen-binding portions thereof, of the invention can be expressed in an animal (e.g., a mouse) that is transgenic for human immunoglobulin genes (see, e.g., Taylor, et al., *Nucleic Acids Res.* 20:6287-95, 1992).

Once expressed, the intact antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90%, 92%, 94% or 96% homogeneity are preferred, and 98 to 99% or more homogeneity most preferred, for pharmaceutical uses. Once purified, partially or to homogeneity as desired, the peptides may then be used therapeutically or prophylactically, as directed herein.

Chimeric Antibody

As used herein, the term "chimeric antibody" includes monovalent, divalent or polyvalent immunoglobulins. A monovalent chimeric antibody is a dimer formed by a chimeric heavy chain associated through disulfide bridges with a chimeric light chain. A divalent chimeric antibody is a tetramer formed by two heavy chain-light chain dimers associated through at least one disulfide bridge.

A chimeric heavy chain of an antibody comprises an antigen-binding region derived from the heavy chain of a non-human antibody specific for myostatin, which is operably linked to at least a portion of a human, or substantially human (or species different from that from which the antigen-binding region was derived), heavy chain constant region such as CH1 or CH2, or preferably to a full-length heavy chain constant region. A chimeric light chain of an antibody for use in humans comprises an antigen-binding region derived entirely or substantially from the light chain of a non-human antibody specific for myostatin, operably linked to at least a portion of a human, or substantially human (or species different from that from which the antigen-binding region was derived), light chain constant region (CL), or preferably to a full-length light chain constant region. Antibodies, fragments or derivatives having chimeric heavy chains and light chains of the same or different variable region binding specificity, can also be prepared by appropriate association of the individual polypeptide chains, according to known method steps.

With this approach, hosts expressing chimeric heavy chains are separately cultured from hosts expressing chimeric light chains, and the immunoglobulin chains are separately recovered and then associated. Alternatively, the hosts can be co-cultured and the chains allowed to associate spontaneously in the culture medium, followed by recovery of the assembled immunoglobulin or fragment. Methods for producing chimeric antibodies are known in the art (see, e.g., U.S. Pat. Nos. 6,284,471; 5,807,715; 4,816,567; and 4,816, 397).

Humanized Antibodies

Preferably an antibody of the invention to be used for therapeutic purposes, would have the sequence of the framework and constant region (to the extent it exists in the antibody) derived from the mammal in which it would be used as a therapeutic so as to decrease the possibility that the mammal would illicit an immune response against the therapeutic antibody. Humanized antibodies are of particular interest since they are considered to be valuable for therapeutic application and avoid the human anti-mouse antibody response frequently observed with rodent antibodies. Additionally, in humanized antibodies the effector portion is human so it may interact better with the other parts of the human immune system (e.g., destroy the target cells more efficiently by complement-dependent cytotoxicity or antibody-dependent cellular cytotoxicity). Also, injected humanized antibodies may have a half-life more like that of naturally occurring human antibodies than do e.g., murine antibodies, thereby allowing smaller and less frequent doses to be given. The term "humanized antibody" as used herein refers to an antibody comprising portions of antibodies of different origin, wherein at least one portion is of human origin. For example, the humanized antibody can comprise portions derived from an antibody of nonhuman origin with the requisite specificity, such as a mouse, and from an antibody of human origin, joined together chemically by conventional techniques (e.g., synthetic) or prepared as a contiguous polypeptide using genetic engineering techniques.

Preferably, a "humanized antibody" has CDRs that originate from a non-human antibody (preferably a mouse monoclonal antibody) while framework and constant region, to the extent it is present, (or a significant or substantial portion thereof, i.e., at least about 90%, 92%, 94%, 95%, 96%, 97%, 98% or 99%) are encoded by nucleic acid sequence information that occurs in the human germline immunoglobulin region (sce, e.g., the International ImMunoGeneTics Database) or in recombined or mutated forms thereof whether or not said antibodies are produced in human cell. The CDRs of a humanized antibody may be optimized from the CDRs of a non-human parent antibody from which they originated to generate desired properties, e.g., specificity, affinity and capacity. Optimized CDRs may have amino acid substitutions, additions and/or deletions when compared to the parent CDRs. For example, the amino acid positions of CDRs that are underlined and in bold print in FIGS. 6 and 7 are positions which have been optimized from the parent CDRs as shown in FIG. 5.

Humanized forms of non-human (e.g., murine) antibodies include an intact antibody, a substantially intact antibody, a portion of an antibody comprising an antigen-binding site, or a portion of an antibody comprising a Fab fragment, Fab' fragment, F(ab')$_2$, or a single chain Fv fragment. Humanized antibodies preferably contain minimal sequence derived from non-human immunoglobulin. Humanized antibodies may also comprise residues which are found neither in the recipient antibody nor in the imported CDR or framework sequences. In general, the humanized antibody will comprise substantially all of at least one, and typically two, variable domains, in which all or substantially all of the amino acids in the CDR regions correspond to those of a non-human immunoglobulin and all or substantially all of the amino acids in the FR regions are those of a human immunoglobulin consensus sequence. The humanized antibody optimally also comprises at least a portion of an immunoglobulin constant region (Fc), typically that of a human immunoglobulin. [Jones et al., Nature, 321:522-525 (1986); Riechmann et al., Nature, 332: 323-329 (1988); and Presta, Curr. Op. Struct. Biol., 2:593-596 (1992).]

Humanized antibodies may be subjected to in vitro mutagenesis using methods of routine use in the art (or, when an animal transgenic for human Ig sequences is used, in vivo somatic mutagenesis) and, thus, the framework region amino acid sequences of the HCVR and LCVR regions of the humanized recombinant antibodies are sequences that, while derived from those related to human germline HCVR and LCVR sequences, may not naturally exist within the human antibody germline repertoire in vivo. It is contemplated that such amino acid sequences of the HCVR and LCVR framework regions of the humanized recombinant antibodies are at least 90%, 92%, 94%, 95%, 96%, 98% or most preferably at least 99% identical to a human germline sequence. Preferably, those framework residues of the parent antibody (e.g., murine antibody or generally the antibody from which the humanized antibody is derived) which maintain or affect combining-site structures will be retained. These residues may be identified e.g., by X-ray crystallography of the parent antibody or Fab fragment, thereby identifying the three-dimensional structure of the antigen-binding site.

The humanized antibody of the present invention may comprise or be derived from a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In other embodiments, the humanized antibody of the present invention may comprise or be derived from a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework. In other embodiments, at least FRH1, FRH2, FRH3, or FRH4 is a germline sequence (e.g., human germline) or comprises human consensus sequences for the particular framework. In preferred embodiments, the framework region is a human framework region.

In general, humanized antibodies may be produced by obtaining nucleic acid sequences encoding the HCVR and LCVR of an antibody, e.g., a murine antibody or antibody made by a hybridoma, which binds a myostatin epitope of the invention, identifying the CDRs in said HCVR and LCVR (nonhuman), and grafting such CDR-encoding nucleic acid sequences onto selected human framework-encoding nucleic acid sequences. Optionally, a CDR region may be optimized by mutagenizing randomnly or at particular locations in order to substitute one or more amino acids in the CDR with a different amino acid prior to grafting the CDR region into the framework region. Alternatively, a CDR region may be optimized subsequent to insertion into the human framework region using methods available to one of skill in the art. Preferably, the human framework amino acid sequences are selected such that the resulting antibody is likely to be suitable for in vivo administration in humans. This can be determined, e.g., based on previous usage of antibodies containing such human framework sequence. Preferably, the human framework sequence will not itself be significantly immunogenic.

Alternatively, the amino acid sequences of the frameworks for the antibody to be humanized may be compared to those of known human framework sequences the human framework sequences to be used for CDR-grafting and selected based on their comprising sequences highly similar to those of the parent antibody, e.g., a murine antibody which binds myostatin. Numerous human framework sequences have been isolated and their sequences reported in the art. This enhances the likelihood that the resultant CDR-grafted humanized antibody, which contains CDRs of the parent (e.g., murine) or optimized CDRs of the parent antibody grafted onto selected human frameworks (and possibly also the human constant region) will substantially retain the antigen binding structure and thus retain the binding affinity of the parent antibody. To retain a significant degree of antigen binding affinity, the selected human framework regions will preferably be those that are expected to be suitable for in vivo administration, i.e., not immunogenic.

In either method, the DNA sequence encoding the HCVR and LCVR regions of the preferably murine anti-myostatin antibody are obtained. Methods for cloning nucleic acid sequences encoding immunoglobulins are well known in the art. Such methods may, for example, involve the amplification of the immunoglobulin-encoding sequences to be cloned using appropriate primers by polymerase chain reaction (PCR). Primers suitable for amplifying immunoglobulin nucleic acid sequences, and specifically murine HCVR and LCVR sequences have been reported in the literature. After such immunoglobulin-encoding sequences have been cloned, they will be sequences by methods well known in the art.

After the CDR-encoding sequences are grafted onto the selected human framework encoding sequences, the resultant DNA sequences encoding the "humanized" variable heavy and variable light sequences are then expressed to produce a humanized Fv or humanized antibody that binds myostatin. The humanized HCVR and LCVR may be expressed as part of a whole anti-myostatin antibody molecule, i.e., as a fusion protein with human constant domain sequences whose encoding DNA sequences have been obtained from a commercially available library or which have been obtained using, e.g., one of the above described methods for obtaining DNA sequences, or are in the art. However, the HCVR and LCVR sequences can also be expressed in the absence of constant sequences to produce a humanized anti-myostatin Fv. Nevertheless, fusion of human constant sequences onto the variable region is potentially desirable because the resultant humanized anti-myostatin antibody may possess human effector functions.

Methods for synthesizing DNA encoding a protein of known sequence are well known in the art. Using such methods, DNA sequences which encode the subject humanized HCVR and LCVR sequences (with or without constant regions) are synthesized, and then expressed in a vector system suitable for expression of recombinant antibodies. This may be effected in any vector system which provides for the subject humanized HCVR and LCVR sequences to be expressed as a fusion protein with human constant domain sequences and to associate to produce functional (antigen binding) antibodies or antibody fragments.

Human constant domain sequences are well known in the art, and have been reported in the literature. Preferred human constant light chain sequences include the kappa and lambda constant light chain sequences. Preferred human constant heavy chain sequences include human $IgG_1$, human $IgG_2$, human $IgG_3$, human $IgG_4$, and mutated versions thereof which provide for altered effector function, e.g., enhanced in vivo half-life, reduced Fc receptor binding, altered deamidation profile and the like.

If present, human framework regions are preferably derived from a human antibody variable region having sequence similarity to the analogous or equivalent region of the antigen binding region donor (i.e., the parent antibody). Other sources of framework regions for portions of human origin of a humanized antibody include human variable consensus sequences (see e.g., Kettleborough, C. A. et al. *Protein Engineering* 4:773-783 (1991); Carter et al., WO 94/04679. For example, the sequence of the antibody or variable region used to obtain the nonhuman portion can be compared to human sequences as described in Kabat et al. *Sequences of Proteins of Immunological Interest*, Fifth Edition, NIH, U.S. Government Printing Office (1991). In a particularly preferred embodiment, the framework regions of a humanized antibody chain are derived from a human variable region having at least about 60% overall sequence identity, preferably at least about 70% overall sequence identity and more preferably at least about 85% overall sequence identity, with the variable region of the nonhuman donor. A human portion can also be derived from a human antibody having at least about 65% sequence identity, and preferably at least about 70% sequence identity, within the particular portion (e.g., FR) being used, when compared to the equivalent portion (e.g., FR) of the nonhuman donor.

References further describing methods involved in humanizing a mouse antibody that may be used are e.g., Queen et al., *Proc. Natl. Acad. Sci. USA* 88:2869, 1991; U.S. Pat. No. 5,693,761; U.S. Pat. No. 4,816,397; U.S. Pat. No. 5,225,539; computer programs ABMOD and ENCAD as described in Levitt, M., *J. Mol. Biol.* 168:595-620, 1983; humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)],.

Human Antibodies

As an alternative to humanization, human antibodies can be generated. Human antibodies can be produced using various techniques known in the art, including phage display libraries. Hoogenboom and Winter, J. Mol. Biol., 227:381 (1991); Marks et al., J. Mol. Biol., 222:581 (1991). The techniques of Cole et al. and Boerner et al. are also available for the preparation of human monoclonal antibodies. Cole et al., Monoclonal Antibodies and *Cancer Therapy*, Alan R. Liss, p. 77 (1985) and Boerner et al., J. Immunol., 147(1):86-95 (1991). Similarly, human antibodies can be made by introducing human immunoglobulin loci into transgenic animals, e.g., mice in which the endogenous immunoglobulin genes have been partially or complete inactivated. Upon immunization, e.g., with an antigen comprising an immunogenic epitope of the invention, a full repertoire of human antibody production is obtained, which closely resembles that seen in humans in all respects, including gene rearrangement, assembly and antibody repertoire. This approach is described, for example, in U.S. Pat. Nos. 5,545,807; 5,545,806; 5,569,825; 5,589,369; 5,591,669; 5,625,126; 5,633,425; 5,661,016, and in the following scientific publications: Marks et al., *BioTechnology* 10:779-783, 1992; Lonberg et al., *Nature* 368: 856-859, 1994; Morrison, *Nature* 368: 812-13, 1994; Fishwild et al., *Nature Biotechnology* 14:845-51, 1996; Neuberger, *Nature Biotechnology* 14: 826 (1996); Lonberg and Huszar, *Intern. Rev. Immunol.* 13: 65-93 (1995) and Jobkobovits et al., *Proc. Natl. Acad. Sci. USA*, 90:2551, 1993.

Human immunoglobulin genes introduced into the mouse thus creating transgenic mice capable of responding to antigens with antibodies having human sequences are also described in Bruggemann et al. *Proc. Nat'l. Acad. Sci.* USA 86:6709-6713 (1989)]. There are several strategies that exist for the generation of mammals that produce human antibodies. In particular, there is the "minilocus" approach in which an exogenous Ig locus is mimicked through the inclusion of pieces (individual genes) from the Ig locus (see, e.g., U.S. Pat. Nos. 5,545,807, 5,545,806, 5,625,825, 5,625,126, 5,633,425, 5,661,016, 5,770,429, 5,789,650, and 5,814,318, 5,612,205, 5,721,367, 5,789,215), YAC introduction of large and substantially germline fragments of the Ig loci [See Mendez et al. Nature Genetics 15:146-156 (1997), Green and Jakobovits J. Exp. Med. 188:483-495 (1998)], and introduction of entire or substantially entire loci through the use of microcell fusion (see European Patent Application No. EP 0 843 961 A1).

Any transgenic mouse capable of responding to immunization with antibodies having human sequences may be used to produce an anti-myostatin antibody of the invention when using methods available to one skilled in the art, e.g., when such mouse is immunized with a polypeptide comprising an immunogenic epitope of the invention.

Uses

Antibodies of the present invention are useful in therapeutic, prophylactic and research applications as described herein. An antibody of the invention may be used to diagnose a disorder or disease associated with the expression of human myostatin. In a similar manner, the antibody of the invention can be used in an assay to monitor myostatin levels in a subject being treated for a myostatin-associated condition. Research application include methods that utilize the antibody of the invention and a label to detect myostatin in a sample, e.g., in a human body fluid or in a cell or tissue extract. Antibodies of the invention may by used with or without modification, and are labeled by covalent or non-covalent attachment of a detectable moiety. The detectable moiety can be any one that is capable of producing, either directly or indirectly, a detectable signal. For example, the detectable moiety may be a radioisotope such as, e.g., $^3$H, $^{14}$C, $^{32}$P, $^{35}$S, or $^{125}$I, a fluorescent or chemiluminescent compound, such as fluorescein isothiocyanate, rhodamine, or luciferin; or an exzyme, such as alkaline phosphatase, beta-galactosidase, or horseradish peroxidase. Any method known in the art for separately conjugating the antibody to the detectable moiety may be employed, including those methods described by Hunter, et al., *Nature* 144:945, 1962; David, et al., *Biochemistry* 13: 1014, 1974; Pain, et al., *J. Immunol. Meth.* 40:219, 1981; and Nygren, *J. Histochem. And Cytochem.* 30: 407, 1982.

A variety of conventional protocols for measuring myostatin, including e.g., ELISAs, RIAs, and FACS, are known in the art and provide a basis for diagnosing altered or abnormal levels of myostatin expression. Normal or standard expression values are established using any an known technique, e.g., by combining a sample comprising a myostatin polypeptide with, e.g., antibodies under conditions suitable to form a antigen:antibody complex. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of a radioactive material include $^{125}$I, $^{131}$I, $^{35}$S, or $^{3}$H. (See, e.g., Zola, *Monoclonal Antibodies: A Manual of Techniques*, CRC Press, Inc. (1987)). The amount of a standard complex formed is quantitated by various methods, such as, e.g., photometric means. Amounts of myostatin polypeptide expressed in samples are then compared with the standard values.

As a matter of convenience, the antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a blocking buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic Uses for the Antibody

Myostatin plays a role in muscle development and a number of related disorders or diseases. In adults, myostatin mRNA is primarily detected in skeletal muscle although lower concentrations are also found in adipose tissue and cardiac tissue (Sharma, M., et al, *J. Cell Physiol.* 180:1, 1999). Myostatin knockout mice have two- to three-fold greater muscle mass than their wild type littermates. The increased muscle mass is the result of fiber hypertrophy and hyperplasia (McPherron, A., et al. *Nature* 387:83-90, 1997 and Zhu, X. et al., *FEBS Letters* 474:71). In addition, the myostatin knockout mice accumulate less fat than their wild type littermates but otherwise appear normal and healthy. Myostatin has also been recently shown to be an important regulator of adipogenesis (Rebbapragada, A., et al., *Mol. and Cell. Bio.* 23:7230-7242, 2003). Additionally, bone structure and content has been recently studied in myostatin deficient mice (Hamrick M. W., et al., *J. Orthopaedic Research* 21:1025, 2003; Hamrick, M. W., et al., *Calcif Tissue Int* 71:63, 2002.

Therefore, a pharmaceutical composition comprising an anti-myostatin monoclonal antibody of the invention may be used to increase muscle mass, increase bone density, decrease muscle wasting, or may be useful for the treatment or prevention of conditions wherein the presence of myostatin causes or contributes to undesirable pathological effects or decrease of myostatin levels has a therapeutic benefit in mammals, preferably humans, including, but not limited to, muscle wasting, muscle injury, surgery, repair of damaged muscle, frailty, age-related sarcopenia, disuse atrophy, osteoporosis, osteoarthritis, ligament growth and repair, obesity, suppression of body fat accumulation, obesity, muscular dystrophy of any type, critical care myopaythy, alcoholic myopathy, cachexia (e.g., cancer-related or HIV-induced, or resulting from COPD, chronic lung disease, recovery from sepsis, renal failure, liver failure, cardiac failure or disease), metabolic syndrome, post-burn muscle wasting, and Type II diabetes. Disuse atrophy may result from numerous causes or incidents including any disorder or disease or state which leads to prolonged immobility or disuse or bed rest including, but not limited to, solid organ transplant, joint replacement, stroke, spinal cord injury, recovery from severe burn, sedentary chronic hemodialysis, post-sepsis recovery and exposure to microgravity. Since myostatin is highly conserved in sequence and function across species, the antibodies of the invention may be used to increase muscle mass, increase bone density or treat or prevent conditions in non-human mammals or avian species [e.g., domestic animals (e.g., canine and feline), sports animals (e.g., equine), food-soiurce animals (e.g., bovine, porcine and ovine), avian species (e.g., chicken, turkey, other game birds or poultry)] wherein the presence of myostatin causes or contributes to undesirable pathological effects or decrease of myostatin levels has a therapeutic benefit.

The use of an anti-myostatin monoclonal antibody of the present invention for treating or preventing of at least one of the aforementioned disorders in which myostatin activity is detrimental or which benefits for decreased levels of bioactive myostatin is contemplated herein. Additionally, the use of an anti-myostatin monoclonal antibody of the present invention for use in the manufacture of a medicament for the treatment of at least one of the aforementioned disorders is contemplated.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, includes administration of a compound of the present invention for treatment of a disease or condition in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease or disorder or alleviating symptoms or complications thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

Pharmaceutical Composition

An antibody of the invention can be incorporated into pharmaceutical compositions suitable for administration to a subject. The compounds of the invention may be administered alone or in combination with a pharmaceutically acceptable carrier, diluent, and/or excipients, in single or multiple doses. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques as in e.g., Remington, *The Science and Practice of Pharmacy*, 19$^{th}$ Edition, Gennaro, Ed., Mack Publishing Co., Easton, Pa. 1995 which provides a compendium of formulation techniques as are generally known to practitioners.

A pharmaceutical composition comprising an anti-myostatin monoclonal antibody of the present invention can be administered to a subject at risk for or exhibiting pathologies as described herein using standard administration techniques including oral, intravenous, intraperitoneal, subcutaneous, pulmonary, transdermal, intramuscular, intranasal, buccal, sublingual, or suppository administration.

A pharmaceutical composition of the invention preferably is a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effect of the antibody, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically-effective or prophylactically-effective amount is at least the minimal dose, but less than a toxic dose, of an active agent which is necessary to impart therapeutic benefit to a subject. Stated another way, a therapeutically-effective amount of an antibody of the invention is an amount which in mammals, preferably humans, increases muscle mass, increases bone density, or treats conditions wherein the presence of myostatin causes or contributes to undesirable pathological effects or decrease in myostatin levels results in a beneficial therapeutic effect in a mammal, preferably a human, including, but not limited to, muscle wasting, muscle injury, surgery frailty, age-related sarcopenia, disuse atrophy, osteoporosis, osteoarthritis, ligament growth and repair, obesity, suppression of body fat accumulation, muscular dystrophy of any type, critical care myopaythy, cachexia (e.g., cancer-related or HIV-induced, or resulting from COPD, renal failure, liver failure, cardiac failure or disease), metabolic syndrome and Type II diabetes. Disuse atrophy may result from numerous causes or incidents including any disorder or disease or state which leads to prolonged immobility or disuse or bed rest including, but not limited to, solid organ transplant, joint replacement, stroke, spinal cord injury, recovery from severe burn, sedentary chronic hemodialysis, post-sepsis recovery and exposure to microgravity.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are straightforward in the art.

The pharmaceutical composition typically must be sterile and stable under the conditions of manufacture and storage in the container provided, including e.g., a sealed vial or syringe. Therefore, pharmaceutical compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/mL, or more) of antibody concentration. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 0.001 to 1000 μg; however, doses below or above this exemplary range are envisioned, especially considering the aforementioned factors. The daily parenteral dosage regimen can be about 0.1 µg/kg to about 100 mg/kg of total body weight, preferably from about 0.3 µg/kg to about 10 mg/kg and more preferably from about 1 µg/kg to 1 mg/kg, even more preferably from about 0.5 to 10 mg/kg body weight per day. Progress may be monitored by periodic assessment. For repeated administrations over several days or longer, depending on the condition, the treatment is repeated until a desired suppression of disease symptoms occurs. However, other dosage regimens may be useful and are not excluded herefrom. The desired dosage can be delivered by a single bolus administration, by multiple bolus administrations, or by continuous infusion administration of antibody, depending on the pattern of pharmacokinetic decay that the practitioner wishes to achieve.

These suggested amounts of antibody are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate. Generally, pH between 6 and 8 is preferred.

Articles of Manufacture

In another embodiment of the invention, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of the invention which is effective for preventing or treating the disorder or condition and may have a sterile access port (for example the container may be an intravenous solution bag or a vial having a stopper pierceable by a hypodermic injection needle). The active agent in the composition is an anti-myostatin antibody of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

EXAMPLES

Example 1

ELISA Assays

A. Myostatin and GDF-11 Coated Plates

Mouse/human chimeric anti-myostatin Fabs of the present invention are tested in an ELISA assay, in which binding of the Fab to mature myostatin (dimeric form) coated at various concentrations on a 96-well plate is measured. Binding of the Fabs to GDF-11 is also tested.

Each well of two 96-well plates is coated with 50 µl of recombinant human myostatin (R&D systems, carrier-free, re-supended first in 4 mM HCl and then coated at 1 µg/ml in carbonate buffer, pH 9.6) or 50 µl recombinant human GDF-11 (Peprotech, Inc., Cat. # 120-11, carrier-free, re-suspended first in 4 mM HCl and then coated at 1 µg/ml in carbonate buffer, pH 9.6). The plates are incubated at 4° C. overnight. The wells are aspirated and washed twice with PBST (PBS+ 0.1% Tween-20). The plates are blocked with 200 µl blocking buffer per well (1% BSA in PBST for 1 hour).

Fabs from periplasmic extracts to be tested are serially diluted into PBST. Fifty microliters of each Fab solution is added to the GDF-8 and GDF-11 coated plate columns. The plates are incubated for 1 hour at room temperature. The wells are then washed 3 times with PBST.

Alkaline phosphatase-conjugated secondary antibody (50 µl goat anti-mouse kappa AP (Southern Biotech), diluted 1:1000 in PBST) is added to each well and incubated for 30 minutes at room temperature. The wells are then washed 3 times with PBST. Fifty microliters of chromogenic substrate (AMP/PMP) is added to each well and allowed to develop at room temperature. The absorbance of the wells is read at OD of 560 nm. For each Fab a titration curve is obtained an the relative OD at the mid point of of the reference Fab curve reported.

These data demonstrate that all Fabs tested bind to plate-bound human mature myostatin with cross reactivity to GDF11.

B. Fab Capture ELISA

A 96-well plate is coated with 50 µl of goat-anti-human kappa antibody at 2 µg per ml in carbonate buffer. The plates are incubated at 4° C. overnight. The wells are aspirated and washed twice with PBST (PBS+0.1% Tween-20). The plates are blocked with 200 µl blocking buffer per well (1% BSA in PBST for 1 hour)

Fabs from periplasmic extracts to be tested are captured in columns on the plates for 2 hours at 37° C. After washing 3 times with PBST, 50 µl of 2 fold serial dilutions of biotinylated Myostatin (from 100 nM to 780 pM) are added to each column of captured Fabs and incubated for 1 hour at 37° C. The plate is then washed with PBST and incubated with PEST at 37 degrees C. for 1-3 hours.

Alkaline phosphatase-conjugated Neutravidin (Pierce, diluted 1:1000 in PBST) is added to each well and incubated for 2 minutes at room temperature. The wells are then washed 3 times with PBST. 50 µl of chromogenic substrate (AMP/PMP) is added to each well and allowed to develop at room temperature. The absorbance of the wells is read at an OD of 560 nm. And the relative OD compared to that of the maximum OD for the reference Fab reported.

All Fabs of the invention tested bind soluble human mature myostatin.

Example 2

Myostatin Neutralization Assay

Ectodermal explants are removed from stage 8-9 blastula Xenopus embryos by standard procedures and cultured in 0.5× MBS (1× MBS: 88 mM NaCl, 1 mM KCl, 0.7 mM CaCl$_2$, 1 mM MgSO$_4$, 5 mM HEPES, 2.5 mM NaHCO$_3$, 1:1000 v/v gentamycin, 0.1% bovine serum albumin) with the addition of growth factor (GDF8 or GDF11) plus or indicated, for 18 hours at 18° C., by which time control embryos reach the early neurula stage (stage 15-16). Explants are photographed and the length of each explant is measured using an image analysis algorithm designed for animal cap quantitation. Explants not treated with either growth factor or Fab (controls), round into balls of epidermis. Myostatin and GDF-11 induce mesoderm in these ectodermal explants which causes the explants to elongate and form dumbbell-like structures. Antibodies or Fabs, when tested for neutralizing activity, are added to the culture medium containing myostatin for the entire length of the culture period and their ability to inhibit the growth factor-induced elongation movements is assessed. Myostatin is added to the explants at 25 ng/ml. Antibodies or Fabs to be tested are added at 20 μg/ml. A Fab generated to an irrelevant antigen is used as a control. A commercially available monoclonal anti-mouse GDF8 antibody may be tested as a control, this antibody is produced in goats immunized with purified mouse GDF8 and demonstrated by the manufacturer to neutralize elongation of Xenopus animal caps elicited by 25 ng/ml of murine GDF8 when present at about 10-20 μg/ml (R&D Systems Cat. #MAB788).

ImagePro (v4.5.1.22, from Media Cybernetics) is used for the image processing. A macro is written to automate the image processing. The macro processes the image and records length in units of bits. Alternative measuring methods may be used as known in the art. Antibodies of the invention are contemplated to neutralize GDF8 activity in the animal cap assay.

buffer used for kinetic experiments contained 10 mM HEPES, pH 7.4, 150 mM NaCl, 0.005% P20.

Collection of kinetic binding data is performed at maximum flow rate (100 μl/min). Each analysis cycle consists of (i) 250 μl injection of a Fab (concentration range of 50 nM to 0.4 nM in 2-fold dilution increments) over all 4 flow cells with flow cell 1 as the reference flow cell, (ii) 20 min dissociation (buffer flow), (iii) regeneration of of the GDF-8 or GDF-11 surface with a two 15 μl injection of 10 mM glycine, pH 1.5, (iv) a 15 μl blank injection of running buffer, and (v) a 2 min stabilization time before start of next cycle. Signal is monitored as flow cell 2 minus flow cell 1, flow cell 3 minus flow cell 1 and flow cell 4 minus flow cell 1. Samples and a buffer blank are injected in duplicate in a random order. Data are processed using SCRUBBER (Center for Biomolecular Interaction Analysis, Univ. of Utah) software. Association and dissociation rates for each cycle are determined by fitting of the biosensor data using to a simple association model using ClampXP (Center for Biomolecular Interaction Analysis, Univ. of Utah) to extract the $k_{on}$ and $k_{off}$ rate constants; the equilibrium binding constant $K_d$ is calculated using the relationship $K_d = k_{off}/k_{on}$. The Fabs 41-1 and 412-6, when measured in the above assay, have affinities for GDF-8 of 4.16 nM ($4.16 \times 10^{-1}$ M) and 0.46 nM ($4.6 \times 10^{-10}$ M) respectively, and had affinities for GDF-11 of 8.96 nM and 0.81 nM respectively; the relative specificity for both Fabs was approximately a 2-fold preference for GDF-8 relative to GDF-11. (Table 2)

TABLE 2

| | GDF-8 | | | GDF-11 | | |
|---|---|---|---|---|---|---|
| Fab | $k_{on}$ (M$^{-1}$ s$^{-1}$) ($\times 10^{-6}$) | $k_{off}$ (sec$-1$) ($\times 10^3$) | $K_d$ (nM) calc | $k_{on}$ (M$^{-1}$ s$^{-1}$) ($\times 10^{-6}$) | $k_{off}$ (sec$-1$) ($\times 10^3$) | $K_d$ (nM) calc |
| 41-1 | 1.16 | 4.82 | 4.16 | 1.04 | 9.32 | 8.96 |
| 412-6 | 3.59 | 1.66 | 0.46 | 5.09 | 4.10 | 0.81 |

Example 3

Affinity Measurement of Fabs

The affinity ($K_D$) and $k_{on}$ and $k_{off}$ rates of anti-myostatin Fabs of the present invention are measured using a BIAcore® 2000 instrument containing a CM4 sensor chip. The BIAcore® utilizes the optical properties of surface plasmon resonance to detect alterations in protein concentration of interacting molecules within a dextran biosensor matrix. Except where noted, all reagents and materials are purchased from BIAcore® AB (Upsala, Sweden). All measurements are performed at 25° C. Samples containing Fabs are dissolved in HBS-EP buffer (150 mM sodium chloride, 3 mM EDTA, 0.05% (w/v) surfactant P-20, and 10 mM HEPES, pH 7.4). Myostatin or GDF-11 (R&D Systems) is immobilized onto flow cells of a CM4 chip using amine-coupling chemistry. Flow cells (1-4) are activated with a 1:1 mixture of 0.1 M N-hydroxysuccinimide and 0.1 M 3-(N,N-dimethylamino) propyl-N-ethylcarbodiimide at a flow rate of 20 μl/min. Myostatin or GDF-11 (2.5 μg/mL in 10 mM sodium acetate, pH 4.5) is manually injected over individual flow cells at a flow rate of 10 μL/min. The surface density is monitored and until each flow cell reaches a surface density of ~150 response units (RU). Surfaces are blocked with a 50 μl injection of 1 M ethanolamine-HCl, pH 8.5 (10 μL/min). To ensure complete removal of any noncovalently bound myostatin or GDF-11, 15 μl of 10 mM glycine, pH 1.5 is injected twice. Running Example 4

Affinity Measurement of Mabs

Binding affinity measurements for full-length monoclonal antibodies of the invention are determined using a Sapidyne KINEXA assay. NHS-activated fast-flow sepharose beads (GE Healthcare) are pre-coated with an antibody of the invention (50 μg anti-myostatin antibody per ml of beads) and blocked with 10 mg/ml BSA in 1 M Tris-HCl, pH 8.0. Then 2 pM, 4 pM, 40 pM of an antibody of the invention (e.g., 3-74/C1E4) is incubated with various concentration (e.g., 2.4 pM to 10 nM, serial dilutions) of myostatin in running buffer (PBS, 0.005% (v/v) Tween-20 and 1 mg/ml ovalbumin) for 10 hours at room temperature. To determine the free antibody present at equilibrium, each sample is passed through the myostatin-coated beads. The amount of bead-bound antibody is then quantified by passing a solution of fluorescent (Cy5) labeled goat ant-human Fc antibody (Jackson Immuno Research) diluted 1:4000 in running buffer over the beads. The measured fluorescence signal is proportional to the concentration of free antibody at equilibrium. Each concentration of myostatin is measured in duplicate. The equilibrium dissociation constant ($K_D$) is obtained from non-linear regression of the competition curves using a multiple-curve, one-site homogeneous binding model (KINEXA software).

The association rate constant ($k_{on}$) for GDF-8 binding is also determined using a Sapidyne KINEXA assay. Two pM antibody is mixed with 20 pM GDF-8 using the same conditions as described above. At various times, samples are probed for free antibody using the conditions described above for equilibrium binding, and then the resulting time dependence is fit using the KINEXA software to determine the association rate ($k_{on}$). The dissociation rate constant ($k_{off}$) is calculated using the expression $k_{off}=KD \times k_{on}$. Full-length monoclonal antibody 3-74/C1E4 (operably linked to an $IgG_4$ Fc region) was measured using the described assay, the results obtained are listed below in Table 3.

TABLE 3

| Mab | $K_D$, pM (95% CI) | $k_{on}$, $M^{-1} s^{-1}$ (95% CI) | $k_{off}$, $s^{-1}$, calculated |
|---|---|---|---|
| 3-74/C1E4 | 1.39 (0.20-3.58) | $1.49 \times 10^6$ ($1.39$-$1.58 \times 10^6$) | $2.08 \times 10^{-6}$ |

Example 5

Myostatin/SBE Reporter Assay

In this reporter assay, a plasmid encoding a reporter gene, i.e., luciferase gene, downstream of a SMAD binding element ("SBE"), more specifically $(CAGA)_{12}$ expresses luciferase protein when a molecule such as myostatin, GDF-11, or other TGF-β superfamily member binds its own receptor, thereby triggering SMAD signaling which results in a phosphorylated SMAD complex which is capable of binding the SBE. The CAGA sequence was previously reported to be a TGF-β responsive sequence within the promoter of the TGF-β induced gene PAI-1 (Denner et al., *EMBO J.*, 17:3091-3100, 1998). The amount of active myostatin exposed to the cells is directly proportional to the quantity of luciferase enzyme produced which is directly proportional to the quantity of light produced and measurable. The presence of an inhibitor (e.g., an antibody that binds myostatin) reduces the quantity of myostatin able to activate the SBE which ultimately results in a reduced production of light. This assay is also described in International Publication Number WO 2004/037861 incorporated herein.

It is contemplated that a Myostatin/SBE Reporter Assay not be limited to the exact conditions described herein, other types of cells may be used, e.g., 293HEK (ATCC) or A204 Rhabsomyosarcoma cells (see, e.g., Whittemore, et al. *BBRC*, 200:965-71, 2003); other types of reporters may be used, e.g., CAT, β-gal, GFP, and other growth conditions for the cells and assay conditions including varying amounts of myostatin in the reaction may be used. One of skill in the art would readily be able to discern if an assay falls within the scope of a myostatin/SBE reporter assay for it would have a vector comprising an SBE element upstream of a reporter gene introduced into a host cell, wherein the SBE element used is responsive to the SMAD produced in response to myostatin binding the myostatin receptor. R. S. Thies, et al., *Growth Factors*, 18:251-259, 2001, describes a similar assay while, Wittemore, L. et al., *BBRC*, 300:965-971, 2003 describes the SBE element response to the SMAD produced in response to myostatin binding its receptor.

In this assay, 293E cells (Edge Biosystems) in a T-75 flask are grown in DMEM/F12 media (1:1) (Gibco 10565-042) and 10% FBS. The cells are transfected with a mix of 100 μl lipofectamine 2000 (Invitrogen 11668-019), 5 ml OptiMEM I (Gibco 51985-034) and 30 μg SB-luciferase DNA for 4 hours at 37° C. The transfection mix is then removed and complete media added for 1 hour at 37° C. The cells are then trypsinized and re-suspended in complete media at $2 \times 10^6$ cells/ml and 50 μl plated in each well of a Biocoat 96-well plate (BD 35-6461) and incubated for 1 hour at 37° C. After the incubation is complete, media is replaced with 100 μl of each Fab to be tested that is serially diluted 1:2 and pre-incubated for 1 hour at 37° C. with a 1:1 solution of 40 ng/ml myostatin (R&D Systems 788-G8) or GDF-11 (R&D Systems) in complete media.

The plate is left overnight at 37° C., 5% $CO_2$ and the following day 100 μl of a 1:1 mix of Glo Lysis Buffer and Bright-Glo Luciferase reagent (Promega) is added to each well and mixed by pipeting. From this mix, 150 μl is transferred to a white 96-well plate and luminescence measured using a luminometer. Luminescence is then plotted against Fab concentration and the $IC_{50}$ for each Fab for myostatin and GDF-11 is calculated.

Fabs tested using the above-described conditions yield $IC_{50}$ values as listed in Table 4 below.

TABLE 4

| Fab | $IC_{50}$ GDF8 | $IC_{50}$ GDF11 |
|---|---|---|
| 41H-A7 | 10 nM | 40 nM |
| 41L3F12 | 40 nM | 100 nM |
| 41C1A2 | 1 nM | 1.2 nM |
| 41C1A4 | 1 nM | 2 nM |
| 41C1E4 | 1 nM | 4 nM |
| 41C12A4 | 1 nM | 4 nM |
| 41C2A4 | 1 nM | 4 nM |
| 3-74/C1E4 | 1 nM | 4 nM |

Example 6

Pharmacokinetics

The pharmacokinetics (PK) of the antibodies of the invention may be evaluated in C57B6/SCID mice at a dose of 1 mg/kg after a single intravenous (IV) or intraperitoneal (IP) administration. The animals receive a mixture of unlabeled and $^{125}$I-labeled antibody at a dose described above and serum concentration is determined based on $^{125}$I radioactivity in the serum and the specific activity of the injected dose. Serum concentration of the antibody administered either IV or IP versus time is plotted.

Example 7

In Vivo Effect on Muscle Mass and Strength

To determine whether an antibody of the invention blocks myostatin activity in vivo, an antibody of the invention may be tested in adult SCID mice. SCID mice suffer from severe combined immune deficiency, and therefore do not generate an immunological reaction following injection of an antibody of the invention. Muscle mass is used as an indicator for myostatin activity in mice treated with an antibody of the invention.

Female SCID/CB17 mice (Taconic Biotechnology) are weighed and distributed into groups of ten. An antibody of the invention (41C1E4) in PBS buffer is injected subcutaneously into the mice at various doses (10, 5, and 2 mg/kg) on days 0 and 7. In a control group, IgG at 10 mg/kg is injected subcutaneously into the mice on days 0 and 7. On day 14, muscle strength, the strength of the front limb, is measured with a grip strength test meter (e.g., model 1027 csx, Columbus Instruments). The animals are terminated and muscle mass is assessed by nuclear magnetic resonance (NMR). The gastrocnemius and quadriceps muscle wet weights are also measured as well as body weight. Results, means and standard errors for the various parameters, are as shown in Table 5 below. The data is transformed by a Box Cox transformation method to normalize the data. Outliers for each parameter are identified by statistical means with JMP 5.1 software (SAS, Inc.) and excluded from the data set. Statistical significance was determined by ANOVA and a Student's t-test. A p value of less than 0.05 was considered significant. The antibody tested at 5 mg/kg and 10 mg/kg results in statistically significant results relative to the control IgG group for all parameters tested. The antibody tested at 2 mg/kg results in statistically significant results relative to the control IgG group for NMR Muscle, quadriceps wet weight and gastrocnemius wet weight parameters.

TABLE 5

| Study Group | Initial BW (g) | Final BW (g) | NMR Muscle (g) | Quadriceps wet wt (mg) | Gastrocnemius wet wt (mg) | Grip Strength (Newtons) |
|---|---|---|---|---|---|---|
| Control IgG | 19.82 ± 0.35 | 20.89 ± 0.33 | 15.17 ± 0.27 | 159.92 ± 4.13 | 92.84 ± 1.99 | 2.89 ± 0.08 |
| 41C1E4 2 mg/kg | 19.92 ± 0.32 | 21.78 ± 0.22 | 16.27 ± 0.13 | 172.07 ± 1.53 | 102.13 ± 0.88 | 2.99 ± 0.07 |
| 41C1E4 5 mg/kg | 19.94 ± 0.34 | 21.9 ± 0.37 | 16.54 ± 0.39 | 185.27 ± 4.67 | 108.16 ± 2.3 | 3.23 ± 0.04 |
| 41C1E4 10 mg/kg | 19.9 ± 0.34 | 22.3 ± 0.4 | 16.99 ± 0.27 | 190.03 ± 3.2 | 109.5 ± 2.03 | 3.18 ± 0.08 |

BW = body weight

---

What we claim is:

1. A method of enhancing muscle mass in a human comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72,
and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

2. The method of claim 1, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

3. The method of claim 1, wherein the LCVR comprises a polypeptide with SEQ ID NO: 98 and the HCVR comprises a polypeptide with SEQ ID NO: 138.

4. A method of increasing muscle strength in a human comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72,
and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

5. The method of claim 4, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

6. The method of claim 4, wherein the LCVR comprises a polypeptide with SEQ ID NO: 98 and the HCVR comprises a polypeptide with SEQ ID NO: 138.

7. A method of increasing bone density in a human comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72,
and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

8. The method of claim 7, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

9. The method of claim 7, wherein the LCVR comprises a polypeptide with SEQ ID NO: 98 and the HCVR comprises a polypeptide with SEQ ID NO: 138.

10. A method of decreasing myostatin levels in a human with frailty, age-related sarcopenia, disuse atrophy, muscle wasting, muscle injury, muscle weakness, myopathy, metabolic syndrome, osteoporosis, osteoarthritis, obesity or Type II diabetes comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72, and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

11. The method of claim 10, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

12. The method of claim 10, wherein the LCVR comprises a polypeptide with SEQ ID NO: 98 and the HCVR comprises a polypeptide with SEQ ID NO: 138.

13. A method of decreasing muscle wasting in a human comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72,
and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

14. The method of claim 13, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

15. The method of claim 13, wherein the LCVR comprises a polypeptide with SEQ ID NO: 98 and the HCVR comprises a polypeptide with SEQ ID NO: 138.

16. A method of treating a human with cachexia, comprising administering to said human a therapeutically effective amount of an anti-myostatin monoclonal antibody comprising a heavy chain variable region (HCVR) and a light chain variable region (LCVR), wherein said HCVR comprises:
   a) a peptide at CDRH1 with SEQ ID NO: 42,
   b) a peptide at CDRH2 with SEQ ID NO: 71, and
   c) a peptide at CDRH3 with SEQ ID NO: 72,
and wherein said LCVR comprises:
   a) a peptide at CDRL1 with SEQ ID NO: 12,
   b) a peptide at CDRL2 with SEQ ID NO: 154, and
   c) a peptide at CDRL3 with SEQ ID NO: 37.

17. The method of claim 16, wherein the HCVR comprises:
   a) a peptide at CDRH1 with SEQ ID NO: 40,
   b) a peptide at CDRH2 with SEQ ID NO: 60, and
   c) a peptide at CDRH3 with SEQ ID NO: 72,
and wherein the LCVR comprises:
   a) a peptide at CDRL1 with SEQ ID NO: 9,
   b) a peptide at CDRL2 with SEQ ID NO: 18, and
   c) a peptide at CDRL3 with SEQ ID NO: 34.

18. The method of claim 16, wherein the LCVR comprises a polypeptide with SEQ ID NO: 98 and the HCVR comprises a polypeptide with SEQ ID NO: 138.

\* \* \* \* \*

UNITED STATES PATENT AND TRADEMARK OFFICE
CERTIFICATE OF CORRECTION

PATENT NO. : 8,066,995 B2
APPLICATION NO. : 12/611470
DATED : November 29, 2011
INVENTOR(S) : Julian Davies et al.

Page 1 of 1

It is certified that error appears in the above-identified patent and that said Letters Patent is hereby corrected as shown below:

On the first page of the issued patent, in Column 2, Line 6 of the Abstract, the word "bond" should be deleted and the word --bone-- should be inserted in its place.

On the first page of the issued patent, in Column 2, Line 7 of the Abstract, the words "species, X17251" should be deleted and the word --species.-- inserted in its place.

Signed and Sealed this
Twenty-first Day of February, 2012

David J. Kappos
*Director of the United States Patent and Trademark Office*

SEQUENCE LISTING

<160> NUMBER OF SEQ ID NOS: 158

<210> SEQ ID NO 1
<211> LENGTH: 375
<212> TYPE: PRT
<213> ORGANISM: Homo sapiens

<400> SEQUENCE: 1

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly

```
            210                 215                 220
Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
                370                 375

<210> SEQ ID NO 2
<211> LENGTH: 109
<212> TYPE: PRT
<213> ORGANISM: Homo sapiens

<400> SEQUENCE: 2

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 3
<211> LENGTH: 109
<212> TYPE: PRT
<213> ORGANISM: Ovis sp.

<400> SEQUENCE: 3

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Leu Phe Leu Gln Lys Tyr Pro His Thr His Leu Val His Gln Ala
    50                  55                  60
```

Asn Pro Lys Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Gly Met Val Val Asp Arg Cys Gly Cys Ser
            100                 105

<210> SEQ ID NO 4
<211> LENGTH: 109
<212> TYPE: PRT
<213> ORGANISM: Homo sapiens

<400> SEQUENCE: 4

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 5
<211> LENGTH: 339
<212> TYPE: DNA
<213> ORGANISM: Artificial
<220> FEATURE:
<223> OTHER INFORMATION: Synthetic construct

<400> SEQUENCE: 5
gaggtgaagc tggtggagtc tgggggaggc ttagtgaagc ctggagggtc cctgaaactc        60
tcctgtgcag cctctggact cactttcagt aggtatggca tgtcttgggt tcgccagact       120
ccggagagga ggctggagtg ggtcgcagcc attaatagtc atggtggtag cacctactat       180
tcagacactg tgaagggccg attcaccatt tccagagaca tgccaagaa caccctgtac        240 ctgcaaatga acagtctgag gtctgaggac acagccttgt attactgtgc aagacttccg       300
gactactggg gccaaggcac cacggtcacc gtttcctca                              339

<210> SEQ ID NO 6
<211> LENGTH: 324
<212> TYPE: DNA
<213> ORGANISM: Artificial
<220> FEATURE:
<223> OTHER INFORMATION: Synthetic construct

<400> SEQUENCE: 6
gaaaatgtgc tgacccagtc tccagcaatc atgtctgcat ctccagggga aaaggtcacc        60
atgacctgca gggccagctc aagtgtaagt tccagttact tgcactggta ccagcagaag       120
tcaggtgcct cccccaaact ctggatctat agcacatcca acttggcttc tggagtccct       180
gctcgcttca gtggcagtgg gtctgggacc tcttactctc tcacaatcag cagtgtggag       240
gctgaagatg ctgccactta ttactgccag cagtacagtg gttaccactt cacgttcggc       300

```
tcggggacca agctggaaat gaaa                                            324
```

<210> SEQ ID NO 7
<211> LENGTH: 113
<212> TYPE: PRT
<213> ORGANISM: Artificial
<220> FEATURE:
<223> OTHER INFORMATION: Synthetic construct

<400> SEQUENCE: 7

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Arg Tyr
            20                  25                  30

Gly Met Ser Trp Val Arg Gln Thr Pro Glu Arg Leu Glu Trp Val
        35                  40                  45

Ala Ala Ile Asn Ser His Gly Gly Ser Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Leu Tyr Tyr Cys
                85                  90                  95

Ala Arg Leu Pro Asp Tyr Trp Gly Gln Gly Thr Thr Val Thr Val Ser
            100                 105                 110

Ser
```

<210> SEQ ID NO 8
<211> LENGTH: 108
<212> TYPE: PRT
<213> ORGANISM: Artificial
<220> FEATURE:
<223> OTHER INFORMATION: Synthetic construct

<400> SEQUENCE: 8

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr His
                85                  90                  95

Phe Thr Phe Gly Ser Gly Thr Lys Leu Glu Met Lys
            100                 105
```

<210> SEQ ID NO 9
<211> LENGTH: 12
<212> TYPE: PRT
<213> ORGANISM: Mus sp.

<400> SEQUENCE: 9

```
Arg Ala Ser Ser Ser Val Ser Ser Ser Tyr Leu His
1               5                   10
```

<210> SEQ ID NO 10

```
<211> LENGTH: 12
<212> TYPE: PRT
<213> ORGANISM: Artificial
<220> FEATURE:
<223> OTHER INFORMATION: Synthetic construct

<400> SEQUENCE: 10

Arg Ala Ser Gln Ser Val Ser Ser Ser Tyr Leu His
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic construct

<400> SEQUENCE: 11

Arg Ala Leu Ser Ser Val Ser Ser Ser Tyr Leu His
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: X is S or L
<220> FEATURE:
<221> NAME/KEY: MISC_FEATURE
<222> LOCATION: (4)..(4)
<223> OTHER INFORMATION: X is S or Q

<400> SEQUENCE: 12

Arg Ala Xaa Xaa Ser Val Ser Ser Ser Tyr Leu His
1               5                   10

<210> SEQ ID NO 13
<211> LENGTH: 7
<212> TYPE: PRT
<213> ORGANISM: Artificial
<220> FEATURE:
<223> OTHER INFORMATION: Synthetic construct

<400> SEQUENCE: 13

Ser Thr Ser Asn Leu Ala Ser
1               5

<210> SEQ ID NO 14
<211> LENGTH: 7
<212> TYPE: PRT
<213> ORGANISM: Artificial
<220> FEATURE:
<223> OTHER INFORMATION: Synthetic construct

<400> SEQUENCE: 14

Ser Thr Ser Asn Leu Ala Ala
1               5

<210> SEQ ID NO 15
<211> LENGTH: 7
<212> TYPE: PRT
<213> ORGANISM: Artificial
<220> FEATURE:
<223> OTHER INFORMATION: Synthetic construct

<400> SEQUENCE: 15
```

Ser Thr Ser Asn Leu Ala Thr
1               5

<210> SEQ ID NO 16
<211> LENGTH: 7
<212> TYPE: PRT
<213> ORGANISM: Artificial
<220> FEATURE:
<223> OTHER INFORMATION: Synthetic construct

<400> SEQUENCE: 16

Ser Thr Ser Asn Leu Ala Asn
1               5

<210> SEQ ID NO 17
<211> LENGTH: 7
<212> TYPE: PRT
<213> ORGANISM: Artificial
<220> FEATURE:
<223> OTHER INFORMATION: Synthetic construct

<400> SEQUENCE: 17

Ser Thr Ser Asn Leu Ala Asp
1               5

<210> SEQ ID NO 18
<211> LENGTH: 7
<212> TYPE: PRT
<213> ORGANISM: Artificial
<220> FEATURE:
<223> OTHER INFORMATION: Synthetic construct

<400> SEQUENCE: 18

Ser Thr Ser Asn Leu Val Ala
1               5

<210> SEQ ID NO 19
<211> LENGTH: 7
<212> TYPE: PRT
<213> ORGANISM: Artificial
<220> FEATURE:
<223> OTHER INFORMATION: Synthetic construct

<400> SEQUENCE: 19

Ser Thr Ser Asn Leu Val Phe
1               5

<210> SEQ ID NO 20
<211> LENGTH: 7
<212> TYPE: PRT
<213> ORGANISM: Artificial
<220> FEATURE:
<223> OTHER INFORMATION: Synthetic construct

<400> SEQUENCE: 20

Ser Thr Ser Asn Leu Thr Trp
1               5

<210> SEQ ID NO 21
<211> LENGTH: 7
<212> TYPE: PRT
<213> ORGANISM: Artificial
<220> FEATURE:
<223> OTHER INFORMATION: Synthetic construct

<400> SEQUENCE: 21

Ser Thr Ser Asn Leu Met Asp

```
1               5

<210> SEQ ID NO 22
<211> LENGTH: 7
<212> TYPE: PRT
<213> ORGANISM: Artificial
<220> FEATURE:
<223> OTHER INFORMATION: Synthetic construct

<400> SEQUENCE: 22

Ser Thr Ser Asn Leu Val Tyr
1               5

<210> SEQ ID NO 23
<211> LENGTH: 7
<212> TYPE: PRT
<213> ORGANISM: Artificial
<220> FEATURE:
<223> OTHER INFORMATION: Synthetic construct

<400> SEQUENCE: 23

Ser Thr Ser Asn Leu Val Trp
1               5

<210> SEQ ID NO 24
<211> LENGTH: 9
<212> TYPE: PRT
<213> ORGANISM: Artificial
<220> FEATURE:
<223> OTHER INFORMATION: Synthetic construct

<400> SEQUENCE: 24

Gln Gln Tyr Ser Gly Tyr His Phe Thr
1               5

<210> SEQ ID NO 25
<211> LENGTH: 9
<212> TYPE: PRT
<213> ORGANISM: Artificial
<220> FEATURE:
<223> OTHER INFORMATION: Synthetic construct

<400> SEQUENCE: 25

Gln His Tyr Ser Gly Tyr His Phe Thr
1               5

<210> SEQ ID NO 26
<211> LENGTH: 9
<212> TYPE: PRT
<213> ORGANISM: Artificial
<220> FEATURE:
<223> OTHER INFORMATION: Synthetic construct

<400> SEQUENCE: 26

Gln Asn Tyr Ser Gly Tyr His Phe Thr
1               5

<210> SEQ ID NO 27
<211> LENGTH: 9
<212> TYPE: PRT
<213> ORGANISM: Artificial
<220> FEATURE:
<223> OTHER INFORMATION: Synthetic construct

<400> SEQUENCE: 27

Gln Gln Tyr Ser Gly Tyr Phe Phe Thr
1               5
```

```
<210> SEQ ID NO 28
<211> LENGTH: 9
<212> TYPE: PRT
<213> ORGANISM: Artificial
<220> FEATURE:
<223> OTHER INFORMATION: Synthetic construct

<400> SEQUENCE: 28

Gln Gln Tyr Ser Gly Tyr Gln Phe Thr
1               5

<210> SEQ ID NO 29
<211> LENGTH: 9
<212> TYPE: PRT
<213> ORGANISM: Artificial
<220> FEATURE:
<223> OTHER INFORMATION: Synthetic construct

<400> SEQUENCE: 29

Gln Gln Tyr Ser Gly Tyr Thr Phe Thr
1               5

<210> SEQ ID NO 30
<211> LENGTH: 9
<212> TYPE: PRT
<213> ORGANISM: Artificial
<220> FEATURE:
<223> OTHER INFORMATION: Synthetic construct

<400> SEQUENCE: 30

Gln Gln Tyr Ser Gly Tyr Ser Phe Thr
1               5

<210> SEQ ID NO 31
<211> LENGTH: 9
<212> TYPE: PRT
<213> ORGANISM: Artificial
<220> FEATURE:
<223> OTHER INFORMATION: Synthetic construct

<400> SEQUENCE: 31

Gln Leu Tyr Ser Gly Tyr His Phe Thr
1               5

<210> SEQ ID NO 32
<211> LENGTH: 9
<212> TYPE: PRT
<213> ORGANISM: Artificial
<220> FEATURE:
<223> OTHER INFORMATION: Synthetic construct

<400> SEQUENCE: 32

Gln Pro Tyr Ser Gly Tyr His Phe Thr
1               5

<210> SEQ ID NO 33
<211> LENGTH: 9
<212> TYPE: PRT
<213> ORGANISM: Artificial
<220> FEATURE:
<223> OTHER INFORMATION: Synthetic construct

<400> SEQUENCE: 33

Gln His Tyr Leu Gly Tyr His Phe Thr
1               5

<210> SEQ ID NO 34
```

```
<211> LENGTH: 9
<212> TYPE: PRT
<213> ORGANISM: Artificial
<220> FEATURE:
<223> OTHER INFORMATION: Synthetic construct

<400> SEQUENCE: 34

Gln His His Ser Gly Tyr His Phe Thr
1               5

<210> SEQ ID NO 35
<211> LENGTH: 9
<212> TYPE: PRT
<213> ORGANISM: Artificial
<220> FEATURE:
<223> OTHER INFORMATION: Synthetic construct

<400> SEQUENCE: 35

Gln His Tyr Ser Gly Tyr His Trp Thr
1               5

<210> SEQ ID NO 36
<211> LENGTH: 9
<212> TYPE: PRT
<213> ORGANISM: Artificial
<220> FEATURE:
<223> OTHER INFORMATION: Synthetic construct

<400> SEQUENCE: 36

Gln Trp Tyr Ser Gly Tyr His Phe Thr
1               5

<210> SEQ ID NO 37
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is Q, N, H, L, P or W
<220> FEATURE:
<221> NAME/KEY: MISC_FEATURE
<222> LOCATION: (3)..(3)
<223> OTHER INFORMATION: X is Y or H
<220> FEATURE:
<221> NAME/KEY: MISC_FEATURE
<222> LOCATION: (4)..(4)
<223> OTHER INFORMATION: X is S or L
<220> FEATURE:
<221> NAME/KEY: MISC_FEATURE
<222> LOCATION: (7)..(7)
<223> OTHER INFORMATION: X is H, F, Q or T
<220> FEATURE:
<221> NAME/KEY: MISC_FEATURE
<222> LOCATION: (8)..(8)
<223> OTHER INFORMATION: X is F or W

<400> SEQUENCE: 37

Gln Xaa Xaa Xaa Gly Tyr Xaa Xaa Thr
1               5

<210> SEQ ID NO 38
<211> LENGTH: 10
<212> TYPE: PRT
<213> ORGANISM: Mus sp.

<400> SEQUENCE: 38

Gly Leu Thr Phe Ser Arg Tyr Gly Met Ser
1               5                   10
```

```
<210> SEQ ID NO 39
<211> LENGTH: 10
<212> TYPE: PRT
<213> ORGANISM: Artificial
<220> FEATURE:
<223> OTHER INFORMATION: Synthetic construct

<400> SEQUENCE: 39

Gly Leu Thr Phe Ser Arg Tyr Thr Met Ser
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic construct

<400> SEQUENCE: 40

Gly Leu Thr Phe Ser Arg Tyr Pro Met Ser
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic construct

<400> SEQUENCE: 41

Gly Leu Asn Phe Ser Arg Tyr Gly Met Ser
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: X is T or N
<220> FEATURE:
<221> NAME/KEY: MISC_FEATURE
<222> LOCATION: (8)..(8)
<223> OTHER INFORMATION: X is G, T or P

<400> SEQUENCE: 42

Gly Leu Xaa Phe Ser Arg Tyr Xaa Met Ser
1               5                   10

<210> SEQ ID NO 43
<211> LENGTH: 17
<212> TYPE: PRT
<213> ORGANISM: Mus sp.

<400> SEQUENCE: 43

Ala Ile Asn Ser His Gly Gly Ser Thr Tyr Tyr Ser Asp Thr Val Lys
1               5                   10                  15
Gly

<210> SEQ ID NO 44
<211> LENGTH: 17
<212> TYPE: PRT
<213> ORGANISM: Artificial
<220> FEATURE:
```

-continued

<223> OTHER INFORMATION: Synthetic construct

<400> SEQUENCE: 44

Ala Ile Asn Ser Ser Gly Gly Ser Thr Tyr Tyr Ser Asp Thr Val Lys
1               5                   10                  15

Gly

<210> SEQ ID NO 45
<211> LENGTH: 17
<212> TYPE: PRT
<213> ORGANISM: Artificial
<220> FEATURE:
<223> OTHER INFORMATION: Synthetic construct

<400> SEQUENCE: 45

Ala Ile Asn Ser Arg Gly Gly Ser Thr Tyr Tyr Ser Asp Thr Val Lys
1               5                   10                  15

Gly

<210> SEQ ID NO 46
<211> LENGTH: 17
<212> TYPE: PRT
<213> ORGANISM: Artificial
<220> FEATURE:
<223> OTHER INFORMATION: Synthetic construct

<400> SEQUENCE: 46

Ala Ile Asn Ser Val Gly Gly Ser Thr Tyr Tyr Ser Asp Thr Val Lys
1               5                   10                  15

Gly

<210> SEQ ID NO 47
<211> LENGTH: 17
<212> TYPE: PRT
<213> ORGANISM: Artificial
<220> FEATURE:
<223> OTHER INFORMATION: Synthetic construct

<400> SEQUENCE: 47

Ala Ile Asn Ser Glu Gly Gly Ser Thr Tyr Tyr Ser Asp Thr Val Lys
1               5                   10                  15

Gly

<210> SEQ ID NO 48
<211> LENGTH: 17
<212> TYPE: PRT
<213> ORGANISM: Artificial
<220> FEATURE:
<223> OTHER INFORMATION: Synthetic construct

<400> SEQUENCE: 48

Ala Ile Asn Ser Ile Gly Gly Ser Thr Tyr Tyr Ser Asp Thr Val Lys
1               5                   10                  15

Gly

<210> SEQ ID NO 49
<211> LENGTH: 17
<212> TYPE: PRT
<213> ORGANISM: Artificial
<220> FEATURE:
<223> OTHER INFORMATION: Synthetic construct

<400> SEQUENCE: 49

Ala Ile Asn Ser Met Gly Gly Ser Thr Tyr Tyr Ser Asp Thr Val Lys

```
                   1               5                  10                  15

Gly

<210> SEQ ID NO 50
<211> LENGTH: 17
<212> TYPE: PRT
<213> ORGANISM: Artificial
<220> FEATURE:
<223> OTHER INFORMATION: Synthetic construct

<400> SEQUENCE: 50

Ala Ile Asn Ser Thr Gly Gly Ser Thr Tyr Tyr Ser Asp Thr Val Lys
  1               5                  10                  15

Gly

<210> SEQ ID NO 51
<211> LENGTH: 17
<212> TYPE: PRT
<213> ORGANISM: Artificial
<220> FEATURE:
<223> OTHER INFORMATION: Synthetic construct

<400> SEQUENCE: 51

Ala Ile Asn Ser Lys Gly Gly Ser Thr Tyr Tyr Ser Asp Thr Val Lys
  1               5                  10                  15

Gly

<210> SEQ ID NO 52
<211> LENGTH: 17
<212> TYPE: PRT
<213> ORGANISM: Artificial
<220> FEATURE:
<223> OTHER INFORMATION: Synthetic construct

<400> SEQUENCE: 52

Ala Ile Asn Ser Pro Gly Gly Ser Thr Tyr Tyr Ser Asp Thr Val Lys
  1               5                  10                  15

Gly

<210> SEQ ID NO 53
<211> LENGTH: 17
<212> TYPE: PRT
<213> ORGANISM: Artificial
<220> FEATURE:
<223> OTHER INFORMATION: Synthetic construct

<400> SEQUENCE: 53

Ala Ile Asn Ser Gly Gly Gly Ser Thr Tyr Tyr Ser Asp Thr Val Lys
  1               5                  10                  15

Gly

<210> SEQ ID NO 54
<211> LENGTH: 17
<212> TYPE: PRT
<213> ORGANISM: Artificial
<220> FEATURE:
<223> OTHER INFORMATION: Synthetic construct

<400> SEQUENCE: 54

Ala Ile Asn Ser Tyr Gly Gly Ser Thr Tyr Tyr Ser Asp Thr Val Lys
  1               5                  10                  15

Gly
```

```
<210> SEQ ID NO 55
<211> LENGTH: 17
<212> TYPE: PRT
<213> ORGANISM: Artificial
<220> FEATURE:
<223> OTHER INFORMATION: Synthetic construct

<400> SEQUENCE: 55

Ala Ile Asn Ser Trp Gly Gly Ser Thr Tyr Tyr Ser Asp Thr Val Lys
1               5                   10                  15

Gly

<210> SEQ ID NO 56
<211> LENGTH: 17
<212> TYPE: PRT
<213> ORGANISM: Artificial
<220> FEATURE:
<223> OTHER INFORMATION: Synthetic construct

<400> SEQUENCE: 56

Ala Ile Asn Ser Ala Gly Gly Ser Thr Tyr Tyr Ser Asp Thr Val Lys
1               5                   10                  15

Gly

<210> SEQ ID NO 57
<211> LENGTH: 17
<212> TYPE: PRT
<213> ORGANISM: Artificial
<220> FEATURE:
<223> OTHER INFORMATION: Synthetic construct

<400> SEQUENCE: 57

Ala Ile Asn Ser Asp Gly Gly Ser Thr Tyr Tyr Ser Asp Thr Val Lys
1               5                   10                  15

Gly

<210> SEQ ID NO 58
<211> LENGTH: 17
<212> TYPE: PRT
<213> ORGANISM: Artificial
<220> FEATURE:
<223> OTHER INFORMATION: Synthetic construct

<400> SEQUENCE: 58

Ala Ile Asn Ser Leu Gly Gly Ser Thr Tyr Tyr Ser Asp Thr Val Lys
1               5                   10                  15

Gly

<210> SEQ ID NO 59
<211> LENGTH: 17
<212> TYPE: PRT
<213> ORGANISM: Artificial
<220> FEATURE:
<223> OTHER INFORMATION: Synthetic construct

<400> SEQUENCE: 59

Ala Ile Asn Ser Asn Gly Gly Ser Thr Tyr Tyr Ser Asp Thr Val Lys
1               5                   10                  15

Gly

<210> SEQ ID NO 60
<211> LENGTH: 17
<212> TYPE: PRT
<213> ORGANISM: Artificial
<220> FEATURE:
```

<223> OTHER INFORMATION: Synthetic construct

<400> SEQUENCE: 60

Ala Ile Thr Ser Ser Gly Gly Ser Thr Tyr Tyr Ser Asp Thr Val Lys
1               5                   10                  15

Gly

<210> SEQ ID NO 61
<211> LENGTH: 17
<212> TYPE: PRT
<213> ORGANISM: Artificial
<220> FEATURE:
<223> OTHER INFORMATION: Synthetic construct

<400> SEQUENCE: 61

Ala Ile Lys Ser Ser Gly Gly Ser Thr Tyr Tyr Ser Asp Thr Val Lys
1               5                   10                  15

Gly

<210> SEQ ID NO 62
<211> LENGTH: 17
<212> TYPE: PRT
<213> ORGANISM: Artificial
<220> FEATURE:
<223> OTHER INFORMATION: Synthetic construct

<400> SEQUENCE: 62

Ala Ile Lys Ser Asn Gly Gly Ser Thr Tyr Tyr Ser Asp Thr Val Lys
1               5                   10                  15

Gly

<210> SEQ ID NO 63
<211> LENGTH: 17
<212> TYPE: PRT
<213> ORGANISM: Artificial
<220> FEATURE:
<223> OTHER INFORMATION: Synthetic construct

<400> SEQUENCE: 63

Arg Ile Thr Ser Ser Gly Gly Ser Thr Tyr Tyr Ser Asp Thr Val Lys
1               5                   10                  15

Gly

<210> SEQ ID NO 64
<211> LENGTH: 17
<212> TYPE: PRT
<213> ORGANISM: Artificial
<220> FEATURE:
<223> OTHER INFORMATION: Synthetic construct

<400> SEQUENCE: 64

His Ile Lys Ser Ser Gly Gly Ser Thr Tyr Tyr Ser Asp Thr Val Lys
1               5                   10                  15

Gly

<210> SEQ ID NO 65
<211> LENGTH: 17
<212> TYPE: PRT
<213> ORGANISM: Artificial
<220> FEATURE:
<223> OTHER INFORMATION: Synthetic construct

<400> SEQUENCE: 65

Ala Ile Thr Ser Ser Gly Gly Ser Thr Lys Tyr Ser Asp Thr Val Lys

```
1               5                   10                  15

Gly

<210> SEQ ID NO 66
<211> LENGTH: 17
<212> TYPE: PRT
<213> ORGANISM: Artificial
<220> FEATURE:
<223> OTHER INFORMATION: Synthetic construct

<400> SEQUENCE: 66

Ala Ile Lys Ala Ser Gly Gly Ser Thr Tyr Tyr Ser Asp Thr Val Lys
1               5                   10                  15

Gly

<210> SEQ ID NO 67
<211> LENGTH: 17
<212> TYPE: PRT
<213> ORGANISM: Artificial
<220> FEATURE:
<223> OTHER INFORMATION: Synthetic construct

<400> SEQUENCE: 67

Ala Ile Lys Ser Ser Gly Ser Ser Thr Tyr Tyr Ser Asp Thr Val Lys
1               5                   10                  15

Gly

<210> SEQ ID NO 68
<211> LENGTH: 17
<212> TYPE: PRT
<213> ORGANISM: Artificial
<220> FEATURE:
<223> OTHER INFORMATION: Synthetic construct

<400> SEQUENCE: 68

Ala Ile Lys Ser Leu Gly Gly Ser Thr Tyr Tyr Ser Asp Thr Val Lys
1               5                   10                  15

Gly

<210> SEQ ID NO 69
<211> LENGTH: 17
<212> TYPE: PRT
<213> ORGANISM: Artificial
<220> FEATURE:
<223> OTHER INFORMATION: Synthetic construct

<400> SEQUENCE: 69

Ala Ile Thr Ser Met Gly Gly Ser Thr Tyr Tyr Ser Asp Thr Val Lys
1               5                   10                  15

Gly

<210> SEQ ID NO 70
<211> LENGTH: 17
<212> TYPE: PRT
<213> ORGANISM: Artificial
<220> FEATURE:
<223> OTHER INFORMATION: Synthetic construct

<400> SEQUENCE: 70

Ala Gln Thr Ser Ser Gly Gly Ser Thr Tyr Tyr Ser Asp Thr Val Lys
1               5                   10                  15

Gly
```

```
<210> SEQ ID NO 71
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is A, R or H
<220> FEATURE:
<221> NAME/KEY: MISC_FEATURE
<222> LOCATION: (2)..(2)
<223> OTHER INFORMATION: X is I or Q
<220> FEATURE:
<221> NAME/KEY: MISC_FEATURE
<222> LOCATION: (3)..(3)
<223> OTHER INFORMATION: X is N, T or K
<220> FEATURE:
<221> NAME/KEY: MISC_FEATURE
<222> LOCATION: (4)..(4)
<223> OTHER INFORMATION: X is S or A
<220> FEATURE:
<221> NAME/KEY: MISC_FEATURE
<222> LOCATION: (5)..(5)
<223> OTHER INFORMATION: X is H, S, V, L, M, N, G, D, W, R, A, Y, K, P,
      T, I or E
<220> FEATURE:
<221> NAME/KEY: MISC_FEATURE
<222> LOCATION: (7)..(7)
<223> OTHER INFORMATION: X is G or S
<220> FEATURE:
<221> NAME/KEY: MISC_FEATURE
<222> LOCATION: (10)..(10)
<223> OTHER INFORMATION: X is Y or K

<400> SEQUENCE: 71

Xaa Xaa Xaa Xaa Xaa Gly Xaa Ser Thr Xaa Tyr Ser Asp Thr Val Lys
1               5                   10                  15

Gly

<210> SEQ ID NO 72
<211> LENGTH: 4
<212> TYPE: PRT
<213> ORGANISM: Mus sp.

<400> SEQUENCE: 72

Leu Pro Asp Tyr
1

<210> SEQ ID NO 73
<211> LENGTH: 17
<212> TYPE: PRT
<213> ORGANISM: Artificial
<220> FEATURE:
<223> OTHER INFORMATION: Synthetic construct

<400> SEQUENCE: 73

Ala Ile Asn Ser Ser Gly Gly Ser Thr Tyr Tyr Ala Asp Ser Val Lys
1               5                   10                  15

Gly

<210> SEQ ID NO 74
<211> LENGTH: 108
<212> TYPE: PRT
<213> ORGANISM: Artificial
<220> FEATURE:
<223> OTHER INFORMATION: Synthetic construct

<400> SEQUENCE: 74

Glu Ile Val Leu Thr Gln Ser Pro Gly Thr Leu Ser Leu Ser Pro Gly
```

```
                1               5                   10                  15
Glu Arg Ala Thr Leu Ser Cys Arg Ala Ser Gln Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ala Gly Ile Pro Asp Arg Phe Ser
            50                  55                  60

Gly Ser Gly Ser Gly Thr Asp Phe Thr Leu Thr Ile Ser Arg Leu Glu
65                      70                  75                  80

Pro Glu Asp Phe Ala Val Tyr Tyr Cys Gln His Tyr Ser Gly Tyr His
                    85                  90                  95

Phe Thr Phe Gly Gly Gly Thr Lys Val Glu Ile Lys
                100                 105
```

<210> SEQ ID NO 75
<211> LENGTH: 108
<212> TYPE: PRT
<213> ORGANISM: Artificial
<220> FEATURE:
<223> OTHER INFORMATION: Synthetic construct

<400> SEQUENCE: 75

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Thr Gly Ile Pro Asp Arg Phe Ser
            50                  55                  60

Gly Ser Gly Ser Gly Thr Asp Phe Thr Leu Thr Ile Ser Arg Leu Glu
65                      70                  75                  80

Pro Glu Asp Phe Ala Val Tyr Tyr Cys Gln Asn Tyr Ser Gly Tyr His
                    85                  90                  95

Phe Thr Phe Gly Gly Gly Thr Lys Val Glu Ile Lys
                100                 105
```

<210> SEQ ID NO 76
<211> LENGTH: 108
<212> TYPE: PRT
<213> ORGANISM: Artificial
<220> FEATURE:
<223> OTHER INFORMATION: Synthetic construct

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ser Gly Ile Pro Asp Arg Phe Ser
            50                  55                  60

Gly Ser Gly Ser Gly Thr Asp Phe Thr Leu Thr Ile Ser Arg Leu Glu
65                      70                  75                  80

Pro Glu Asp Phe Ala Val Tyr Tyr Cys Gln Gln Tyr Ser Gly Tyr Phe
                    85                  90                  95

Phe Thr Phe Gly Gly Gly Thr Lys Leu Glu Ile Lys
```

-continued

<210> SEQ ID NO 77
<211> LENGTH: 108
<212> TYPE: PRT
<213> ORGANISM: Artificial
<220> FEATURE:
<223> OTHER INFORMATION: Synthetic construct

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Gly Tyr Gln
                85                  90                  95

Phe Thr Phe Gly Gly Gly Thr Lys Val Glu Ile Lys
            100                 105

<210> SEQ ID NO 78
<211> LENGTH: 108
<212> TYPE: PRT
<213> ORGANISM: Artificial
<220> FEATURE:
<223> OTHER INFORMATION: Synthetic construct

<400> SEQUENCE: 78

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Gly Tyr Thr
                85                  90                  95

Phe Thr Phe Gly Gly Gly Thr Lys Val Glu Ile Lys
            100                 105

<210> SEQ ID NO 79
<211> LENGTH: 108
<212> TYPE: PRT
<213> ORGANISM: Artificial
<220> FEATURE:
<223> OTHER INFORMATION: Synthetic construct

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

```
Tyr Leu His Trp Tyr Gln Gln Lys Pro Gly Gln Ala Pro Arg Leu Leu
            35                  40                  45

Ile Tyr Ser Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Gly Tyr Gln
                85                  90                  95

Phe Thr Phe Gly Gly Gly Thr Lys Leu Glu Ile Lys
            100                 105

<210> SEQ ID NO 80
<211> LENGTH: 108
<212> TYPE: PRT
<213> ORGANISM: Artificial
<220> FEATURE:
<223> OTHER INFORMATION: Synthetic construct

<400> SEQUENCE: 80

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Gly Tyr Ser
                85                  90                  95

Phe Thr Phe Gly Gly Gly Thr Lys Val Glu Ile Lys
            100                 105

<210> SEQ ID NO 81
<211> LENGTH: 108
<212> TYPE: PRT
<213> ORGANISM: Artificial
<220> FEATURE:
<223> OTHER INFORMATION: Synthetic construct

<400> SEQUENCE: 81

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 82
<211> LENGTH: 108
```

```
<212> TYPE: PRT
<213> ORGANISM: Artificial
<220> FEATURE:
<223> OTHER INFORMATION: Synthetic construct

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Tyr Ser Gly Tyr His
                85                  90                  95

Phe Thr Phe Gly Gly Gly Thr Lys Val Glu Ile Lys
            100                 105

<210> SEQ ID NO 83
<211> LENGTH: 108
<212> TYPE: PRT
<213> ORGANISM: Artificial
<220> FEATURE:
<223> OTHER INFORMATION: Synthetic construct

<400> SEQUENCE: 83

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Pro Tyr Ser Gly Tyr His
                85                  90                  95

Phe Thr Phe Gly Gly Gly Thr Lys Val Glu Ile Lys
            100                 105

<210> SEQ ID NO 84
<211> LENGTH: 108
<212> TYPE: PRT
<213> ORGANISM: Artificial
<220> FEATURE:
<223> OTHER INFORMATION: Synthetic construct

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Asn Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 85
<211> LENGTH: 108
<212> TYPE: PRT
<213> ORGANISM: Artificial
<220> FEATURE:
<223> OTHER INFORMATION: Synthetic construct

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Gly Tyr Gln
                85                  90                  95

Phe Thr Phe Gly Gly Gly Thr Lys Val Glu Ile Lys
            100                 105

<210> SEQ ID NO 86
<211> LENGTH: 108
<212> TYPE: PRT
<213> ORGANISM: Artificial
<220> FEATURE:
<223> OTHER INFORMATION: Synthetic construct

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 87
<211> LENGTH: 108
<212> TYPE: PRT
<213> ORGANISM: Artificial
<220> FEATURE:
<223> OTHER INFORMATION: Synthetic construct

```
<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Asp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 88
<211> LENGTH: 108
<212> TYPE: PRT
<213> ORGANISM: Artificial
<220> FEATURE:
<223> OTHER INFORMATION: Synthetic construct

<400> SEQUENCE: 88

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Pro Tyr Ser Gly Tyr His
                85                  90                  95

Phe Thr Phe Gly Gly Gly Thr Lys Val Glu Ile Lys
            100                 105

<210> SEQ ID NO 89
<211> LENGTH: 108
<212> TYPE: PRT
<213> ORGANISM: Artificial
<220> FEATURE:
<223> OTHER INFORMATION: Synthetic construct

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
```

```
                            85                  90                  95

Phe Thr Phe Gly Gly Gly Thr Lys Val Glu Ile Lys
            100                 105

<210> SEQ ID NO 90
<211> LENGTH: 108
<212> TYPE: PRT
<213> ORGANISM: Artificial
<220> FEATURE:
<223> OTHER INFORMATION: Synthetic construct

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Val Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Leu Gly Tyr His
                85                  90                  95

Phe Thr Phe Gly Gly Gly Thr Lys Val Glu Ile Lys
            100                 105

<210> SEQ ID NO 91
<211> LENGTH: 108
<212> TYPE: PRT
<213> ORGANISM: Artificial
<220> FEATURE:
<223> OTHER INFORMATION: Synthetic construct

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Arg Ala Leu Ser Ser Val Ser Ser Ser
            20                  25                  30

Tyr Leu His Trp Tyr Gln Gln Lys Pro Gly Gln Ala Pro Arg Leu Leu
            35                  40                  45

Ile Tyr Ser Thr Ser Asn Leu Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Leu Gly Tyr His
                85                  90                  95

Phe Thr Phe Gly Gly Gly Thr Lys Val Glu Ile Lys
            100                 105

<210> SEQ ID NO 92
<211> LENGTH: 108
<212> TYPE: PRT
<213> ORGANISM: Artificial
<220> FEATURE:
<223> OTHER INFORMATION: Synthetic construct

<400> SEQUENCE: 92

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Leu Gly Tyr His
                85                  90                  95

Phe Thr Phe Gly Gly Gly Thr Lys Val Glu Ile Lys
            100                 105

<210> SEQ ID NO 93
<211> LENGTH: 108
<212> TYPE: PRT
<213> ORGANISM: Artificial
<220> FEATURE:
<223> OTHER INFORMATION: Synthetic construct

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Phe Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 94
<211> LENGTH: 108
<212> TYPE: PRT
<213> ORGANISM: Artificial
<220> FEATURE:
<223> OTHER INFORMATION: Synthetic construct

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Thr Trp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 95
<211> LENGTH: 108
<212> TYPE: PRT
<213> ORGANISM: Artificial
<220> FEATURE:
<223> OTHER INFORMATION: Synthetic construct

<400> SEQUENCE: 95

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Met Asp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 96
<211> LENGTH: 108
<212> TYPE: PRT
<213> ORGANISM: Artificial
<220> FEATURE:
<223> OTHER INFORMATION: Synthetic construct

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Tyr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105

<210> SEQ ID NO 97
<211> LENGTH: 108
<212> TYPE: PRT
<213> ORGANISM: Artificial
<220> FEATURE:
<223> OTHER INFORMATION: Synthetic construct

<400> SEQUENCE: 97

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser
            20                  25                  30

Tyr Leu His Trp Tyr Gln Gln Lys Pro Gly Gln Ala Pro Arg Leu Leu
        35                  40                  45

```
Ile Tyr Ser Thr Ser Asn Leu Val Trp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Phe Thr Phe Gly Gly Gly Thr Lys Val Glu Ile Lys
            100                 105
```

<210> SEQ ID NO 98
<211> LENGTH: 108
<212> TYPE: PRT
<213> ORGANISM: Artificial
<220> FEATURE:
<223> OTHER INFORMATION: Synthetic construct

<400> SEQUENCE: 98

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Phe Thr Phe Gly Gly Gly Thr Lys Val Glu Ile Lys
            100                 105
```

<210> SEQ ID NO 99
<211> LENGTH: 108
<212> TYPE: PRT
<213> ORGANISM: Artificial
<220> FEATURE:
<223> OTHER INFORMATION: Synthetic construct

<400> SEQUENCE: 99

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Ser Gly Tyr His
                85                  90                  95

Trp Thr Phe Gly Gly Gly Thr Lys Val Glu Ile Lys
            100                 105
```

<210> SEQ ID NO 100
<211> LENGTH: 108
<212> TYPE: PRT
<213> ORGANISM: Artificial

```
<220> FEATURE:
<223> OTHER INFORMATION: Synthetic construct

<400> SEQUENCE: 100

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Trp Tyr Ser Gly Tyr His
                85                  90                  95

Phe Thr Phe Gly Gly Gly Thr Lys Val Glu Ile Lys
            100                 105

<210> SEQ ID NO 101
<211> LENGTH: 108
<212> TYPE: PRT
<213> ORGANISM: Artificial
<220> FEATURE:
<223> OTHER INFORMATION: Synthetic construct

<400> SEQUENCE: 101

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Tyr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Phe Thr Phe Gly Gly Gly Thr Lys Val Glu Ile Lys
            100                 105

<210> SEQ ID NO 102
<211> LENGTH: 108
<212> TYPE: PRT
<213> ORGANISM: Artificial
<220> FEATURE:
<223> OTHER INFORMATION: Synthetic construct

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Tyr Gly Ile Pro Asp Arg Phe Ser
    50                  55                  60

Gly Ser Gly Ser Gly Thr Asp Phe Thr Leu Thr Ile Ser Arg Leu Glu
```

-continued

```
                65                  70                  75                  80
Pro Glu Asp Phe Ala Val Tyr Tyr Cys Gln His Tyr Ser Gly Tyr His
                    85                  90                  95

Trp Thr Phe Gly Gly Gly Thr Lys Val Glu Ile Lys
                100                 105

<210> SEQ ID NO 103
<211> LENGTH: 113
<212> TYPE: PRT
<213> ORGANISM: Artificial
<220> FEATURE:
<223> OTHER INFORMATION: Synthetic construct

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
                20                  25                  30

Gly Met Ser Trp Val Arg Gln Ala Pro Gly Lys Gly Leu Glu Trp Val
            35                  40                  45

Ser Ala Ile Asn Ser Ser Gly Gly Ser Thr Tyr Tyr Ser Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
                100                 105                 110

Ser

<210> SEQ ID NO 104
<211> LENGTH: 113
<212> TYPE: PRT
<213> ORGANISM: Artificial
<220> FEATURE:
<223> OTHER INFORMATION: Synthetic construct

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
                20                  25                  30

Gly Met Ser Trp Val Arg Gln Ala Pro Gly Lys Gly Leu Glu Trp Val
            35                  40                  45

Ser Ala Ile Asn Ser Arg Gly Gly Ser Thr Tyr Tyr Ser Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
                100                 105                 110

Ser

<210> SEQ ID NO 105
<211> LENGTH: 113
<212> TYPE: PRT
<213> ORGANISM: Artificial
<220> FEATURE:
```

<223> OTHER INFORMATION: Synthetic construct

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Val Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 106
<211> LENGTH: 113
<212> TYPE: PRT
<213> ORGANISM: Artificial
<220> FEATURE:
<223> OTHER INFORMATION: Synthetic construct

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Glu Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 107
<211> LENGTH: 113
<212> TYPE: PRT
<213> ORGANISM: Artificial
<220> FEATURE:
<223> OTHER INFORMATION: Synthetic construct

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Ile Gly Gly Ser Thr Tyr Tyr Ser Asp Thr Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser

<210> SEQ ID NO 108
<211> LENGTH: 113
<212> TYPE: PRT
<213> ORGANISM: Artificial
<220> FEATURE:
<223> OTHER INFORMATION: Synthetic construct

<400> SEQUENCE: 108

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Leu Thr Phe Ser Arg Tyr
                 20                  25                  30

Gly Met Ser Trp Val Arg Gln Ala Pro Gly Lys Gly Leu Glu Trp Val
             35                  40                  45

Ser Ala Ile Asn Ser Met Gly Gly Ser Thr Tyr Tyr Ser Asp Thr Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser

<210> SEQ ID NO 109
<211> LENGTH: 113
<212> TYPE: PRT
<213> ORGANISM: Artificial
<220> FEATURE:
<223> OTHER INFORMATION: Synthetic construct

<400> SEQUENCE: 109

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Leu Thr Phe Ser Arg Tyr
                 20                  25                  30

Gly Met Ser Trp Val Arg Gln Ala Pro Gly Lys Gly Leu Glu Trp Val
             35                  40                  45

Ser Ala Ile Asn Ser Thr Gly Ser Thr Tyr Tyr Ser Asp Thr Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser
```

```
<210> SEQ ID NO 110
<211> LENGTH: 113
<212> TYPE: PRT
<213> ORGANISM: Artificial
<220> FEATURE:
<223> OTHER INFORMATION: Synthetic construct

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Lys Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 111
<211> LENGTH: 113
<212> TYPE: PRT
<213> ORGANISM: Artificial
<220> FEATURE:
<223> OTHER INFORMATION: Synthetic construct

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Pro Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 112
<211> LENGTH: 113
<212> TYPE: PRT
<213> ORGANISM: Artificial
<220> FEATURE:
<223> OTHER INFORMATION: Synthetic construct

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30
```

Gly Met Ser Trp Val Arg Gln Ala Pro Gly Lys Gly Leu Glu Trp Val
            35                  40                  45

Ser Ala Ile Asn Ser Gly Gly Ser Thr Tyr Tyr Ser Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 113
<211> LENGTH: 113
<212> TYPE: PRT
<213> ORGANISM: Artificial
<220> FEATURE:
<223> OTHER INFORMATION: Synthetic construct

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
            35                  40                  45

Ser Ala Ile Asn Ser Tyr Gly Gly Ser Thr Tyr Tyr Ser Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 114
<211> LENGTH: 113
<212> TYPE: PRT
<213> ORGANISM: Artificial
<220> FEATURE:
<223> OTHER INFORMATION: Synthetic construct

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
            35                  40                  45

Ser Ala Ile Asn Ser Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser

<210> SEQ ID NO 115
<211> LENGTH: 113
<212> TYPE: PRT
<213> ORGANISM: Artificial
<220> FEATURE:
<223> OTHER INFORMATION: Synthetic construct

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Trp Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser
```

<210> SEQ ID NO 116
<211> LENGTH: 113
<212> TYPE: PRT
<213> ORGANISM: Artificial
<220> FEATURE:
<223> OTHER INFORMATION: Synthetic construct

<400> SEQUENCE: 116

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Ala Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser
```

<210> SEQ ID NO 117
<211> LENGTH: 113
<212> TYPE: PRT
<213> ORGANISM: Artificial
<220> FEATURE:
<223> OTHER INFORMATION: Synthetic construct

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Asp Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Pro Asp Tyr Trp Gly Gln Gly Thr Leu Val Thr Val Ser
            100                 105                 110

Ser

<210> SEQ ID NO 118
<211> LENGTH: 113
<212> TYPE: PRT
<213> ORGANISM: Artificial
<220> FEATURE:
<223> OTHER INFORMATION: Synthetic construct

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Leu Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Pro Asp Tyr Trp Gly Gln Gly Thr Leu Val Thr Val Ser
            100                 105                 110

Ser

<210> SEQ ID NO 119
<211> LENGTH: 113
<212> TYPE: PRT
<213> ORGANISM: Artificial
<220> FEATURE:
<223> OTHER INFORMATION: Synthetic construct

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Asn Ser Asn Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 120
<211> LENGTH: 113
<212> TYPE: PRT
<213> ORGANISM: Artificial
<220> FEATURE:
<223> OTHER INFORMATION: Synthetic construct

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Thr Ser Ser Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 121
<211> LENGTH: 113
<212> TYPE: PRT
<213> ORGANISM: Artificial
<220> FEATURE:
<223> OTHER INFORMATION: Synthetic construct

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Ser Trp Val Arg Gln Ala Pro Gly Lys Gly Leu Glu Trp Val
        35                  40                  45

Ser Ala Ile Asn Ser Ser Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 122
<211> LENGTH: 113
<212> TYPE: PRT
<213> ORGANISM: Artificial
```

```
<220> FEATURE:
<223> OTHER INFORMATION: Synthetic construct

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Ser Trp Val Arg Gln Ala Pro Gly Lys Gly Leu Glu Trp Val
        35                  40                  45

Ser Ala Ile Lys Ser Ser Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 123
<211> LENGTH: 113
<212> TYPE: PRT
<213> ORGANISM: Artificial
<220> FEATURE:
<223> OTHER INFORMATION: Synthetic construct

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Glu Trp Val
        35                  40                  45

Ser Ala Ile Thr Ser Ser Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 124
<211> LENGTH: 113
<212> TYPE: PRT
<213> ORGANISM: Artificial
<220> FEATURE:
<223> OTHER INFORMATION: Synthetic construct

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Asn Phe Ser Arg Tyr
            20                  25                  30

Gly Met Ser Trp Val Arg Gln Ala Pro Gly Lys Gly Leu Glu Trp Val
        35                  40                  45
```

```
Ser Ala Ile Thr Ser Ser Gly Gly Ser Thr Tyr Tyr Ser Asp Thr Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Pro Asp Tyr Trp Gly Gln Gly Thr Leu Val Thr Val Ser
            100                 105                 110
Ser
```

<210> SEQ ID NO 125
<211> LENGTH: 113
<212> TYPE: PRT
<213> ORGANISM: Artificial
<220> FEATURE:
<223> OTHER INFORMATION: Synthetic construct

<400> SEQUENCE: 125

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Leu Thr Phe Ser Arg Tyr
                 20                  25                  30
Gly Met Ser Trp Val Arg Gln Ala Pro Gly Lys Gly Leu Glu Trp Val
             35                  40                  45
Ser Ala Ile Lys Ser Ser Gly Gly Ser Thr Tyr Tyr Ser Asp Thr Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Pro Asp Tyr Trp Gly Gln Gly Thr Leu Val Thr Val Ser
            100                 105                 110
Ser
```

<210> SEQ ID NO 126
<211> LENGTH: 113
<212> TYPE: PRT
<213> ORGANISM: Artificial
<220> FEATURE:
<223> OTHER INFORMATION: Synthetic construct

<400> SEQUENCE: 126

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Leu Thr Phe Ser Arg Tyr
                 20                  25                  30
Gly Met Ser Trp Val Arg Gln Ala Pro Gly Lys Gly Leu Glu Trp Val
             35                  40                  45
Ser Ala Ile Lys Ser Asn Gly Gly Ser Thr Tyr Tyr Ser Asp Thr Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Pro Asp Tyr Trp Gly Gln Gly Thr Leu Val Thr Val Ser
            100                 105                 110
Ser
```

<210> SEQ ID NO 127
<211> LENGTH: 113
<212> TYPE: PRT
<213> ORGANISM: Artificial
<220> FEATURE:
<223> OTHER INFORMATION: Synthetic construct

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Arg Ile Thr Ser Ser Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 128
<211> LENGTH: 113
<212> TYPE: PRT
<213> ORGANISM: Artificial
<220> FEATURE:
<223> OTHER INFORMATION: Synthetic construct

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser His Ile Lys Ser Ser Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 129
<211> LENGTH: 113
<212> TYPE: PRT
<213> ORGANISM: Artificial
<220> FEATURE:
<223> OTHER INFORMATION: Synthetic construct

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr

-continued

```
                20                  25                  30
Gly Met Ser Trp Val Arg Gln Ala Pro Gly Lys Gly Leu Glu Trp Val
            35                  40                  45

Ser Ala Ile Thr Ser Ser Gly Gly Ser Thr Lys Tyr Ser Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
               100                 105                 110

Ser

<210> SEQ ID NO 130
<211> LENGTH: 113
<212> TYPE: PRT
<213> ORGANISM: Artificial
<220> FEATURE:
<223> OTHER INFORMATION: Synthetic construct

<400> SEQUENCE: 130

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Leu Thr Phe Ser Arg Tyr
                20                  25                  30

Gly Met Ser Trp Val Arg Gln Ala Pro Gly Lys Gly Leu Glu Trp Val
            35                  40                  45

Ser Ala Ile Lys Ala Ser Gly Gly Ser Thr Tyr Tyr Ser Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
               100                 105                 110

Ser

<210> SEQ ID NO 131
<211> LENGTH: 113
<212> TYPE: PRT
<213> ORGANISM: Artificial
<220> FEATURE:
<223> OTHER INFORMATION: Synthetic construct

<400> SEQUENCE: 131

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Leu Thr Phe Ser Arg Tyr
                20                  25                  30

Gly Met Ser Trp Val Arg Gln Ala Pro Gly Lys Gly Leu Glu Trp Val
            35                  40                  45

Ser Ala Ile Lys Ser Ser Gly Ser Thr Tyr Tyr Ser Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Leu Pro Asp Tyr Trp Gly Gln Gly Thr Leu Val Thr Val Ser
                100                 105                 110
Ser

<210> SEQ ID NO 132
<211> LENGTH: 113
<212> TYPE: PRT
<213> ORGANISM: Artificial
<220> FEATURE:
<223> OTHER INFORMATION: Synthetic construct

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Lys Ser Leu Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
                100                 105                 110
Ser

<210> SEQ ID NO 133
<211> LENGTH: 113
<212> TYPE: PRT
<213> ORGANISM: Artificial
<220> FEATURE:
<223> OTHER INFORMATION: Synthetic construct

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Lys Ser Leu Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
                100                 105                 110
Ser

<210> SEQ ID NO 134
<211> LENGTH: 113
<212> TYPE: PRT
<213> ORGANISM: Artificial
<220> FEATURE:
<223> OTHER INFORMATION: Synthetic construct

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Gly Met Ser Trp Val Arg Gln Ala Pro Gly Lys Gly Leu Glu Trp Val
        35                  40                  45

Ser Ala Gln Thr Ser Ser Gly Gly Ser Thr Tyr Tyr Ser Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 135
<211> LENGTH: 113
<212> TYPE: PRT
<213> ORGANISM: Artificial
<220> FEATURE:
<223> OTHER INFORMATION: Synthetic construct

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Glu Trp Val
        35                  40                  45

Ser Arg Ile Thr Ser Ser Gly Gly Ser Thr Tyr Tyr Ser Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser

<210> SEQ ID NO 136
<211> LENGTH: 113
<212> TYPE: PRT
<213> ORGANISM: Artificial
<220> FEATURE:
<223> OTHER INFORMATION: Synthetic construct

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Glu Trp Val
        35                  40                  45

Ser Ala Ile Lys Ser Ser Gly Gly Ser Thr Tyr Tyr Ser Asp Thr Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser

<210> SEQ ID NO 137
<211> LENGTH: 113
<212> TYPE: PRT
<213> ORGANISM: Artificial
<220> FEATURE:
<223> OTHER INFORMATION: Synthetic construct

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Glu Trp Val
        35                  40                  45

Ser Ala Ile Lys Ser Ser Gly Gly Ser Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser

<210> SEQ ID NO 138
<211> LENGTH: 113
<212> TYPE: PRT
<213> ORGANISM: Artificial
<220> FEATURE:
<223> OTHER INFORMATION: Synthetic construct

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Val Trp Val
        35                  40                  45

Ser Ala Ile Thr Ser Ser Gly Gly Ser Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Leu Pro Asp Tyr Trp Gly Gln Gly Thr Leu Val Thr Val Ser
                100                 105                 110

Ser

<210> SEQ ID NO 139
<211> LENGTH: 11
<212> TYPE: PRT
```

<213> ORGANISM: Homo sapiens

<400> SEQUENCE: 139

Trp Gly Gln Gly Thr Leu Val Thr Val Ser Ser
1               5                   10

<210> SEQ ID NO 140
<211> LENGTH: 108
<212> TYPE: PRT
<213> ORGANISM: Artificial
<220> FEATURE:
<223> OTHER INFORMATION: Synthetic construct

<400> SEQUENCE: 140

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Val Tyr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Phe Thr Phe Gly Gly Gly Thr Lys Val Glu Ile Lys
            100                 105

<210> SEQ ID NO 141
<211> LENGTH: 108
<212> TYPE: PRT
<213> ORGANISM: Artificial
<220> FEATURE:
<223> OTHER INFORMATION: Synthetic construct

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
                20                  25                  30

Tyr Leu His Trp Tyr Gln Gln Lys Pro Gly Gln Ala Pro Arg Leu Leu
            35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Trp Thr Phe Gly Gly Gly Thr Lys Val Glu Ile Lys
            100                 105

<210> SEQ ID NO 142
<211> LENGTH: 108
<212> TYPE: PRT
<213> ORGANISM: Artificial
<220> FEATURE:
<223> OTHER INFORMATION: Synthetic construct

<400> SEQUENCE: 142

Glu Ile Val Leu Thr Gln Ser Pro Gly Thr Leu Ser Leu Ser Pro Gly

```
                 1               5                  10                  15
Glu Arg Ala Thr Leu Ser Cys Arg Ala Ser Ser Val Ser Ser Ser
                 20                  25                  30

Tyr Leu His Trp Tyr Gln Gln Lys Pro Gly Gln Ala Pro Arg Leu Leu
                 35                  40                  45

Ile Tyr Ser Thr Ser Asn Leu Val Ala Gly Ile Pro Asp Arg Phe Ser
                 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Ser Gly Tyr His
                 85                  90                  95

Trp Thr Phe Gly Gly Gly Thr Lys Val Glu Ile Lys
                 100                 105
```

<210> SEQ ID NO 143
<211> LENGTH: 23
<212> TYPE: PRT
<213> ORGANISM: Homo sapiens

<400> SEQUENCE: 143

```
Glu Ile Val Leu Thr Gln Ser Pro Gly Thr Leu Ser Leu Ser Pro Gly
1               5                   10                  15

Glu Arg Ala Thr Leu Ser Cys
                20
```

<210> SEQ ID NO 144
<211> LENGTH: 15
<212> TYPE: PRT
<213> ORGANISM: Homo sapiens

<400> SEQUENCE: 144

```
Trp Tyr Ala Ala Lys Pro Gly Gln Ala Pro Arg Leu Leu Ile Tyr
1               5                   10                  15
```

<210> SEQ ID NO 145
<211> LENGTH: 32
<212> TYPE: PRT
<213> ORGANISM: Homo sapiens

<400> SEQUENCE: 145

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
                20                  25                  30
```

<210> SEQ ID NO 146
<211> LENGTH: 10
<212> TYPE: PRT
<213> ORGANISM: Homo sapiens

<400> SEQUENCE: 146

```
Phe Gly Gly Gly Thr Lys Val Glu Ile Lys
1               5                   10
```

<210> SEQ ID NO 147
<211> LENGTH: 10
<212> TYPE: PRT
<213> ORGANISM: Homo sapiens

<400> SEQUENCE: 147

```
Phe Gly Gly Gly Thr Lys Leu Glu Ile Lys
1               5                   10
```

```
<210> SEQ ID NO 148
<211> LENGTH: 25
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 149
<211> LENGTH: 25
<212> TYPE: PRT
<213> ORGANISM: Homo sapiens

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 150
<211> LENGTH: 25
<212> TYPE: PRT
<213> ORGANISM: Homo sapiens

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 151
<211> LENGTH: 14
<212> TYPE: PRT
<213> ORGANISM: Homo sapiens

<400> SEQUENCE: 151

Trp Val Arg Gln Ala Pro Gly Lys Gly Leu Glu Trp Val Ser
1               5                   10

<210> SEQ ID NO 152
<211> LENGTH: 32
<212> TYPE: PRT
<213> ORGANISM: Homo sapiens

<400> SEQUENCE: 152

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 153
<211> LENGTH: 32
<212> TYPE: PRT
<213> ORGANISM: Homo sapiens

<400> SEQUENCE: 153

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
```

<210> SEQ ID NO 154
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: X is A, V, T, or M
<220> FEATURE:
<221> NAME/KEY: MISC_FEATURE
<222> LOCATION: (7)..(7)
<223> OTHER INFORMATION: X is S, A, T, N, W, D or Y

<400> SEQUENCE: 154

Ser Thr Ser Asn Leu Xaa Xaa
1               5

<210> SEQ ID NO 155
<211> LENGTH: 106
<212> TYPE: PRT
<213> ORGANISM: Homo sapiens

<400> SEQUENCE: 155

Val Ala Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 156
<211> LENGTH: 315
<212> TYPE: DNA
<213> ORGANISM: Homo sapiens

<400> SEQUENCE: 156
gtggctgcac catctgtctt catcttcccg ccatctgatg agcagttgaa atctggaact    60
gcctctgttg tgtgcctgct gaataacttc tatcccagag aggccaaagt acagtggaag   120
gtggataacg ccctccaatc gggtaactcc caggagagtg tcacagagca ggacagcaag   180
gacagcacct acagcctcag cagcaccctg acgctgagca agcagactac gagaaacac   240 aaagtctacg cctgcgaagt cacccatcag ggcctgagct cgcccgtcac aaagagcttc   300
aacaggggag agtgc                                                    315

<210> SEQ ID NO 157
<211> LENGTH: 322
<212> TYPE: PRT
<213> ORGANISM: artificial
<220> FEATURE:
<223> OTHER INFORMATION: synthetic construct

<400> SEQUENCE: 157

```
Gly Pro Ser Val Phe Pro Leu Ala Pro Cys Ser Arg Ser Thr Ser Glu
1               5                   10                  15

Ser Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Lys Thr Tyr Thr Cys Asn
65                  70                  75                  80

Val Asp His Lys Pro Ser Asn Thr Lys Val Asp Lys Arg Val Glu Ser
                85                  90                  95

Lys Tyr Gly Pro Pro Cys Pro Pro Cys Pro Ala Pro Glu Phe Leu Gly
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser Gln
130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
290                 295                 300

His Glu Ala Leu His Asn His Tyr Thr Gln Lys Ser Leu Ser Leu Ser
305                 310                 315                 320

Leu Gly
```

<210> SEQ ID NO 158
<211> LENGTH: 970
<212> TYPE: DNA
<213> ORGANISM: Homo sapiens

<400> SEQUENCE: 158

```
ggcccatcgg tcttccccgct agcgccctgc tccaggagca cctccgagag cacagccgcc     60
ctgggctgcc tggtcaagga ctacttcccc gaaccggtga cggtgtcgtg gaactcaggc    120
gccctgacca gcggcgtgca caccttcccg gctgtcctac agtcctcagg actctactcc    180
gctcagcagc gtggtgaccg tgccctccag cagcttgggc acgaagacct acacctgcaa    240
```

-continued

```
cgtagatcac aagcccagca acaccaaggt ggacaagaga gttgagtcca aatatggtcc      300
cccatgccca ccctgcccag cacctgagtt cctggggga ccatcagtct tcctgttccc      360
cccaaaaccc aaggacactc tcatgatctc ccggacccct gaggtcacgt gcgtggtggt      420
ggacgtgagc caggaagacc ccgaggtcca gttcaactgg tacgtggatg gcgtggaggt      480
gcataatgcc aagacaaagc cgcgggagga gcagttcaac agcacgtacc gtgtggtcag      540
cgtcctcacc gtcctgcacc aggactggct gaacggcaag gagtacaagt gcaaggtctc      600
caacaaaggc ctcccgtcct ccatcgagaa aaccatctcc aaagccaaag ggcagccccg      660
agagccacag gtgtacaccc tgcccccatc ccaggaggag atgaccaaga accaggtcag      720
cctgacctgc ctggtcaaag gcttctaccc cagcgacatc gccgtggagt gggaaagcaa      780
tgggcagccg gagaacaact acaagaccac gcctcccgtg ctggactccg acggctcctt      840
cttcctctac agcaggctaa ccgtggacaa gagcaggtgg caggagggga atgtcttctc      900
atgctccgtg atgcatgagg ctctgcacaa ccactacaca cagaagagcc tctccctgtc      960
tctgggttga                                                            970
```